(12) United States Patent
Aklog et al.

(10) Patent No.: US 11,668,404 B2
(45) Date of Patent: Jun. 6, 2023

(54) SYSTEMS AND METHODS FOR A VARIABLE FLOW RESISTOR

(71) Applicant: PAVmed Inc., New York, NY (US)

(72) Inventors: Lishan Aklog, Purchase, NY (US); Richard Yazbeck, Norwell, MA (US); Michael Boutillette, San Francisco, CA (US); Peter Aliski, New York, NY (US); Jonathan O'Keefe, New York, NY (US); Amos Cruz, New York, NY (US)

(73) Assignee: PAVmed Inc., New York, NY (US)

( * ) Notice: Subject to any disclaimer, the term of this patent is extended or adjusted under 35 U.S.C. 154(b) by 0 days.

(21) Appl. No.: 16/845,752

(22) Filed: Apr. 10, 2020

(65) Prior Publication Data
US 2020/0325999 A1 Oct. 15, 2020

Related U.S. Application Data

(60) Provisional application No. 62/832,005, filed on Apr. 10, 2019.

(51) Int. Cl.
*F16K 15/02* (2006.01)
*F15D 1/02* (2006.01)

(52) U.S. Cl.
CPC ............ *F16K 15/021* (2013.01); *F15D 1/025* (2013.01)

(58) Field of Classification Search
CPC .... F15D 1/025; F15D 1/021; Y10T 137/7792; A61M 5/16881; F16K 15/021
(Continued)

(56) References Cited

U.S. PATENT DOCUMENTS

| 780,986 A | * | 1/1905 | Francis | G05D 7/0133 |
| | | | | 137/504 |
| 1,724,881 A | * | 8/1929 | Lund | B60T 11/32 |
| | | | | 303/84.2 |

(Continued)

FOREIGN PATENT DOCUMENTS

| DE | 2452117 A1 | 5/1976 |
| EP | 0228514 A1 | 7/1987 |

(Continued)

OTHER PUBLICATIONS

International Search Report for corresponding International Patent Application No. PCT/US20/27702, dated Jul. 17, 2020 (3 pages).
(Continued)

*Primary Examiner* — Reinaldo Sanchez-Medina
*Assistant Examiner* — Nicole Gardner
(74) *Attorney, Agent, or Firm* — Greenberg Traurig, LLP; Chinh H. Pham; Joshua I. Rudawitz

(57) ABSTRACT

The systems and methods of the present disclosure provides an independent passive variable resistor that can be interposed between a fluid reservoir at an inlet pressure and receptacle at an outlet pressure. The resistor can adjust resistance to the pressure difference from the input to the output so that the flow rate through it is a constant rate. The resistor can include a moveable element and a biasing mechanism located in a chamber to create a flow channel. Each side of the moveable element is exposed to the inlet and outlet pressures and moves within the flow channel to modify the resistance of the flow through the chamber in response to the pressures. The balance of these forces determines the position moveable element, which interacts with the fluid channel to determine the flow resistance through variable resistor. The biasing mechanism can pro-
(Continued)

vide the necessary pressure to establish equilibrium flow rate.

14 Claims, 49 Drawing Sheets

(58) Field of Classification Search
USPC .............................................. 138/46; 251/120
See application file for complete search history.

(56) References Cited

U.S. PATENT DOCUMENTS

| | | | | |
|---|---|---|---|---|
| 2,647,531 | A | * | 8/1953 | Berck ..................... G05D 7/014 |
| | | | | 137/220 |
| 2,781,061 | A | * | 2/1957 | Frey ........................ G05D 7/012 |
| | | | | 138/46 |
| 2,802,486 | A | * | 8/1957 | Frey ........................ G05D 7/012 |
| | | | | 138/46 |
| 3,837,362 | A | * | 9/1974 | Barnes .................. G05D 7/0133 |
| | | | | 138/45 |
| 4,011,894 | A | * | 3/1977 | Barnes ..................... F15D 1/02 |
| | | | | 138/46 |
| 4,361,147 | A | | 11/1982 | Aslanian et al. |
| 4,383,550 | A | * | 5/1983 | Sotokazu ............. G05D 7/0133 |
| | | | | 137/517 |
| 4,572,004 | A | | 2/1986 | White |
| 4,573,994 | A | | 3/1986 | Fischell et al. |
| 5,100,389 | A | | 3/1992 | Vaillancourt |
| 5,190,075 | A | | 3/1993 | Tentler et al. |
| 5,800,405 | A | | 9/1998 | McPhee |
| 6,053,888 | A | | 4/2000 | Kong |
| 6,213,986 | B1 | | 4/2001 | Darling et al. |
| 7,022,107 | B1 | | 4/2006 | Christensen et al. |
| 7,255,680 | B1 | | 8/2007 | Gharib |
| 7,654,982 | B2 | | 2/2010 | Carlisle et al. |
| 8,622,976 | B2 | | 1/2014 | Aklog et al. |
| 8,869,826 | B2 | * | 10/2014 | Chappel ............... G05D 7/0133 |
| | | | | 137/504 |
| 9,155,834 | B2 | | 10/2015 | Aklog et al. |
| 9,435,450 | B2 | | 9/2016 | Muennich |
| 10,596,314 | B2 | | 3/2020 | Lee |
| 2002/0156464 | A1 | | 10/2002 | Blischak et al. |
| 2003/0040709 | A1 | | 2/2003 | Mason |
| 2004/0221854 | A1 | | 11/2004 | Hete et al. |
| 2005/0034766 | A1 | | 2/2005 | Rado |
| 2005/0159708 | A1 | | 7/2005 | Sidler |
| 2006/0004330 | A1 | | 1/2006 | Carlisle et al. |
| 2007/0000488 | A1 | | 1/2007 | Koerner et al. |
| 2007/0066939 | A1 | | 3/2007 | Krulevitch et al. |
| 2007/0088267 | A1 | | 4/2007 | Shekalim |
| 2008/0154240 | A1 | | 6/2008 | Shippert |
| 2009/0088724 | A1 | | 4/2009 | Chebator et al. |
| 2011/0125103 | A1 | | 5/2011 | Rondeau |
| 2011/0226354 | A1 | | 9/2011 | Thordarson |
| 2012/0048403 | A1 | | 3/2012 | Chappel et al. |
| 2014/0083529 | A1 | | 3/2014 | Aklog et al. |
| 2014/0096552 | A1 | * | 4/2014 | Foesel .................... F25B 41/33 |
| | | | | 137/492.5 |
| 2019/0167914 | A1 | | 6/2019 | Stately et al. |
| 2020/0325999 | A1 | | 10/2020 | Aklog et al. |

FOREIGN PATENT DOCUMENTS

| | | |
|---|---|---|
| EP | 2722500 B1 | 8/2018 |
| EP | 3711792 A1 | 9/2020 |
| FR | 1437915 A | 5/1966 |
| FR | 2148395 A2 | 3/1973 |
| GB | 2014277 A | 8/1979 |
| GB | 1554629 A | 10/1979 |
| JP | S61164564 A | 7/1986 |
| JP | H02180274 A | 7/1990 |
| WO | 1981000519 A1 | 3/1981 |
| WO | 2019009898 A1 | 1/2019 |
| WO | 20220169800 A1 | 8/2022 |
| WO | 20220170110 A1 | 8/2022 |

OTHER PUBLICATIONS

International Search Report and Written Opinion dated Apr. 19, 2022 in corresponding International Patent Application No. PCT/US2022/014834 (8 pages).

International Search Report and Written Opinion dated May 12, 2022 in corresponding International Patent Application No. PCT/US2022/015332 (7 pages).

* cited by examiner

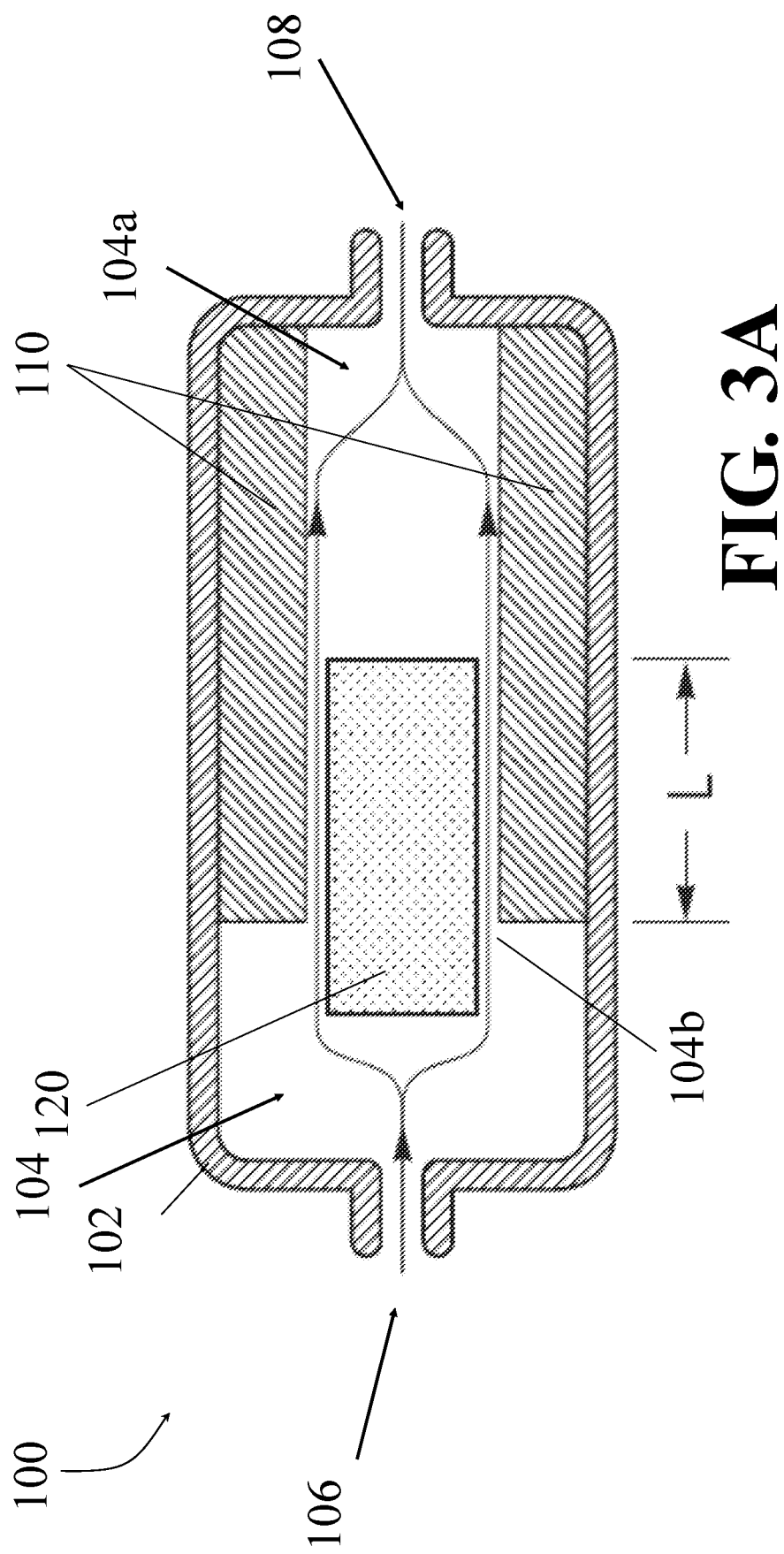

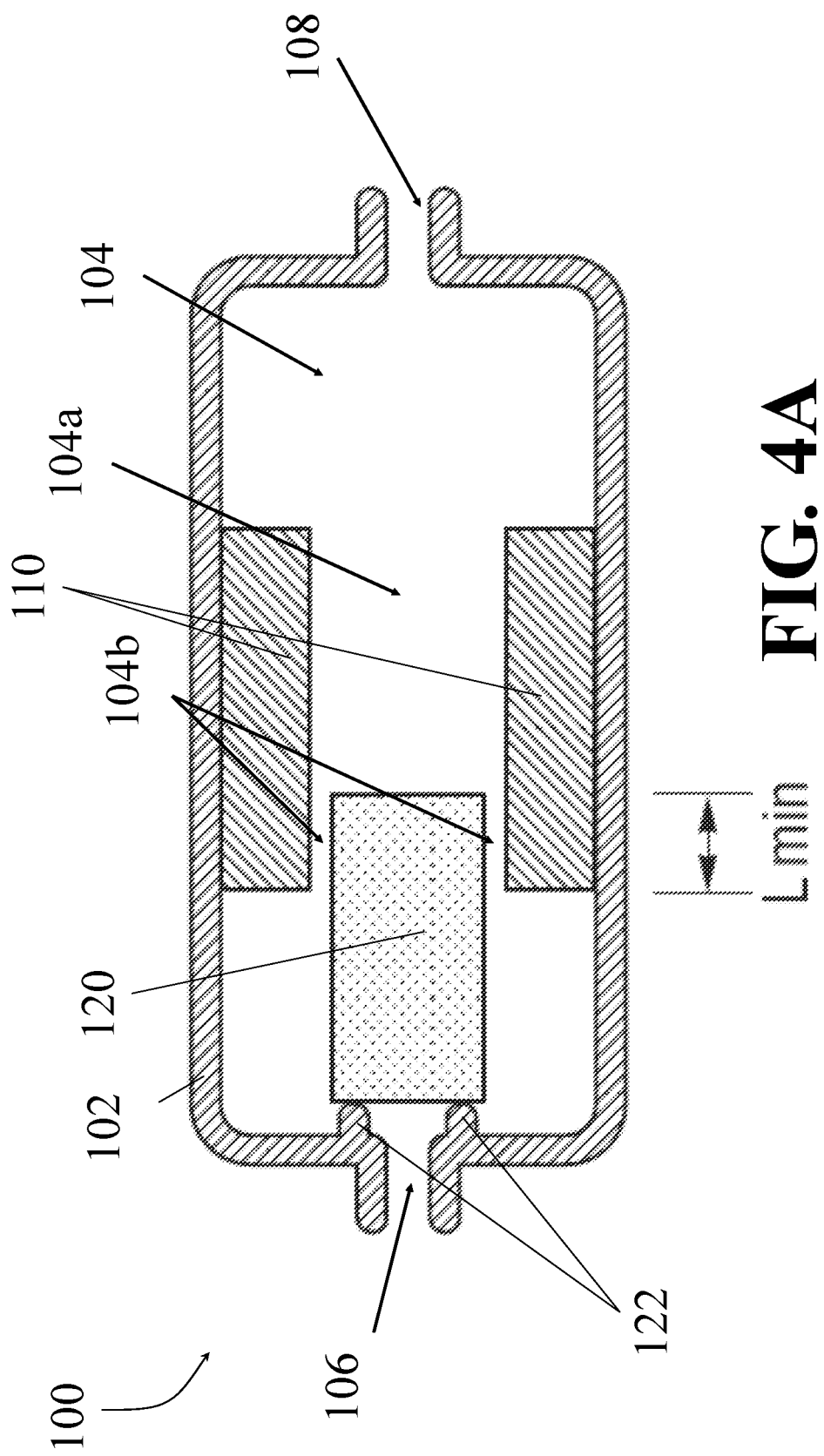

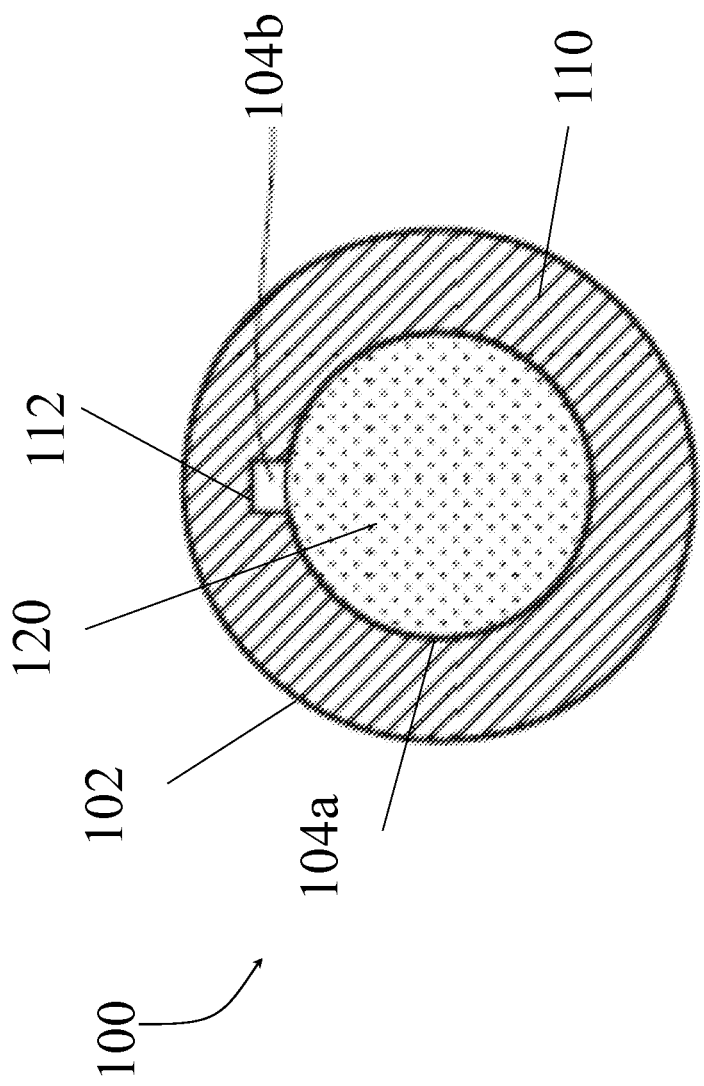

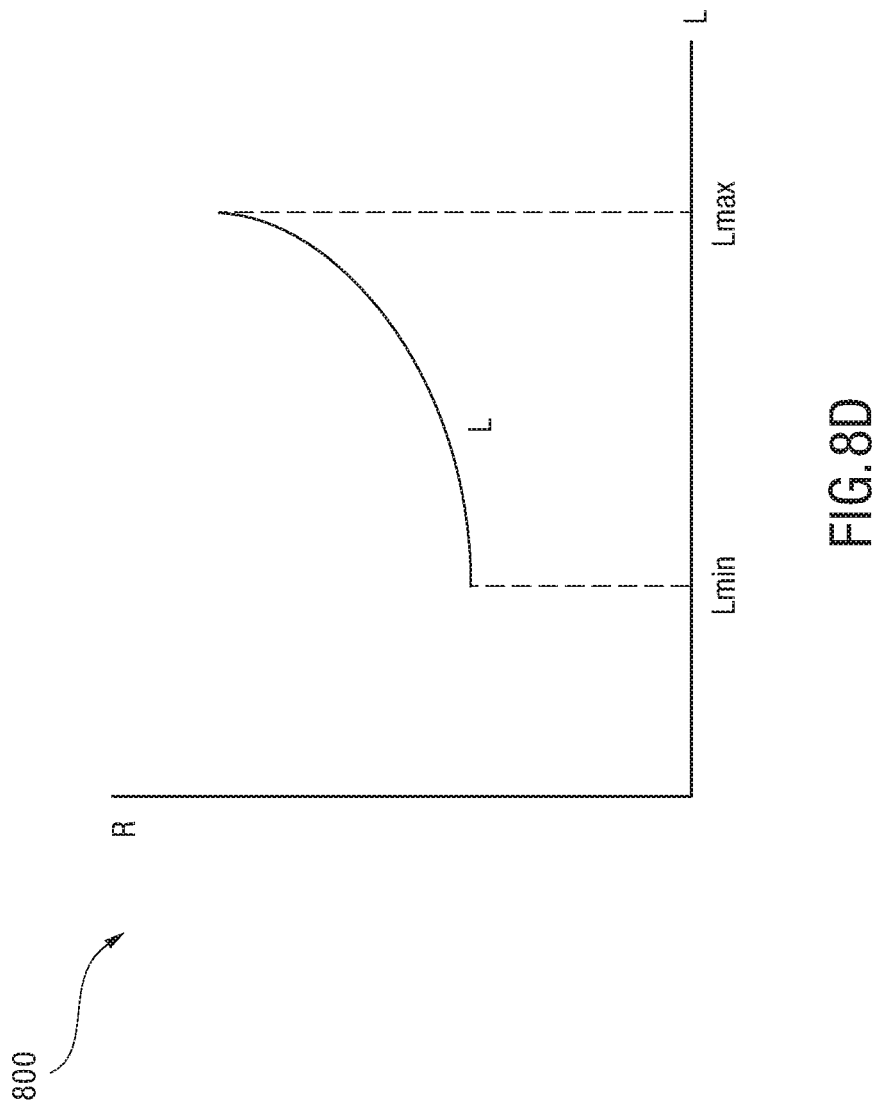

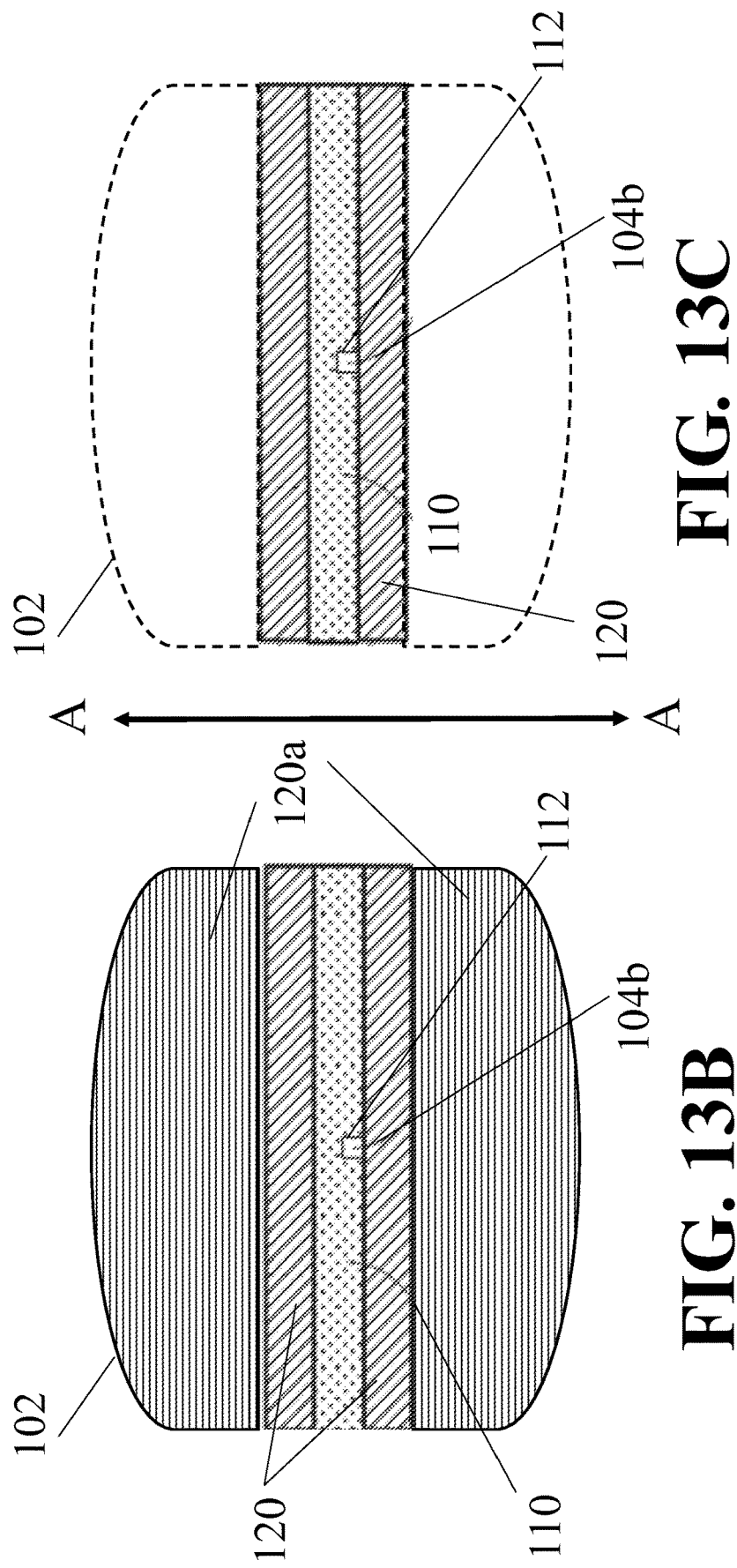

SYSTEMS AND METHODS FOR A VARIABLE FLOW RESISTOR

CROSS-REFERENCE TO RELATED APPLICATION(S)

This application claims priority to, and the benefit of, U.S. Provisional Application No. 62/832,005, filed Apr. 10, 2019, for all subject matter common to both applications. The disclosure of said provisional application is hereby incorporated by reference in its entirety.

FIELD OF THE INVENTION

The present disclosure relates to systems and methods for a passive variable flow resistor. More particularly, the present disclosure relates to a variable flow resistor for delivering fluids at a designated flow rate, despite a potentially changing pressure at an input of the variable flow resistor.

BACKGROUND

Many of fluid transfer applications require that the fluid flow is controlled to deliver a substance to a location at a specified rate. Flow can be controlled by setting the pressure differential, the resistance or both. These can be actively controlled but such systems require active pressure sources (e.g. pumps) or resistors (e.g. valves) often with feedback loops based on flow sensors.

Controlling flow completely passively, however, is more difficult. Passive flow resistors (e.g. manual or fixed valves, orifice plates, etc.) are commonly used to control flow but their accuracy are dependent on maintaining a fairly constant pressure. This is typically accomplished with a large reservoir of fluid, (relative to the volume of fluid to be delivered) with stored potential energy that is constant (e.g. elevated tank). A major limitation of this passive variable resistor design is that it is structurally linked to the infusion device and its design is dependent on the device. Perhaps more importantly, its specifications are dependent on the initial conditions, specifically the initial pressure, and the specific trajectory of the pressure for that specific device. The functionality of passive variable resistors would be greatly enhanced and available to a broader set of applications if its design and structure were independent of the pressure source and fluid reservoir and that its resistance was simply a function of the instantaneous pressure difference P at least over a specified range.

One example of a fluid transfer application is patient infusions. Infusions remain ubiquitous in healthcare spanning a wide range of conditions, substances, access sites and venues. Despite advances in oral and other drug delivery modes (e.g. transdermal, inhaled) many critical therapies still require intravenous (IV) infusion. It is estimated that one million infusions are administered per day in the United States. Over 90% of hospitalized patients receive an IV infusion. Infused substances can include drugs (e.g. antibiotics, chemotherapy, pain medications, local anesthetics, vasoactive agents, biologics), fluids (e.g. crystalloids, colloids, parenteral nutrition) and blood products (e.g. red cells, plasma, platelets). These substances are typically infused as (1) a single bolus volume (a few ml to several liters) over a limited time period (e.g. minutes to hours) or (2) a continuous infusion delivered a fixed or titrated rate (typical range 0.1 ml to 5 ml per minute)

Infusions can be administered through a variety of routes, most commonly intravenous but also intraarterial, subcutaneous, intrapleural, intraarticular, epidural and intrathecal, intraperitoneal and intramuscular. A wide variety of catheters are available to facilitate infusions in through these various routes. Although traditionally, infusions have been administered in hospital settings, an increasing number of patients are receiving infusions in ambulatory infusion centers and at home. Because these latter settings have fewer, less skilled clinical personnel, only certain infusions are deemed to be safe there such as intravenous antibiotics, certain chemotherapeutic agents, local anesthetics for postoperative pain control and certain narcotic pain medications.

Healthcare infusions are generally driven by relatively stale technologies such as gravity, active displacement electric pumps or non-electric disposable elastomeric pumps. All three have well known disadvantages. Gravity driven infusions have low capital and disposable costs but require careful monitoring by a nurse, are not very accurate, limit patient mobility and have no patient safety features. Electric pumps are accurate (±3%), have built in safety features of debatable efficacy but are expensive, bulky, susceptible to human factors and limit mobility. Additionally, infusion pump errors are a serious ongoing problem and represent a large share of the overall human and economic burden of medical errors. Electronic infusion pumps have become expensive and high maintenance devices, which have been plagued in recent years by recalls due to serious software and hardware problems. These pumps are designed for fine adjustments of infusions in complex patients, such as those in a critical care setting, and their use for routine infusions is technologic overkill. In terms of outpatient infusions. Disposable pumps are convenient and fairly inexpensive but have no patient safety features and can be highly inaccurate (±15-40%) and are therefore unsuitable for use with medications where flow accuracy is critical, such as chemotherapeutic. The FDA's MAUDE database includes numerous reports of complications and even deaths resulting from disposable infusion pump flow inaccuracies.

The landmark 1999 Institute of Medicine report, "To Err is Human" (REF), attributed 40-100,000 deaths per year in the U.S. to medical errors. Medication errors, 40% of which are serious, life-threatening or fatal, are the most common medical error and cost the health care system billions of dollars per year. Intravenous medication errors are the most common medication error and over 35% of these are related to infusion pumps. Studies have shown that despite progressively feature-laden "smart pumps", human factors, software and hardware issue continue to contribute to serious errors (REF). The FDA's MAUDE Adverse Event reporting system contain numerous examples of serious injury and death related to infusion pump errors, both electric and disposable. In the past 4 years over 600,000 electric infusion pumps from the two leading manufacturers have been recalled over major software and hardware problems leading patient injury and death.

SUMMARY

There is a need for improvements for safety and efficiency of fluid transfer devices, such as for example, for healthcare infusions. The present disclosure is directed toward further solutions to address this need, in addition to having other desirable characteristics. Specifically, the present disclosure provides a passive variable flow resistor that can be implemented to simplify the infusion process to a point where it is "plug and play", and can thus, be initiated by the patient themselves or a low-skill health care provider.

In accordance with example embodiments of the present invention, variable flow resistor device is provided. The device includes a fluid chamber having an input and an output, a reduced cross-sectional area within the chamber between the input and the output, and a moveable element designed to move along the reduced cross-sectional area to define a fluid flow channel between the reduced cross-sectional area and the moveable element, the fluid flow channel providing a substantially consistent flow rate independent of a pressure differential between a fluid source and a point of delivery at the output.

In accordance with aspects of the present invention, the reduced cross-sectional area is defined by a restrictor positioned within the chamber. The restrictor can include a symmetrical shaped, asymmetrical shaped, or eccentrical shaped structure, or a combination thereof extending from a wall of the chamber. The restrictor can have at least one eccentrical cutout. The moveable element can be shaped to substantially fill the reduced cross-sectional area defined by the restrictor creating the fluid flow channel through the at least one eccentrical cutout. A minimum length and a maximum length of the fluid flow channel can be defined by a minimum overlap and a maximum overlap between the moveable element and the restrictor. The chamber can include one or more stops to establish at least one of the minimum overlap or maximum overlap between the moveable element and the restrictor. The one or more stops can be adjustable to modify the at least one of the minimum overlap or maximum overlap between the moveable element and the restrictor.

In accordance with aspects of the present invention, the moveable element is a piston. The device can further include at least one biasing member coupled to at least one end of the moveable element and at least one end of the chamber. The biasing member can include at least one of a spring, an elastomer liner, an accordion, an elongating element, or a combination thereof. The device can further include a flow indicator designating whether there is an active flow through the device. The moveable element can be designed to surround at least a portion of and move over the restrictor.

In accordance with example embodiments of the present invention, a system for implementing a controlled flow rate is provided. The system includes a fluid source and a variable flow resistor device being in fluid communication with the fluid source. The variable flow resistor device includes a fluid chamber having an input for receiving a fluid from the fluid source and having an output, a reduced cross-sectional area within the fluid chamber between the input and the output, and a moveable element designed to move along the reduced cross-sectional area to define a fluid flow channel between the reduced cross-sectional area and the moveable element, the fluid flow channel providing a substantially consistent flow rate independent of a pressure differential between a fluid source and a point of delivery at the output and a pathway to direct fluid from the fluid source through the fluid chamber and to a point of delivery.

In accordance with aspects of the present invention, the reduced cross-sectional area is defined by a restrictor positioned within the chamber. The variable flow resistor device can automatically adjust its resistance (R) to the input pressure difference ($\Delta P$) from the fluid source so that a flow through the output of the variable flow resistor device is constant ($Q_o$). The system can further include at least one biasing member coupled to at least one end of the moveable element and at least one end of the chamber, wherein the biasing member includes at least one of a spring, an elastomer liner, an accordion, an elongating element, or a combination thereof. The system can further include a flow indicator designating whether there is an active flow through the device.

In accordance with example embodiments of the present invention, a method for delivering a constant fluid flow is provided. The method includes providing variable flow resistor. The variable flow resistor having a fluid chamber having an input and an output, a reduced cross-sectional area within the chamber between the input and the output, and a moveable element designed to move along the reduced cross-sectional area to define a fluid flow channel between the reduced cross-sectional area and the moveable element, the fluid flow channel providing a substantially consistent flow rate independent of a pressure differential between a fluid source and a point of delivery. The method also including coupling the variable flow resistor to a fluid source via the input of the fluid chamber and allowing the variable flow resistor to control pressure at the outlet of the fluid chamber to deliver fluid from the fluid source to the point of delivery at a consistent flow rate. In accordance with aspects of the present invention, the variable flow resistor modifies a variable inlet pressure to a consistent outlet pressure.

BRIEF DESCRIPTION OF THE FIGURES

These and other characteristics of the present disclosure will be more fully understood by reference to the following detailed description in conjunction with the attached drawings, in which:

FIGS. 3A and 3B are example cross-sectional side views of a variable flow resistor, in accordance with some embodiments of the present disclosure;

FIGS. 4A and 4B are example cross-sectional side views of a variable flow resistor, in accordance with some embodiments of the present disclosure;

FIGS. 5A, 5B, 5C, and 5D are example cross-sectional end views of a variable flow resistor, in accordance with some embodiments of the present disclosure;

FIG. 8D is an example chart showing effect of the variable flow resistor in FIGS. 8A-8C, in accordance with some embodiments of the present disclosure;

FIGS. 13B, 13C, and 13D are example cross-sectional end views of a variable flow resistor in FIG. 13A, in accordance with some embodiments of the present disclosure;

DETAILED DESCRIPTION

Figure 1A:
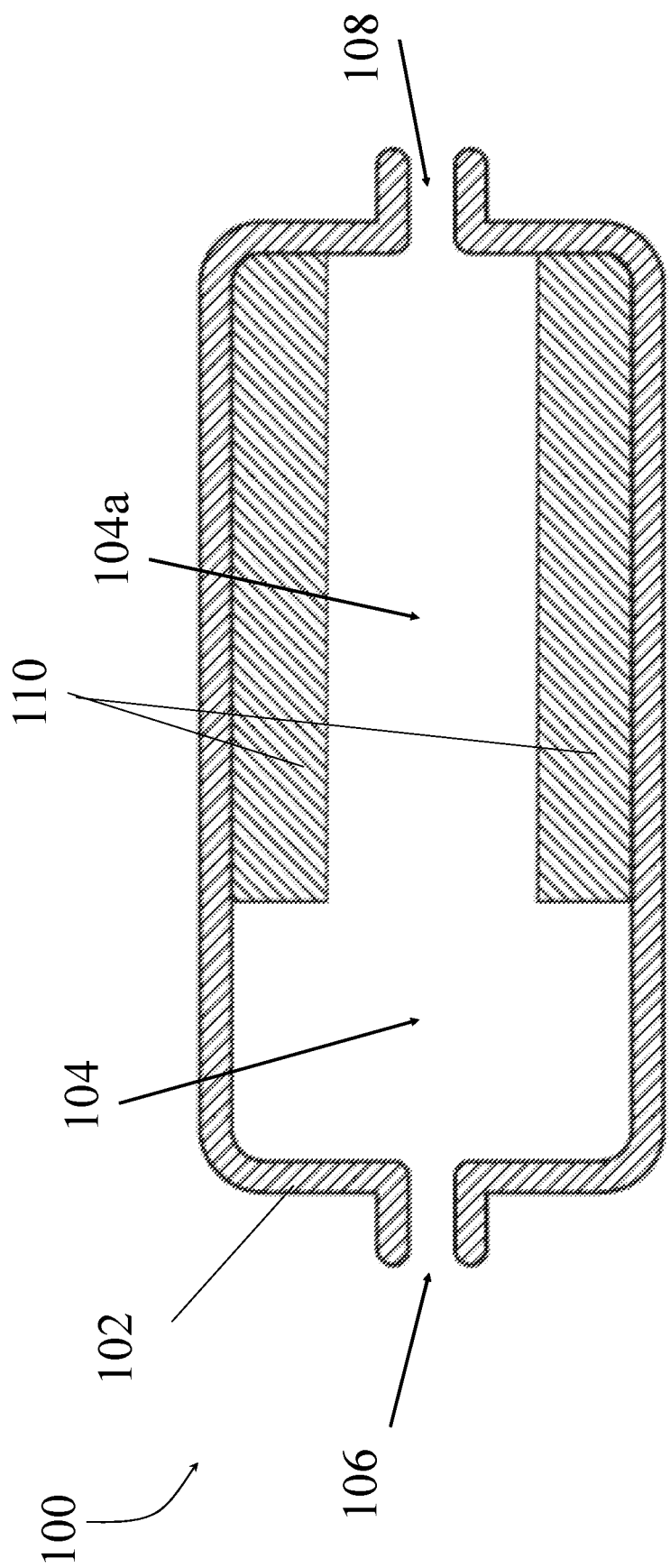
FIGS. 1A and 1B are example cross-sectional side views of a variable flow resistor, in accordance with some embodiments of the present disclosure.

An illustrative embodiment of the present disclosure relates to a passive variable flow resistor. The variable flow resistor can be configured to create a pressure differential between an input and a desired output using flow relationships defined by the geometric properties of its components and the mechanical properties of a moveable element positioning mechanism within a pressure differential operating range. The moveable element can be used in conjunction with specific geometric properties of a flow chamber to create a customized flow channel with a constant cross-sectional area. As the moveable element is positioned within the cross-sectional area, a flow rate through that area can be consistently regulated regardless of the change in input flow pressure or input flow rate. For example, the elements of the present invention can be used to regulate, modify, etc. a flow output from the device to a desired uniform flow rate output, regardless of the input flow rate, pressure, etc. In other words, the present invention can be used to receive a variable input flow and regulate, modify, etc. the flow to an automatic, reliable, consistent desired output flow.

In some embodiments, the variable flow resistor can include a piston as the moveable element coupled to a biasing mechanism, such as a spring, to create a reduced flow channel. The biasing mechanism can act as a positioning mechanism with linear elastic properties (obeys Hooke's Law such as conventional springs, elastomeric bands, etc.), to provide a custom relationship between the pressure differential and flow rate is one of a consistent flow rate, independent of the pressure differential. In other words, using this combination, the elements in combination functions as a consistent flow rate variable resistor.

In an example operation, as each side of the piston is exposed to the input and outlet pressures respectively, the force of the pressure difference on the piston can be counterbalanced by the force of the biasing mechanism. The balance of these forces determines the piston's position, which interacts with a fluid channel to create a reduced cross-sectional flow channel that can control the resistance of the flow through the fluid channel. Thus, implementation of the variable flow resistor enables fluid flows from a fluid reservoir through the flow channel to exit into a receptacle at a controlled consistent rate regardless of changes to the input pressure and/or an input flow rate that is higher/lower than the desired output flow rate. The present disclosure is not limited to use of a piston and biasing mechanism and can use any combination of elements to manipulate a flow channel to modify an input flow rate to remain constant.

The design of the variable flow resistor of the present disclosure ensures that a fluid flow can only flow at a designated flow rate regardless of an input flow rate into the resistor, preventing complications associated with infusions running too slow or too fast. The variable flow resistor device can be incorporated into any combination of systems that require a consistent flow rate of fluid from a fluid source to a fluid receptacle. In one example, the variable flow resistor can be implemented within an intravenous infusion set and disposable infusion pumps for routine inpatient and outpatients infusions respectively. Implementation into infusion sets will permit hospitals to return to gravity based infusions and eliminate expensive electric infusion pumps for most inpatient infusions. The accuracy of the variable flow resistor incorporated into a disposable infusion pump can also allow outpatient administration of a broader range of drugs, thereby significantly expanding the addressable market.

FIGS. 1A through 20B, wherein like parts are designated by like reference numerals throughout, illustrate an example embodiment or embodiments of improved operation for a variable flow resistor and methods of use, according to the present disclosure. Although the present disclosure will be described with reference to the example embodiment or embodiments illustrated in the figures, it should be understood that many alternative forms can embody the present disclosure. One of skill in the art will additionally appreciate different ways to alter the parameters of the embodiment(s) disclosed, such as the size, shape, or type of elements or materials, in a manner still in keeping with the spirit and scope of the present disclosure.

The systems and methods of the present disclosure can be implemented to create a variable flow resistor (VFR) 100 for controlling a flow of fluid therethrough. Referring to FIGS.

Figure 2A:
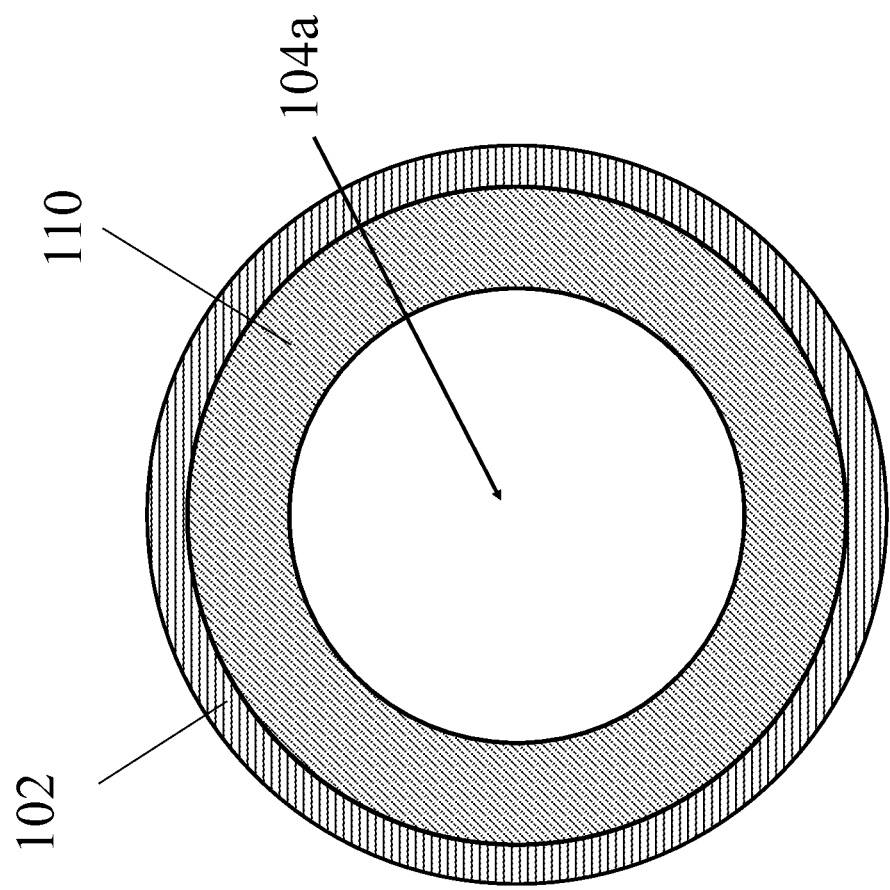
FIGS. 2A, 2B, and 2C are example cross-sectional end views of a variable flow resistor, in accordance with some embodiments of the present disclosure.
Figure 2B:
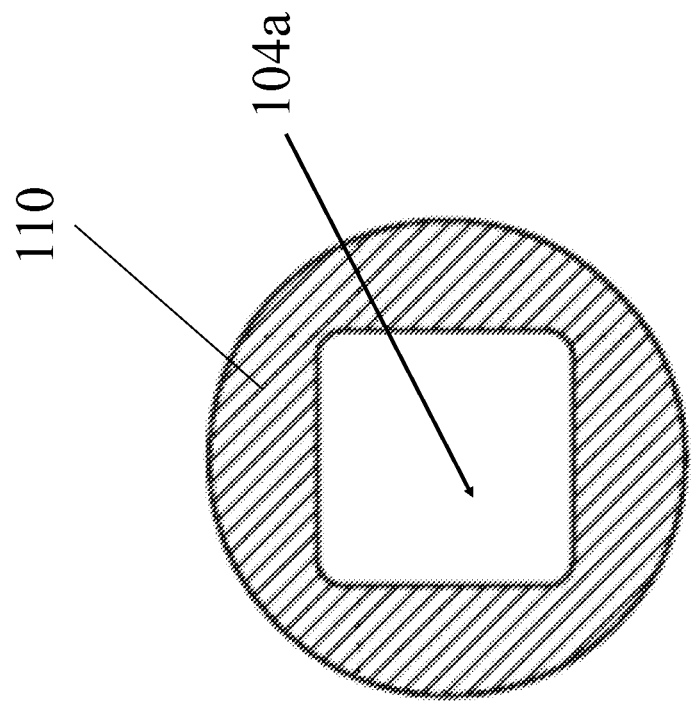
Figure 2B:
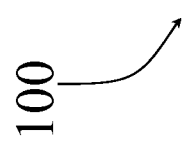

1A and 1B, in some embodiments, the VFR 100 can include a flow chamber 102 designed to receive, contain, and output a fluid flow. The flow chamber 102 can include a cavity or channel 104 accessible by and in fluid communication with an input 106 and an output 108, in an embodiment, and is defined by sidewalls of the VFR 100. The flow chamber 102 can include any combination of interior and exterior shapes, depending on the desired function. For example, the flow chamber 102 can be a generally cylindrical, rectangular, polygonal, etc. shape and can be elongated in length. Similarly, the exterior of the flow chamber 102 does not need to be the same shape as the interior of the flow chamber 102, for example, as shown in FIG. 2B.

In some embodiments, the input 106 and output 108 can be located on opposing ends of the chamber 102. For example, the input 106 can be located at a proximal end of the VFR 100 and the output 108 can be located at a distal end of the VFR 100. The input 106 and output 108 can be located at any combination of locations of the chamber 102 without departing from the scope of the present disclosure. For example, the input 106 and/or output 108 can be located on the top, bottom, side, etc. of the chamber 102. Similarly, the input 106 and an output 108 can be sized, dimensioned, and with any combination of coupling types designed to receive input and output lines requiring flow control. For example, the input 106 and output 108 can be sized and dimensioned to receive convention intravenous (IV) lines to input and output fluid through the VFR 100 at a desired controlled rate. Although the input 106 and output 108 are depicted along a same plane and similar size, the input 106 and 108 can vary in location, size, hookups, etc.

Figure 1B:
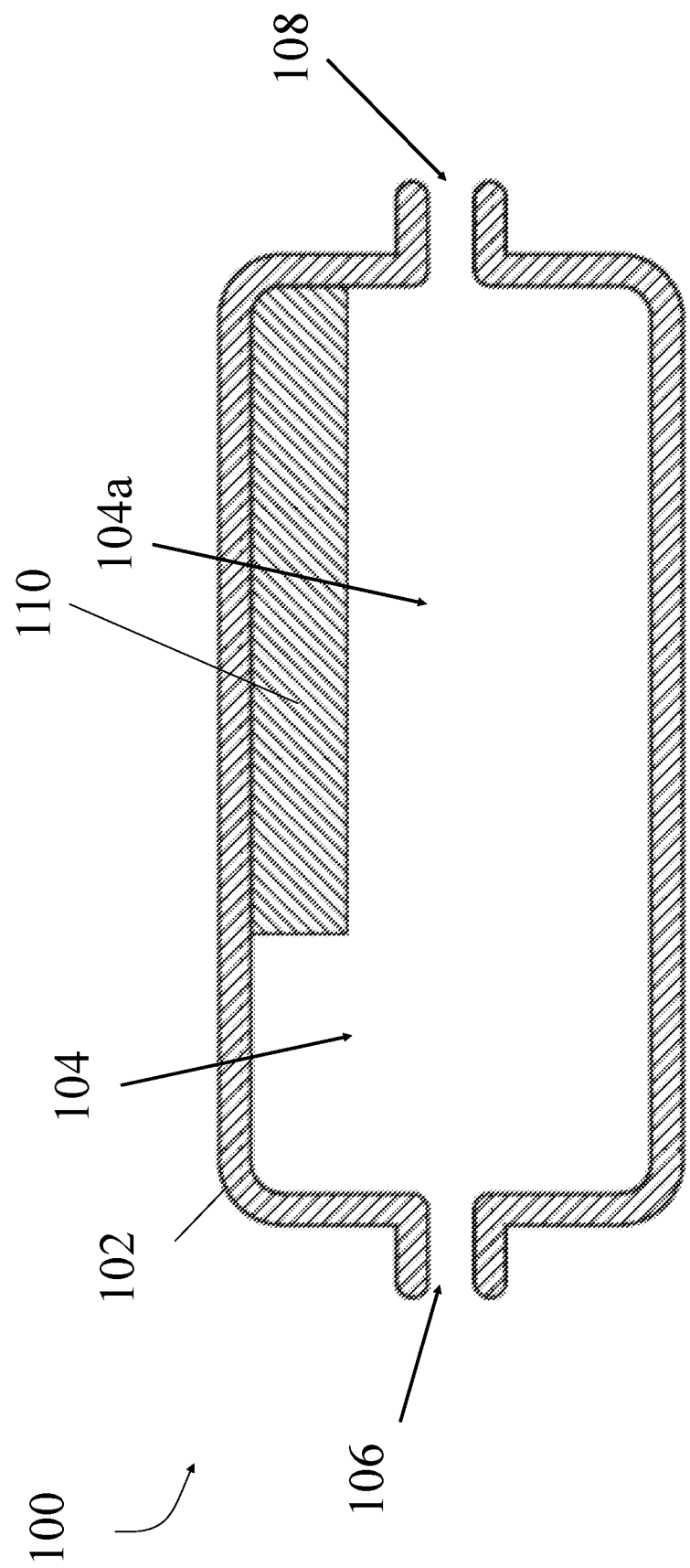

Continuing with FIGS. 1A and 1B, in some embodiments, an inner surface of the flow chamber 102 of the VFR 100 can include at least one geometric shape extending from the inner surface of the chamber 102 toward the channel 104. The at least one geometric shape can be a member, design, or a combination thereof that can be provided to decrease, disrupt, or effect the flow of fluid through the chamber, for example, to restrict a volume of fluid flow through a reduced cross-sectional area (CSA) 104a, partially created by the geometric shape, over a period of time. This geometric shape can be a restrictor, an obturator, or any flow restrictor 110 such that a normal flow through the chamber 102 is modified by the presence of the restrictor 110. The restrictor 110 can be a part of the chamber 102 itself or a separate component inserted within and coupled to the chamber 102. The restrictor 110 can be symmetrical, asymmetrical, and located at any position within the chamber 102 to impart a particular shape on the channel 104. For example, the restrictor 110 can be located near the proximal end, distal end, or the mid-section of the channel 104. The restrictor 110 can be any combination of geometric shapes, for example, the restrictor 110 can be a protrusion that conforms the inner surface of the VFR 100 (i.e., circumferentially place about the inner surface of the VFR 100) (e.g., a hollow cylinder shape). The restrictor 110, in some embodiments, can be uniform in shape, for example, the restrictor 110 can be same geometric around substantially an entire inner circumference of the channel 104 to create a symmetrical cross-section, as depicted in FIG. 1A. Alternatively, the restrictor 110 can be a varied shape at different portions within the channel 104 to create an asymmetrical or eccentrical cross-section, as depicted in FIG. 1B, or a combination thereof.

The restrictor 110 within the chamber 102 can be configured to create a reduced cross-sectional area (CSA) 104a within the flow channel 104. The CSA 104a can be sized and shaped to be meaningfully reduced over a predetermined length to affect a flow rate through the channel 104. The amount of the reduction and the predetermined length of the reduced cross-sectional area 104a can vary based on the desired application and desired flow rate output. In some embodiments, the restrictor 110 can be a separate material from the chamber 102 configured to further affect the flow of fluid through the reduced cross-sectional area. The restrictor 110 can also be constructed from the same material and/or be a thicker portion of the chamber 102 itself. In some embodiments, the reduced cross-sectional area 104a created by the restrictor 110 can be a decreasing area or an increasing area from the proximal end of the restrictor 110 to the distal end of the restrictor 110.

As would be appreciated by one skilled in the art, the VFR 100 and the components thereof, can be constructed from any combination of materials using any combination of methods known in the art, depending of the desired application. For example, they can be constructed from any combination of metal, plastics, synthetic materials, etc.

Still referring to FIGS. 1A and 1B, example cross-sectional side views of variable flow resistors 100 are depicted. FIG. 1A shows an example cross-sectional side view of the VFR 100 including a circumferentially symmetrical restrictor 110 situated about the inner surface of the VFR 100 at a distal end of the channel 104 to form a reduced cross-sectional area 104a, for example, as shown in FIG. 2A. FIG. 1B shows an example cross-sectional side view of the VFR 100 including an asymmetrical/eccentrical restrictor 110 at a distal end of the channel 104 to form a decreased CSA 104a. In contrast to the symmetrical shape of FIG. 1A, such an asymmetrical/eccentrical restrictor 110 in FIG. 1B would not extend around substantially an entire circumference of the chamber 102 like the one shown in FIG. 2A.

Figure 2C:
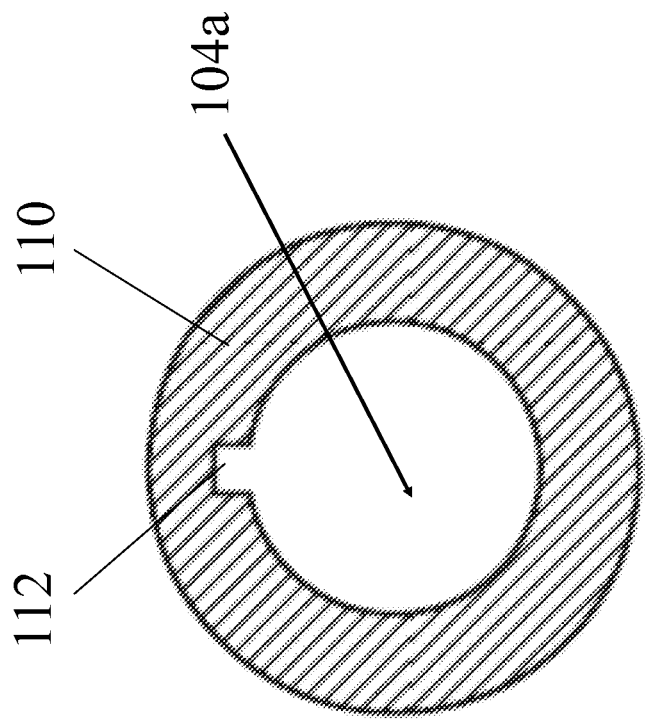

Referring to FIGS. 2A-2C, example cross-sectional end views of example variable flow resistors 100 are depicted. FIG. 2A shows an example cross-sectional end view of the VFR 100 including a cylindrical chamber 102 with a symmetrical circular restrictor 110 creating a tubular decreased CSA 104a of the channel 104. FIG. 2B shows an example cross-sectional end view of a restrictor 110 for insertion within a cylindrical chamber 102. The example restrictor 110 in FIG. 2B is a symmetrical restrictor 110 extending from the interior of the chamber 102 to form a rectangular shaped decreased CSA 104a. FIG. 2C shows an example cross-sectional end view of a restrictor 110 for insertion within a cylindrical chamber 102. The example restrictor 110 in FIG. 2C is an asymmetrical/eccentrical restrictor 110 extending from the interior of the chamber 102 to form a tubular decreased CSA 104a with an eccentric cutout 112. As would be appreciated by one skilled in the art, the shapes of the chamber 102 and the restrictor 110 can include any combination of shapes and sizes with or without cutouts 112 to form any combination of sized and shaped decreased CSA 104a. Similarly, the inner surface of the chamber 102 and the restrictor 110, or portions thereof, can include any combination of smooth, textured, and patterned material and can be constructed from any material known in the art. In some embodiments, material and the inner surface for each of the chamber 102 and the restrictor 110 can be selected to instill a desired modifying effect to a flow or fluid across the restrictor 110 and through the chamber 102.

Referring now to FIG. 3A, in some embodiments, the VFR 100 can include at least one moveable element 120 located within the chamber 102. The moveable element 120 can be coupled to at least one end of the chamber 102 and can be configured to traverse at least within the chamber 102. For example, the moveable element 120 can be a piston. In some embodiments, moveable element 120 can include a shaft (not depicted) coupled to the chamber 102 that allows for movement within the chamber 102. The moveable element 120 can be sized and shaped to fit within but not entirely occupy the CSA 104*a* created by the restrictor 110 such that an overlap of the two components creates a flow channel 104*b*. The flow channel 104*b* can limit the amount of area that a fluid can flow through the chamber 102 to create a modified flow rate in which a fluid entering the chamber 102 (via input 106) is capable of exiting the chamber 102 (via output 108). In other words, depending on the size and length of the flow channel 104*b*, the fluid can only flow through at a particular rate in which the channel 104*b* can accommodate, thus providing a means to modify a flow rate through the variable flow resistor 100 by modifying characteristics (size, length, etc.) of the flow channel 104*b*. Because the moveable element 120 can be positioned to occupy only a portion of the CSA 104*a* created by the restrictor 110, a reduced flow channel 104*b* can be created in the remaining area of the CSA 104*a* through which fluid can flow. In some embodiments, the moveable element 120 can be an object made of any combination of solid material or semisolid material.

In some embodiments, the moveable element 120 can have a length less than the overall length of the internal chamber 102 and a cross-sectional area that is less than the cross-sectional area of the decreased CSA 104*a* created by the restrictor 110, such that the moveable element 120 can traverse freely within the CSA 104*a*. The moveable element 120 can be configured to traverse within the chamber 102 and within at least a portion of the decreased CSA 104*a*. The moveable element 120 can be configured to traverse within the decreased CSA 104*a*, for example, sharing a central axis or from an offset vertical positioning within the decreased CSA 104*a*. The shape of the moveable element 120 can include any combination of shapes that fit and traverse within the decreased CSA 104*a* and does not need to be the same shape as the chamber 102 or the cross-sectional shape of the decreased CSA 104*a*. The outer surface of the moveable element 120, or portions thereof, can include any combination of smooth, textured, and patterned material and can be constructed from any material known in the art. In some embodiments, material and the outer surface of the moveable element 120 can be selected to instill a desired modifying effect to a flow or fluid over the moveable element 120 and through the chamber 102.

Figure 3B:
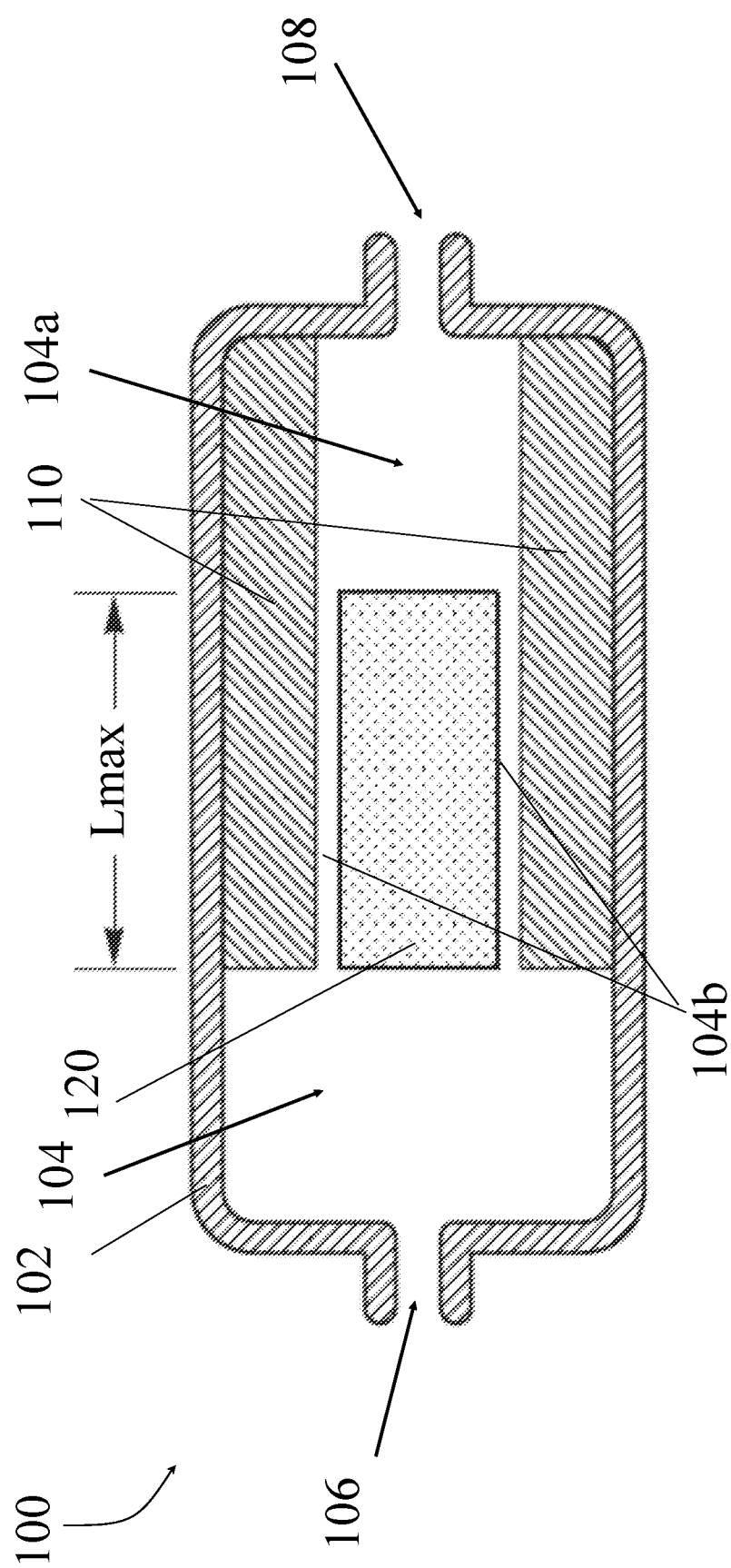

Referring to FIGS. 3A and 3B, example cross-sectional side views of variable flow resistors 100, including a moveable element 120 therein, are depicted. FIG. 3A shows an example cross-sectional side view of the VFR 100 including a symmetrical restrictor 110 extending from the mid-section of the chamber 102 to a distal end of the chamber 102 to form a decreased CSA 104*a*. FIG. 3A also depicts a moveable element 120 located at a first position partially within the decreased CSA 104*a*. The combination of the moveable element 120 located within at least a portion of the decreased CSA 104*a* creates a flow channel 104*b*. For example, the flow channel 104*b* can be defined by the inner surface of the restrictor 110 of the chamber 102 and the outer surface of the moveable element 120 where they overlap. FIG. 3A further depicts how the fluid flow enters the input 106, flows through the CSA 104*a* and out the output 108.

Referring to FIG. 3B, in some embodiments, the moveable element 120 can be sized and positioned such that the length of the moveable element 120 substantially or fully overlaps (e.g., Lmax) with the inner surface of the restrictor 110 to create a maximum length flow channel 104*b*. This is in contrast to FIG. 3A, which shows an example where the outer surface of the moveable element 120 partially overlaps (e.g., L) with the inner surface of the restrictor 110 to create a partial length flow channel 104*b*. The maximum length (Lmax) flow channel 104*a* of FIG. 3B will provide more resistant force to a fluid flow through the chamber 102 than the partial length (L) flow channel 104*a* of FIG. 3A.

Thus, the length of the region of overlap between the moveable element 120 and the restrictor 110 can define a length of the flow channel 104*b*, which can be adjusted by repositioning the moveable element 120 within the restrictor 110 to adjust a resistant force to the fluid flowing therethrough. For example, the moveable element 120 can be positioned further into the restrictor 110 to create a greater length of overlap to lengthen the flow channel 104*b* and create greater resistance or the moveable element 120 can be withdrawn from the restrictor 110 to create a lesser length of overlap to shorten the flow channel 104*b* to create less resistance. The moveable element 120 can be removed from the restrictor 110 substantially or entirely to eliminate the flow channel 104*b* for an unmodified flow through the flow through channel 104. Any combination of restrictor 110 lengths and moveable element 120 lengths can be used to create different Lmin and Lmax overlaps without departing from the scope of the present disclosure.

Referring to FIG. 4A, in some embodiments, the chamber 102 can include one or more stops 122 to establish at least one of a minimum or maximum movement/position of the moveable element 120 within the chamber 102. FIG. 4A depicts two stops 122 extending from the internal proximal end of the chamber 102. The stops 122 in FIG. 4A, in some embodiments, establish a minimum distance in which the moveable element 120 can traverse toward the proximal end of the chamber 102. Because, in FIG. 4A, the moveable element 120 is sized such that it still overlaps with the restrictor 110 when in contact with stops 122 at the proximal end of the chamber 102, a minimum overlap (Lmin) is established.

Figure 4B:
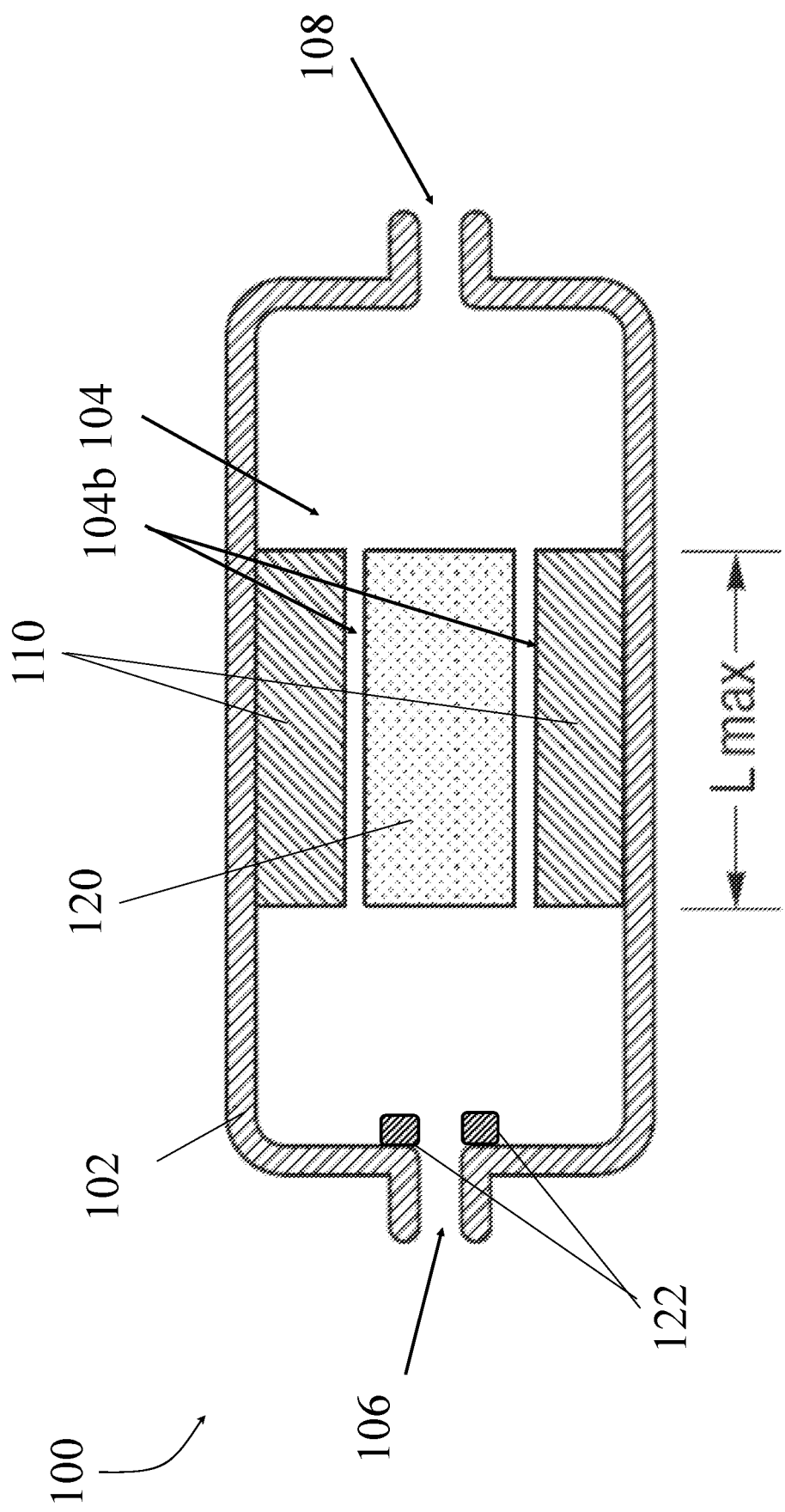

Referring to FIG. 4B, in some embodiments, the moveable element 120 can be sized and positioned to overlap with the restrictor 110 for substantially an entirety of the length of the moveable element 120. Because, in FIG. 4B, the moveable element 120 is sized and positionable such that it can substantially or fully overlap with the restrictor 110, a maximum overlap (Lmax) is established. To establish a maximum overlap of a length of the moveable element 120 (as depicted in FIGS. 3B and 4B), the length of the restrictor 110 must be greater than or equal to the length of the moveable element 120 and the moveable element 120 must be extendable into the CSA 104*a* to establish that full overlap. Once a maximum overlap is achieved, further movement of the moveable element 120 in the distal direction will not significantly modify the resistance of the flow channel 104*b*, unless the moveable element 120 extends beyond the CSA 104*a*. In some embodiments, the maximum overlap may be less than the length of the moveable element 120. The minimum and maximum overlap length can be modified based on design of the variable flow resistor 100, including but not limited to a length of the restrictor 110, a length of the moveable element 120, stops 122 within the chamber 102, the chamber 120 length, piston lengths, biasing mechanism lengths, etc., or any combination thereof.

As illustrated in FIGS. 4A and 4B, an amount of overlap between the moveable element 120 and the restrictor 110 can create a channel 104*b* with a length anywhere between and including a minimum length (Lmin) and maximum length (Lmax). Lmin can be determined by the most proximal possible position of the moveable element 120, which in some embodiments is limited by a stop 122, the proximal end wall of the fluid chamber 102, or any other structural element. The Lmax can be the smaller of the length of the moveable element 120 and the length of the restrictor 110 which represents the maximum overlap between the moveable element 120 and the restrictor 110, unless the length of the restrictor 110 and moveable element 120 are at least equal and the moveable element 120 is free to move in position for substantially an entire overlap, as depicted in FIG. 4B. The Lmax can also be limited to another value by limiting an amount of overlap of the moveable element 120 and the restrictor 110, for example, by implementing a stop 122 on the distal end of the chamber 102 or limiting travel of the moveable element 120 via a piston arm, spring, etc. attached to both the moveable element 120 and the chamber 102. Regardless of configurations, the length of overlap (L) will affect the flow rate through the flow channel 104b. For example, a flow through an overlap of Lmin may reduce an input flow to a lesser extent than through an overlap of Lmax. Similarly, the geometric relationship between the moveable element 120 and the CSA 104a can provide different effects to the fluid channel 104b. Any combination of restrictor 110 lengths, moveable element 120 lengths, and stop 122 lengths and can be used to create different Lmin and Lmax overlaps without departing from the scope of the present disclosure.

Figure 5A:
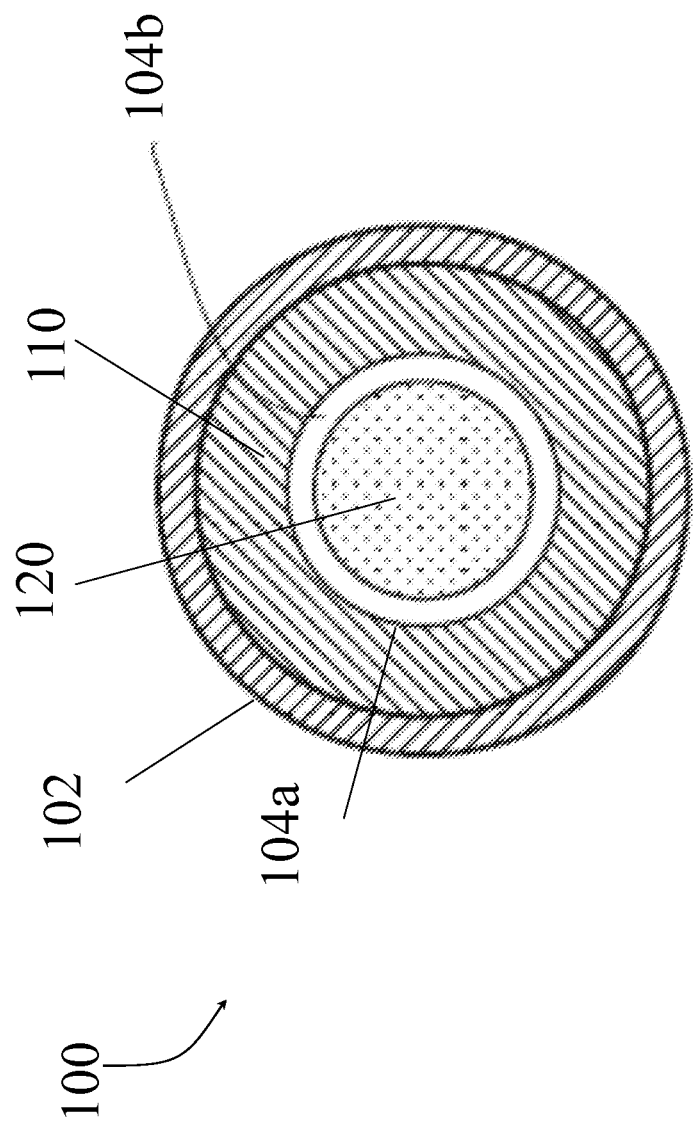

Referring to FIGS. 5A-5D, in some embodiments, the flow channel 104b can be created using different combinations of geometries for the chamber 102, restrictor 110, and the moveable element 120. Different flow channel 104b configurations, shapes, designs, etc. can be used to create unique flow characteristics through the flow channel 104b and the overall operation of the variable flow resistor 100. FIGS. 5A-5D depict example cross-sectional end views of variable flow resistors 100 including a restrictor 110 with moveable element 120 positioned therein. FIG. 5A shows an example cross-sectional end view of the VFR 100 including a circular chamber 102 with a symmetrical circular restrictor 110 extending from the interior of chamber 102 and a moveable element 120 centrally located within the channel 104 to create a tube-shaped flow channel 104b.

Figure 5B:
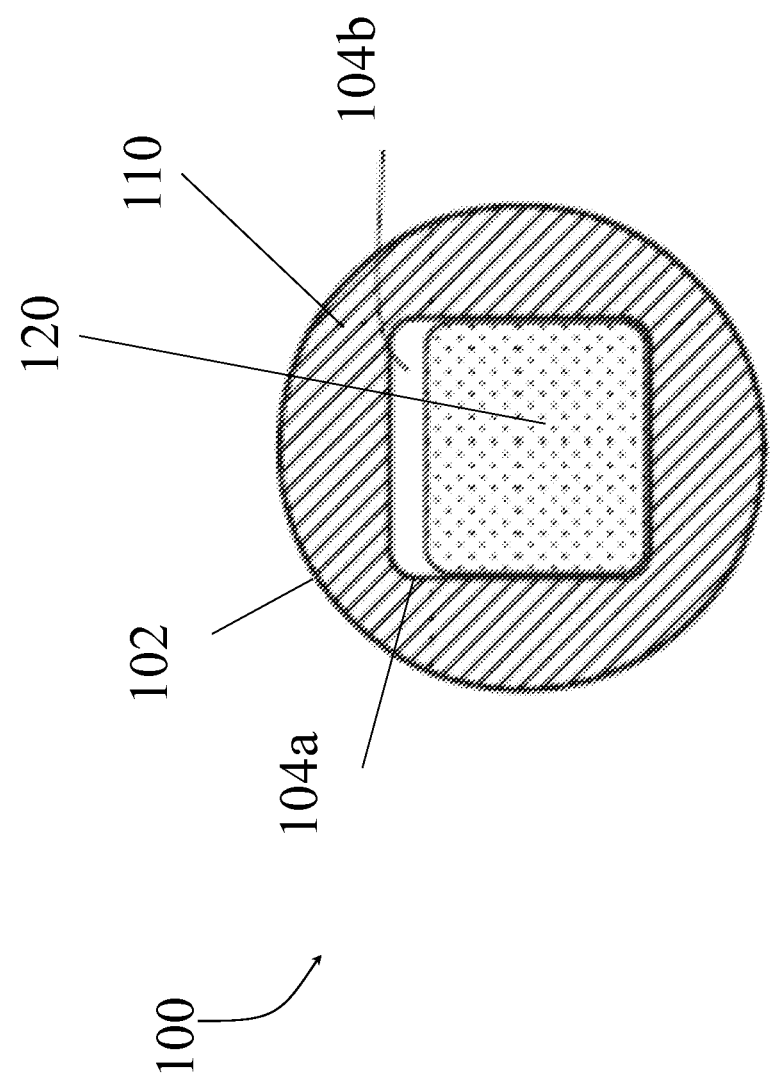

FIG. 5B shows an example cross-sectional end view of the VFR 100 including a circular chamber 102 with a symmetrical restrictor 110 extending from the interior of the chamber 102 to form a rectangular decreased CSA 104a. The VFR shown 100 in FIG. 5B also includes a rectangularly shaped moveable element 120 located within the channel 104 with an offset positioning from the center of the CSA 104a to be adjacent to three of the four walls of the restrictor 110. As shown in FIG. 5B, a portion of the inner surface of the restrictor 110 and a portion of the outer surface of the moveable element 120 may be in contact resulting in a flow channel 104b created where the surfaces are not in contact (e.g., top of the moveable element 120), resulting in a flow channel 104b which takes on a slot-like configuration over a limited portion of the perimeter, in contrast to a full annular flow channel 104b provided in FIG. 5A. In some embodiments, when adjacent to the restrictor 110, the moveable element 120 can include or otherwise be encased by one or more seals, gaskets, etc. in contact with at least a portion of an inner wall of the restrictor 110 and/or the chamber 102 to maintain a fluid seal such that fluid can only flow from the proximal end of the channel 104 to the distal end of the channel 104 through the flow channel 104b. In other words, the seal can prevent fluid communication between the proximal and distal portions of the chamber 102 channel 104, except through a flow channel 104b.

FIG. 5C shows an example cross-sectional end view of the VFR 100 including a circular chamber 102 with an asymmetrical/eccentrical restrictor 110 extending from the interior of the chamber 102 to form a tubular decreased CSA 104a with an eccentric cutout 112. The VFR 100 shown in FIG. 5C also includes a circular or cylindrically shaped moveable element 120 centrally located within the channel 104 and adjacent to the CSA 104a. As shown in FIG. 5C, the inner surface of the restrictor 110 and the outer surface of the moveable element 120 may be in contact, except where the eccentric cutout 112 in the restrictor 110 is located, resulting in a flow channel 104b, which takes on a slot-like configuration. In some embodiments, when adjacent to the restrictor 110, the moveable element 120 can include or otherwise be encased by one or more seals, gaskets, etc. in contact with at least a portion of an inner wall of the restrictor 110 and/or the chamber 102 to maintain a fluid seal. The seal can prevent fluid communication between the proximal and distal portions of the chamber 102 channel 104, except through a flow channel 104b.

Figure 5D:
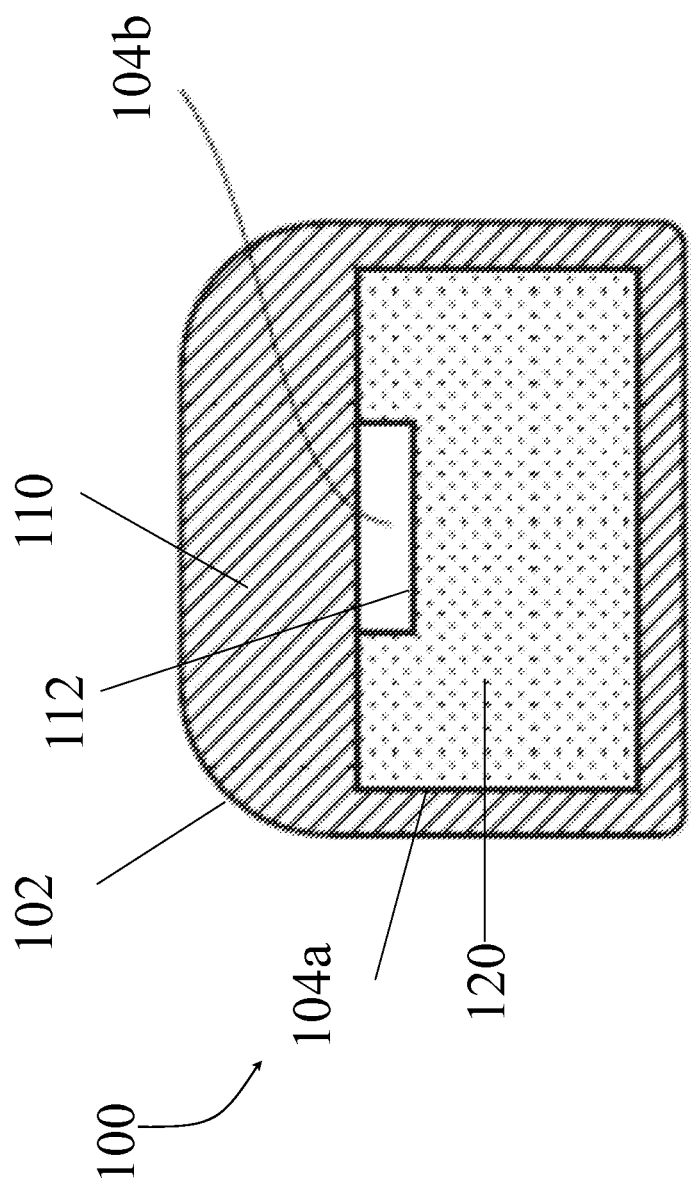

In some embodiments, the moveable element 120 can include a cutout 112 for creating a flow channel 104b when the moveable element 120 overlaps with the restrictor 110, for example, as shown in FIG. 5D. FIG. 5D shows an example cross-sectional end view of the VFR 100 including a substantially rectangular chamber 102 with an asymmetrical/eccentrical restrictor 110 extending from the interior of the chamber 102 to form a substantially rectangular decreased CSA 104a. The VFR 100 shown in FIG. 5D also includes a eccentrical rectangularly shaped moveable element 120 cross-sectionally aligned with the decreased CSA 104a. As shown in FIG. 5D, the inner surface of the restrictor 110 and the outer surface of the moveable element 120 may be in contact, except where the eccentric cutout 112 in the moveable element 120 is located, resulting in a flow channel 104b which takes on a slot-like configuration. In some embodiments, when adjacent to the restrictor 110, the moveable element 120 can include or otherwise be encased by one or more seals, gaskets, etc. in contact with at least a portion of an inner wall of the restrictor 110 and/or the chamber 102 to maintain a fluid seal. The seal can prevent fluid communication between the proximal and distal portions of the chamber 102 channel 104, except through a flow channel 104b.

As would be appreciated by one skilled in the art, FIGS. 5A-5D are for example purposes only and the chamber 102, restrictor 110, moveable element 120, and any cutouts 112 can include any combination of shapes and sizes to form any combination of sized and shaped decreased CSA 104a and flow channel 104b. For example, any of the chamber 102, restrictor 110, and moveable element 120 can be spiral cut, multi-pitch spiral cut, trumpet cut, etc. Similarly, any eccentric cutouts within the chamber 102, restrictor 110, and moveable element 120 can include any combination of shapes when defining the flow channel 104b. For example, any of the chamber 102, restrictor 110, and moveable element 120 can include a rectangular, cylindrical, polygonal, serpentine, trumpet, etc. eccentric cross-sectional cutouts.

Similarly, any combination of relationships between the chamber 102, restrictor 110, moveable element 120, and cutouts 112 can create a flow channel 104b for modifying a flow rate of fluid through the VFR 100. Any sized and shapes gap (e.g., flow channel 104b) created between overlapping portions of the restrictor 110 and moveable element 120 can act as a flow modifier by adjusting the resistance to fluid flowing through the chamber 102. The dimensions of the flow channel 104*b* can dictate the level of resistance because the resistance of the flow channel 104*b* can be proportional to the total cross-sectional area and length of the flow channel 104*b*.

The specific cross-sectional area of the flow channel 104*b* can be determined by the spatial relationship between the moveable element 120 and the restrictor 110. As discussed herein, the length of the flow channel 104*b* can be defined by the overlap between the restrictor 110 and the moveable element 120 and by multiplying the length of overlap by the total cross-sectional area a resistance to flow through the channel 104*b* can be determined. Since the length of the overlap (L) is dependent on the position of the moveable element 120 within the chamber 102, the resistance to flow through the flow channel 104*b* is also dependent on the position of the moveable element 120 within the chamber 102 and amount of overlap with the restrictor 110. As a result, the VFR 100 enables a customizable flow resistance that is adjustable based on the relationship of the geometric and spatial relationship between the chamber 102, restrictor 110, moveable element 120, and any cutouts 112 which ultimately dictates the geometry of the flow channel 104*b*, and thus flow resistance through the VFR 100.

In some embodiments, a flow rate from the input 106 to the output 108 can be controlled to a consistent desired rate using the VFR 100 in accordance with the present disclosure. In particular, the positioning of the moveable element 120 can be adjusted to account for the change in pressure between the input 106 to the output 108 because the resistance to flow is proportional to the flow rate of the fluid through the VFR 100 (e.g., resistance to flow=Δ Pressure from the input 106 to the output 108 divided by the flow rate).

Figure 6A:
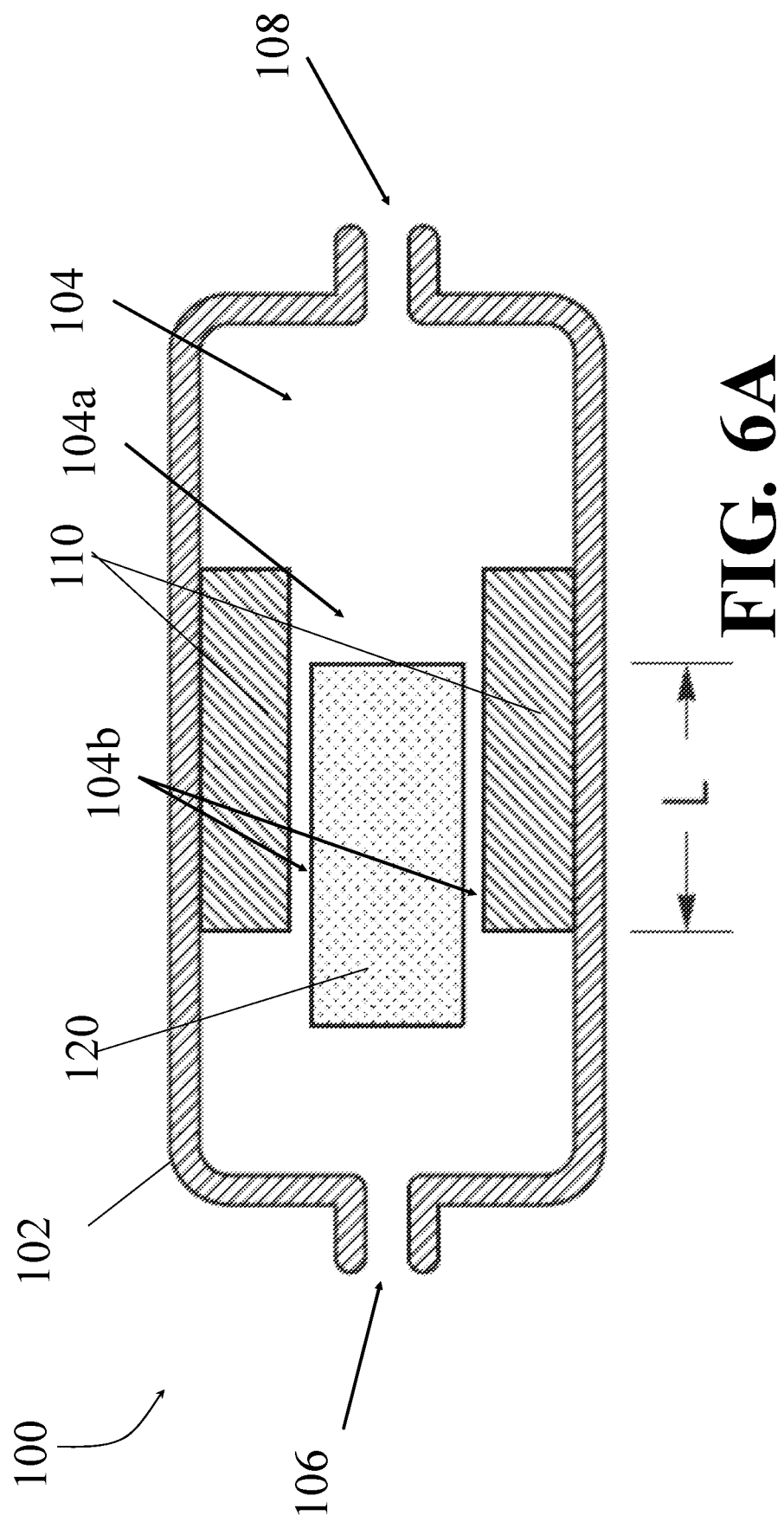
FIG. 6A is an example cross-sectional side view of a variable flow resistor, in accordance with some embodiments of the present disclosure.

As discussed herein, the resistance values are directly related to the geometric properties and relationships of the various components of the VFR 100. The configuration of the VFR 100 allows for the minimum (Rmin) and maximum (Rmax) resistance provided by the combination of the CSA 104*a* and moveable element 120 to be directly determined by the minimum and maximum overlap of the moveable element 120 and the restrictor 110 (Lmin and Lmax). Fundamentally, the custom relationship between moveable element 120 position and flow resistance can be a monotonic relationship. In simple terms, the flow resistance increases from Rmin to Rmax as the overlap between the moveable element 120 and the CSA 104*a* increases from Lmin to Lmax (extending flow channel 104*b*). Referring to FIG. 6A, for example, where the cross-sectional area of the flow channel 104*b* is constant (also as shown in FIGS. 3A-5D), the monotonic relationship is linear with the resistance increasing from Rmin to Rmax at a constant rate as the overlap between the moveable element 120 and the restrictor 110 increases from Lmin to Lmax, as shown in graph 600 depicted in FIG. 6B.

Figure 6B:
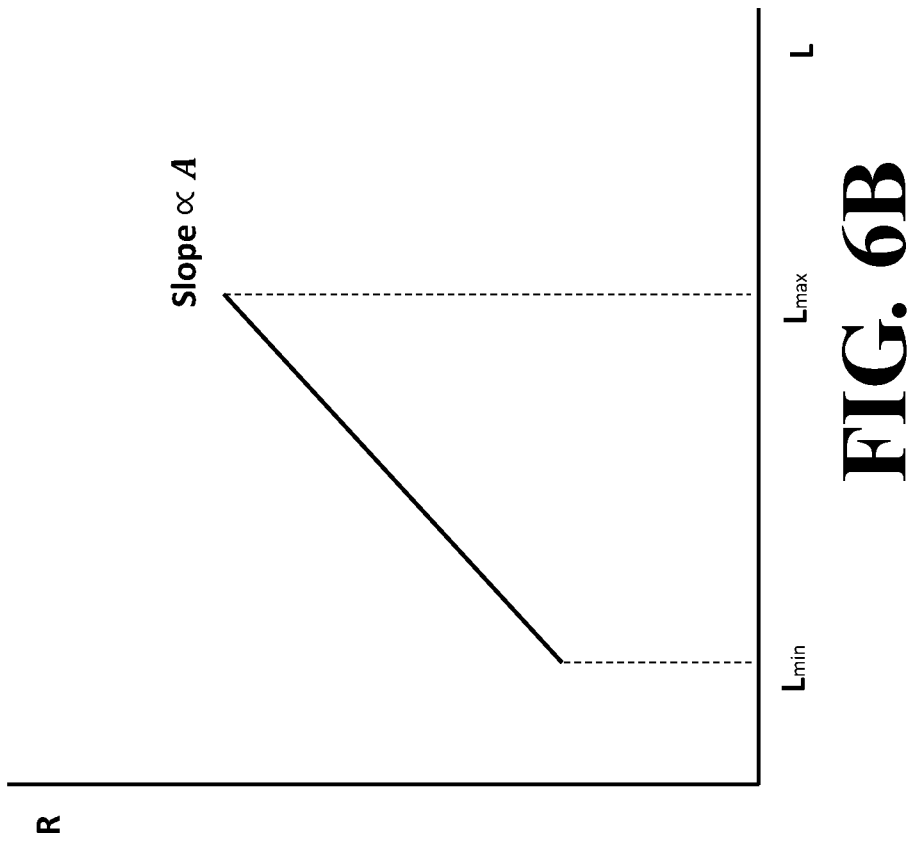
FIG. 6B is an example chart showing effect of the variable flow resistor in FIG. 6A, in accordance with some embodiments of the present disclosure.

Referring to FIG. 6B, the graph 600 in shows a relationship of the length of the moveable element 120 position in relation to the restrictor 110 versus flow resistance of the flow channel 104*b* when the cross-sectional area of the flow channel 104*b* is constant. Although FIG. 6A depicts an example where symmetrical restrictor 110 is implemented to create a constant shaped flow channel 104*b* with the moveable element 120, any combination of shapes and designs can be utilized to create a flow channel 104*b* that is constant. For example, the asymmetric restrictor 110 design from FIG. 1B could be utilized with a uniformly shaped moveable element 120 positioned parallel to the restrictor 110 to provide a flow channel 104*b* that is constant.

Figure 7A:
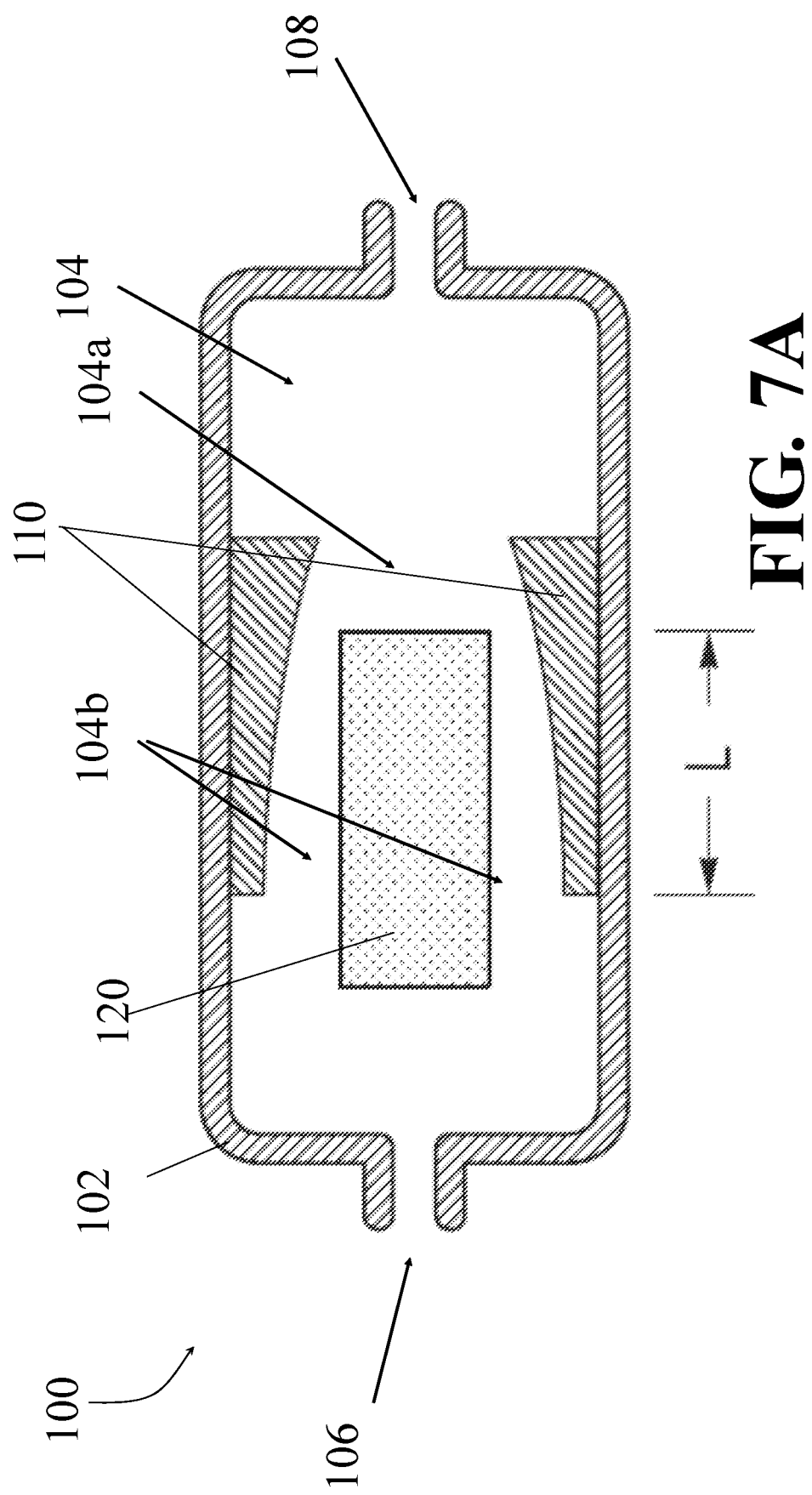
FIG. 7A is an example cross-sectional side view of a variable flow resistor, in accordance with some embodiments of the present disclosure.
Figure 7B:
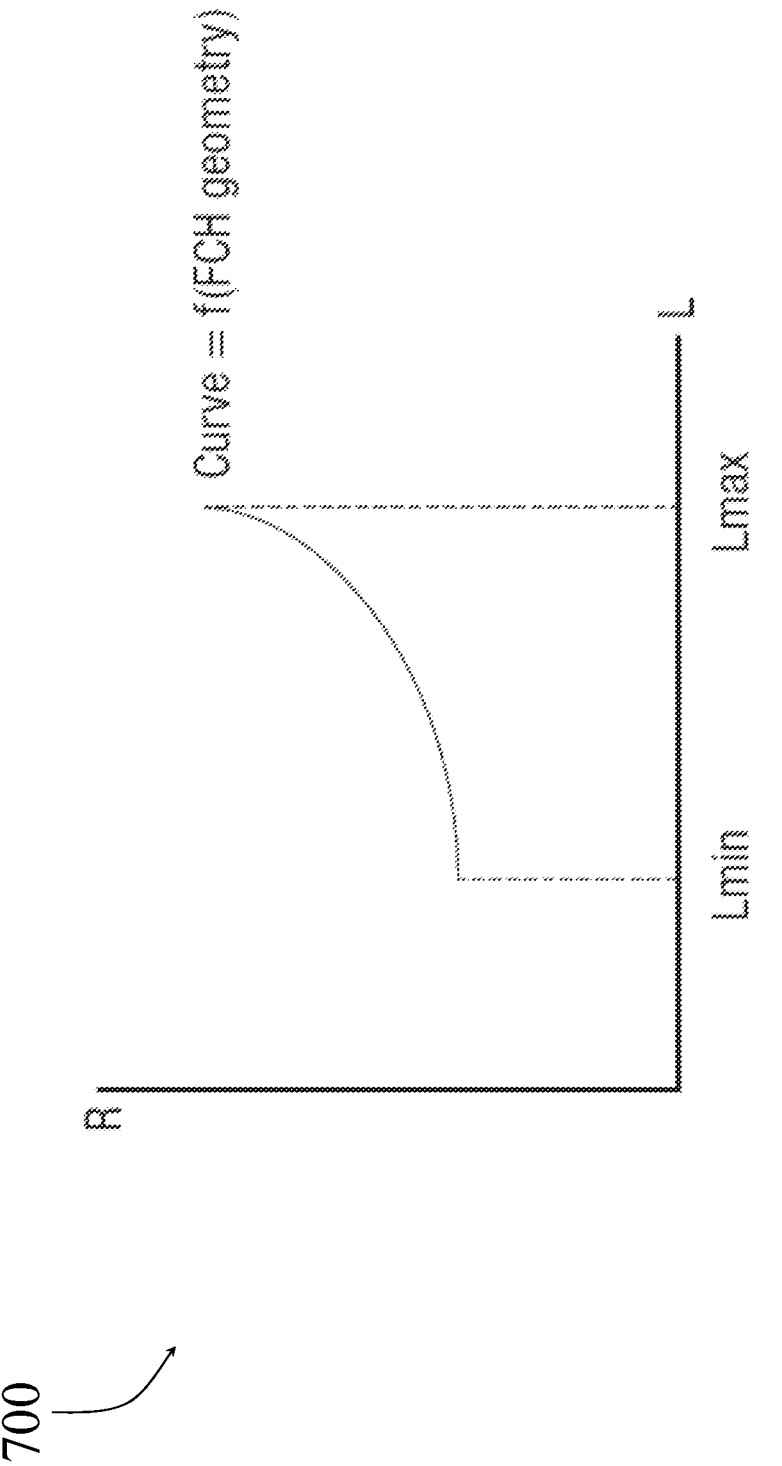
FIG. 7B is an example chart showing effect of the variable flow resistor in FIG. 7A, in accordance with some embodiments of the present disclosure.

Referring to FIG. 7A, in embodiments, the variable flow resistor 100 can include a decreasing CSA 104*a* as progressing toward a distal end of the chamber 102, the decrease created by the geometry of the restrictor 110. Where the flow channel cross-sectional area is decreasing, the monotonic relationship follows a concave down non-linear trajectory with the resistance increasing at a decreasing rate from Rmin to Rmax as the overlap increases from Lmin to Lmax, as shown in graph 700 depicted in FIG. 7B. Referring to FIG. 7B, the graph 700 shows a relationship of the length of the moveable element 120 position in relation to the restrictor 110 versus flow resistance of the flow channel 104*b*.

Although FIG. 7A depicts an example where an asymmetrical restrictor 110 is implemented to create a decreasing shaped flow channel 104*b* with the moveable element 120, any combination of shapes and designs can be utilized to create a flow channel 104*b* that is decreasing. For example, the symmetrical restrictor 110 design from FIG. 1A could be utilized with a moveable element 120 that increases in height/width to provide a flow channel 104*b* that is decreasing. This effect can also be created by a cutout 112 (similar to the cutouts 112 in FIGS. 5C and 5D) that decreases in size as it extends in the direction from the proximal end to the distal end. Similarly, any combination of shapes for the restrictor 110 and the moveable 120 element can be used to create a flow channel 104*b* that increases in size within the chamber 102. As would be appreciated by one skilled in the art, an increasing CSA 104*b* would yield an opposite effect.

Figure 8A:
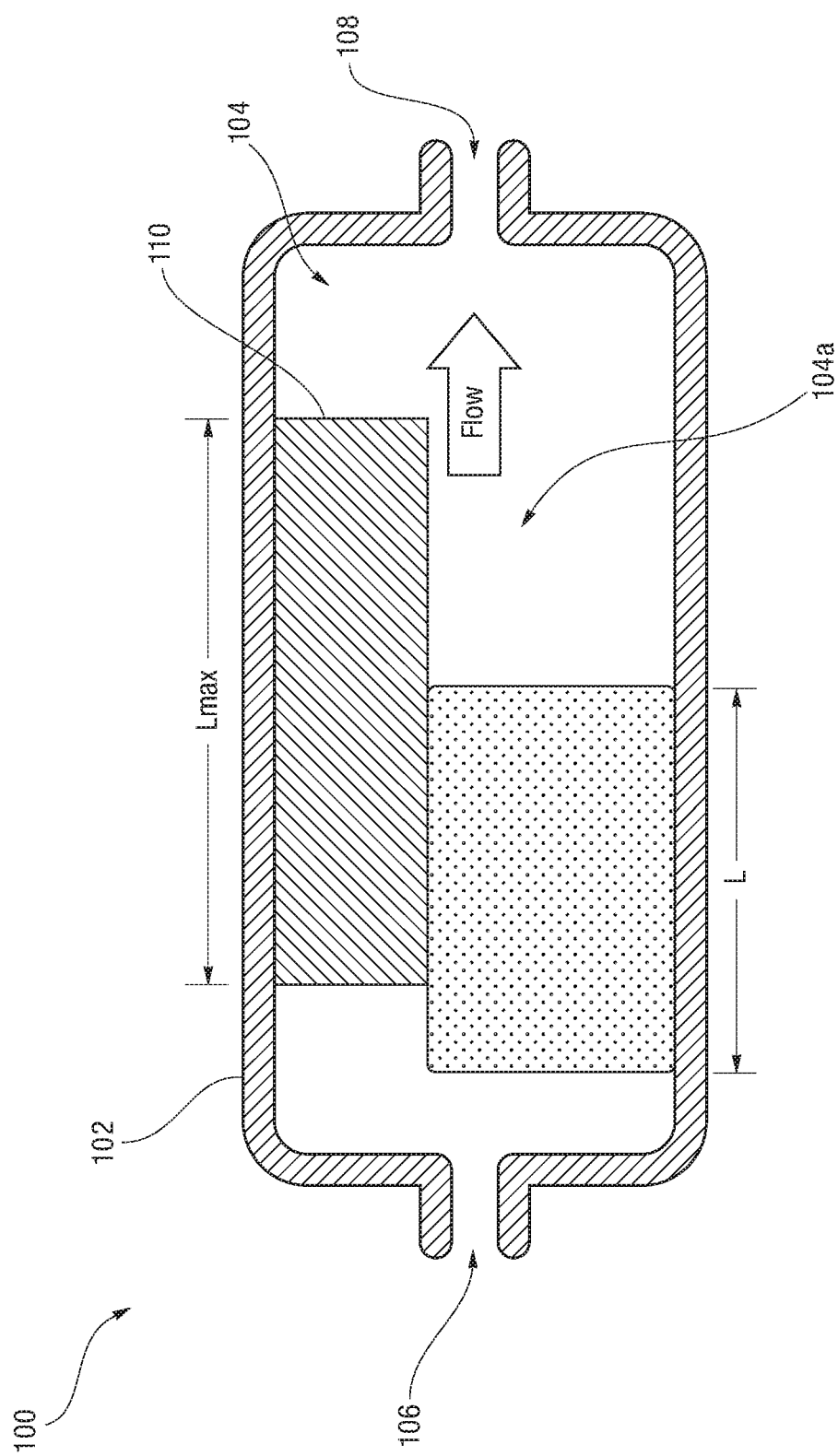
FIG. 8A is an example cross-sectional side view of a variable flow resistor, in accordance with some embodiments of the present disclosure.
Figure 8B:
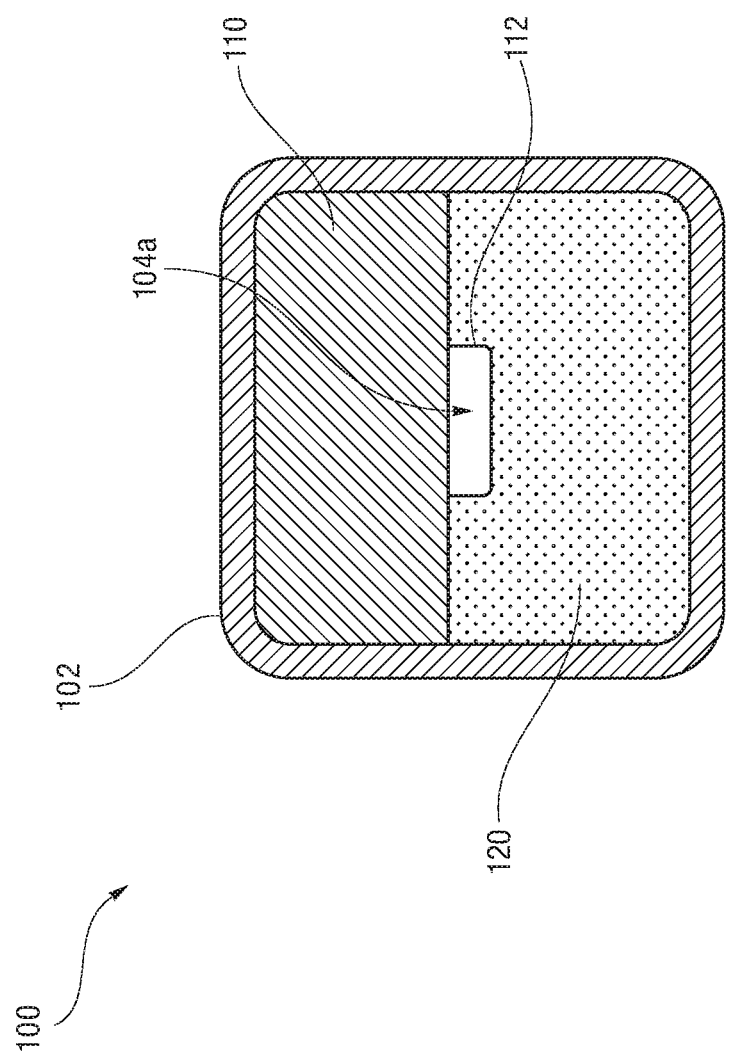
FIG. 8B is an example cross-sectional end view of the variable flow resistor in FIG. 8A, in accordance with some embodiments of the present disclosure.
Figure 8C:
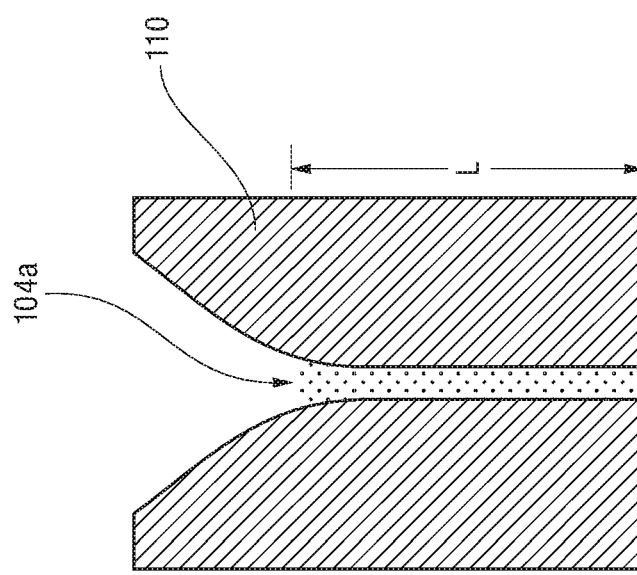
FIG. 8C is an example cross-sectional top view of the variable flow resistor in FIG. 8A, in accordance with some embodiments of the present disclosure.

Referring to FIGS. 8A-8C, in embodiments the variable flow resistor 100 can include an increasing CSA 104*a* created by the geometry of a cutout 112 within the moveable element 120. FIG. 8A depicts a side cross-sectional view of an example VFR 100 with a moveable element 120 that occupies substantially an entirety of a CSA 104*a* with sides being adjacent to interior wall of the chamber 102 and the asymmetric restrictor 110. FIG. 8B depicts a cross-sectional end view of the VFR 100 in FIG. 8A, in which a cutout 112 creates a flow channel 104*b* through which fluid can flow through the chamber 102. Referring to FIG. 8C, in some embodiments, the geometry of the cutout 112 can be increasing in area, as shown in the above cross-sectional view of the VFR 100 from FIGS. 8A-8B.

Where the flow channel 104*b* is increasing, this monotonic relationship follows a concave up non-linear trajectory with the resistance decreasing at a decreasing rate from Rmin to Rmax as the overlap increases from Lmin to Lmax as shown in graph 800 in FIG. 8D. The graph 800 in FIG. 8D shows relationship of the length of the moveable element 120 position in relation to the restrictor 110 versus flow resistance of the flow channel 104*b*. Although FIGS. 8A-8C depict an example where the moveable element 120 includes an eccentric cutout 112 with a trombone shape that creates non-linear relationship with the asymmetrical restrictor 110 to create an increasing shaped flow channel 104*b*, any combination of shapes and designs for the restrictor 110, moveable element 120, and cutouts 112 can be utilized to create a flow channel 104*b* that is increasing in area. For example, the symmetrical restrictor 110 design from FIG. 1A could include trombone shapes cutout (such as the cutout shown in FIG. 8C) and can be utilized with a symmetrical moveable element 120 to provide a flow channel 104*b* that is increasing. Similarly, any combination of shapes for the restrictor 110 and the moveable 120 element can be used to create a flow channel 104*b* that increases in size within the chamber 102.

Furthermore, the specific axial and position of the moveable element 120 within a flow chamber 102 may be determined by one of many mechanisms including but not limited to: flow pattern within the chamber 102, pressure differential, and other additional structural elements within the chamber 102 such as elastic elements, rails, stops, magnetic properties, pushrods, and screws. More specifically, these mechanisms can be used to establish the moveable element 120 position that relies on pressure differential as an input variable. As a result, the variable flow resistor 100 of the present disclosure allows a custom relationship between the pressure differential and the moveable element 120 position, which in turn determines the flow resistance, which in turn determines the flow rate.

As previously described, there are minimum and maximum values for the overlap (Lmin and Lmax) and the resistance (Rmin and Rmax), similarly, there are maximum and minimum pressure differentials. As a result of the above, the variable flow resistor 100 can be designed to have an intrinsic operating range with respect to the pressure differential across which the resistance varies consistent with the underlying properties of the VFR 100. When the pressure differential is outside that range, the device can act as a fixed resistor. The maximum pressure differential (ΔPmax) in this operating range relates to the maximum resistance (Rmax) which in turn relates to the maximum overlap (Lmax). In some embodiments, if the pressure differential above the maximum pressure differential (ΔPmax), the moveable element 120 position remains fixed such that the overlap is equal to the maximum overlap (Lmax) and the resistance remains fixed at the maximum resistance (Rmax), independent of the pressure differential.

Like the maximum pressure differential, the minimum pressure differential (ΔPmin) in this operating range relates to the minimum resistance (Rmin) which in turn relates to the minimum overlap (Lmin). If the pressure differential is below the minimum pressure differential (ΔPmin), the moveable element 120 position remains fixed such that the overlap is equal to the minimum overlap (Lmin) and the resistance remains fixed at the minimum resistance (Rmin), independent of the pressure differential. In short, if the pressure differential, or change in pressure, is greater than the maximum pressure differential then the flow rate (Q) may no longer remain constant.

Figure 9:
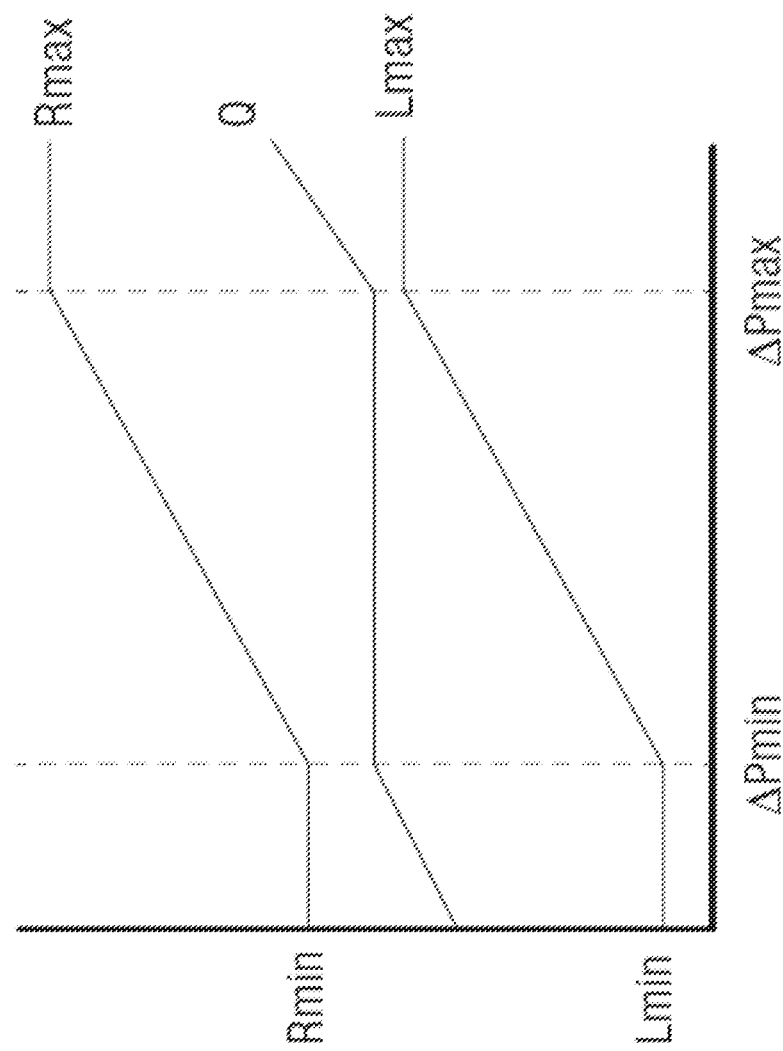
FIG. 9 is an example chart showing effect of the variable flow resistor, in accordance with some embodiments of the present disclosure.

Referring to FIG. 9, a graph 900 is provided to show the relationship of the volumetric fluid flow rate (Q) (e.g., through channel 104b), resistance to flow (R) (e.g., created by chamber 102, CSA 1-4a, channel 104b, etc.), and length of overlap between the moveable element 120 and restrictor 110 (L) as they relate to the pressure differential. In short, i) as the pressure differential approaches a minimum pressure differential for the VFR 100, the L and R will maintain an initial minimum value, ii), when the pressure differential is between the minimum and maximum pressure differential value for the VFR 100, each of the L and R values will increase in a linear manner while Q remains constant, and iii) if the pressure differential exceeds a maximum pressure differential for the VFR 100, the L and R will maintain a final maximum value (different from the value when less than the minimum pressure differential) while the Q value will increase. In some embodiments, the VFR 100 can be designed to operate within specific pressure input parameters to ensure that it can properly maintain a consistent flow rate (Q) as the input pressure varies.

Figure 10A:
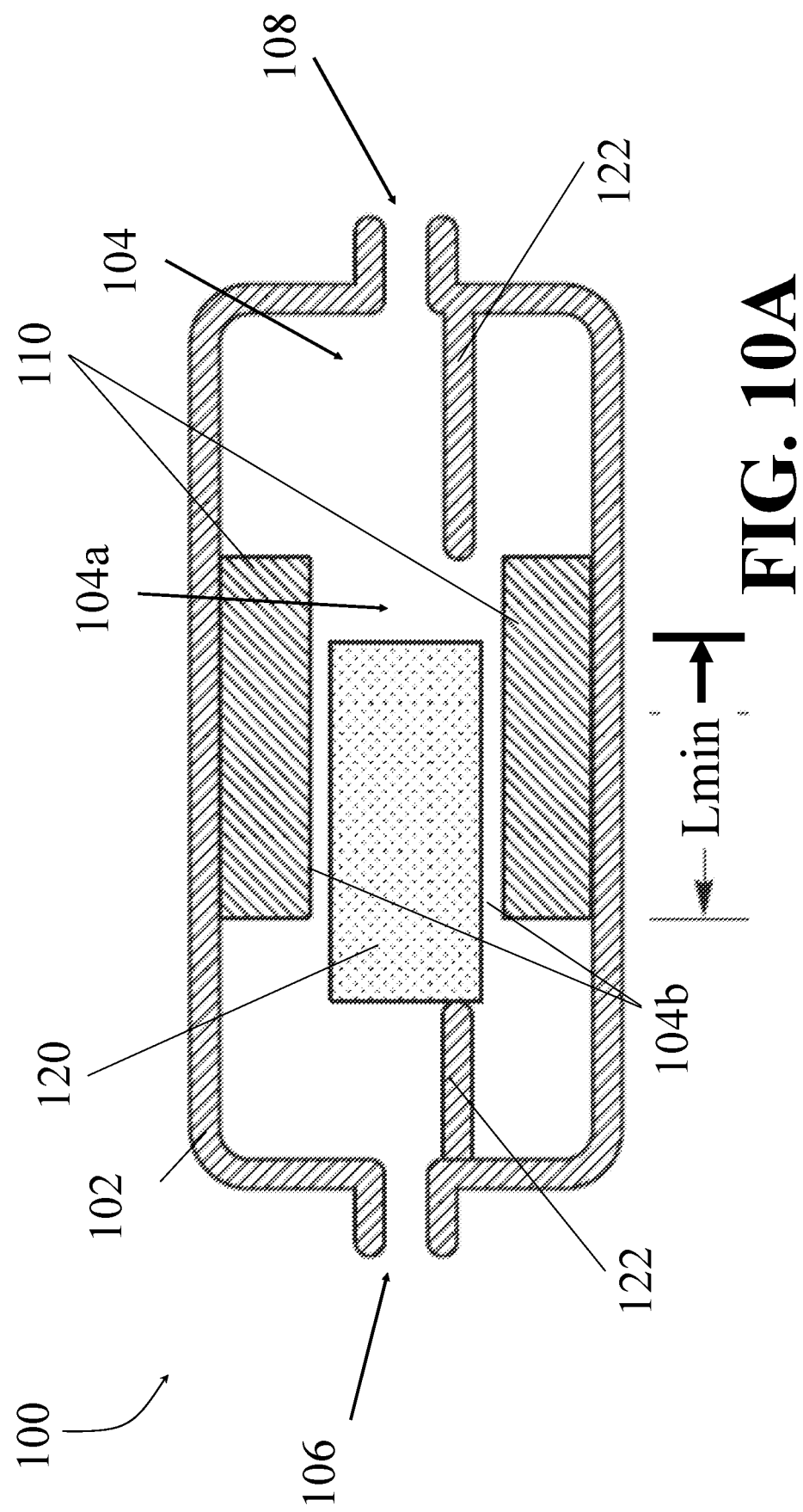
FIGS. 10A and 10B are example cross-sectional side views of a variable flow resistor, in accordance with some embodiments of the present disclosure.
Figure 10B:
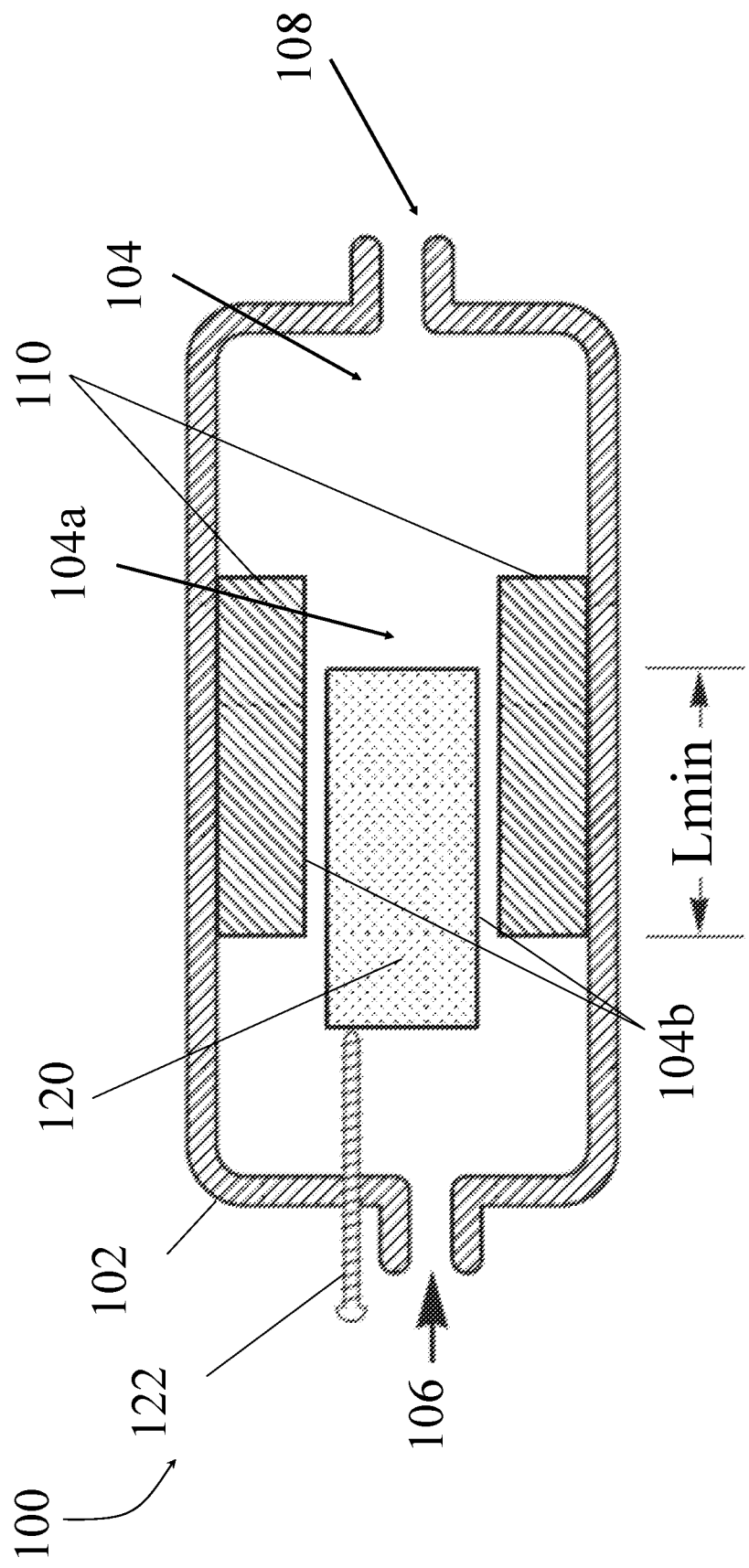

Referring to FIGS. 10A and 10B, in some embodiments, the variable flow resistor can include one or more stops 122 positioned within the chamber 102. The stops 122 can be positioned such that they limit the minimum and/or maximum overlap between the moveable element 120 and the restrictor 110. The stop 122 can include any combination of sized and shaped material configured to stop the moveable element 120 from traversing beyond a certain point within the chamber 102. For example, the stop 122 can be a static protrusion extending from the wall of the chamber (as shown in FIGS. 4A and 10A), an adjustment mechanism (e.g., screw shown in FIG. 10B), or any other mechanical structure known in the art. Using an adjustable stop 122, as depicted in FIG. 10B, the Lmin and Lmax can be adjusted as the minimum and maximum movement of the moveable element 120 in relation to the restrictor 110 is impacted by the position of the adjustable stop 122.

Similar to the restrictor 110, the stop 122 can include any combination of asymmetrical and eccentrical shapes. For example, a stop 122 can be a continuous symmetrical shape extending around the chamber 102, as depicted in FIG. 4A, or it can be one or more separate protrusions extending from the chamber 102, as depicted in FIG. 10A. The stop(s) 122 can also be located on either the proximal and/or distal end of the chamber 102 or a combination thereof, as depicted in FIG. 10A. Additionally, multiple different types of stops 122 can be implements within the same variable flow resistor 100. For example, a proximal end of the resistor 100 can include an adjustable stop 122 (as shown in FIG. 10B) and the distal end of the resistor 100 can include a fixed stop 122 (as shown in FIG. 10A).

Figure 11:
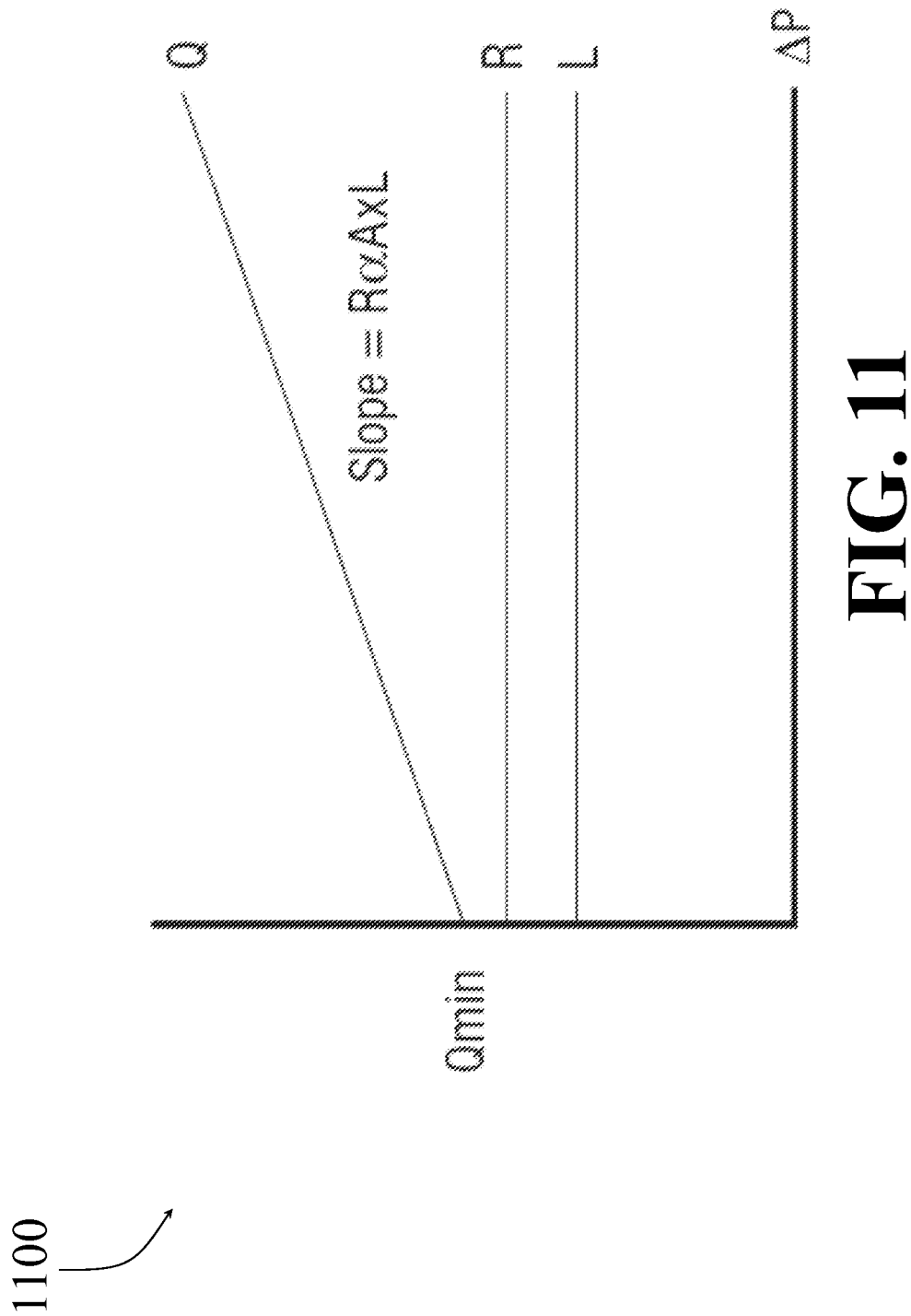
FIG. 11 is an example chart showing effect of the variable flow resistor in FIGS. 10A and 10B, in accordance with some embodiments of the present disclosure.

Referring to FIG. 11, a graph 1100 is depicted that shows a relationship of the moveable element 120 position (L) versus flow resistance (R) it relates to the structures of FIGS. 10A and 10B. In other words, graph 1100 shows what happens when there is a fixed overlap between a moveable element 120 and a restrictor 110. IN such instances, as reflected in graph 1100, the flow resistance (R) is constant and the overlap (L) is constant because the moveable element 120 is stationary. Therefore, the flow rate (Q) goes up as the pressure goes up. FIG. 10A provides a moveable element 120 which can traverse within the reduced cross-section 104a until it hits a distal stop 122, which results in the relationships depicted in graph 1100. More specifically, as shown in graph 1100 in, any introduction of a pressure differential would move the moveable element 120 within the chamber 102 (until it bottoms out against the stop 122), such that an instantaneous step increase of flow rate (Q), flow resistance (R) and overlap length (L) is provided. As the pressure continues to increase, the flow rate (Q) increases while the flow resistance (R) and overlap length (L) remain constant as the pressure differential increases.

Figure 12A:
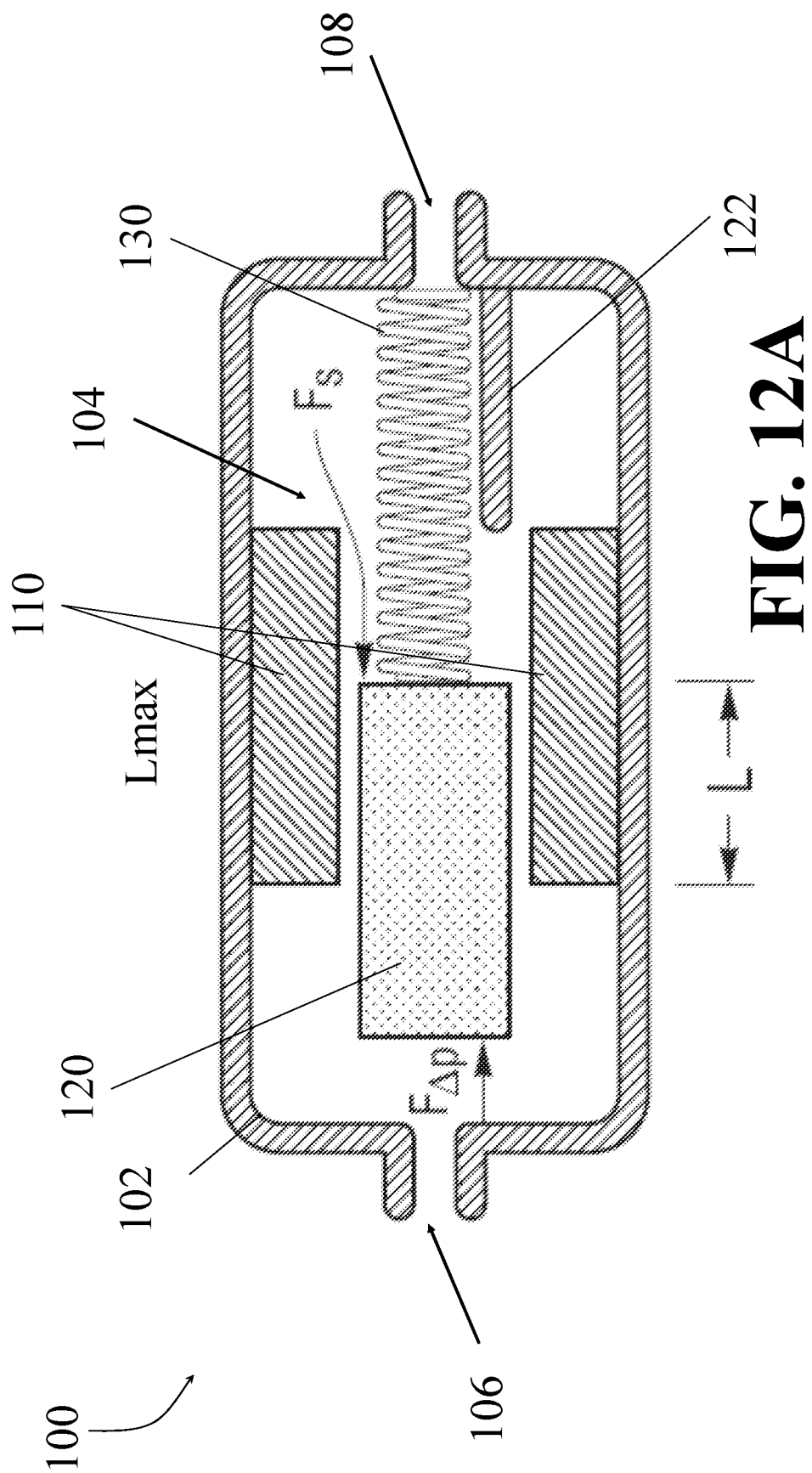
FIGS. 12A and 12B are example cross-sectional side views of a variable flow resistor, in accordance with some embodiments of the present disclosure.
Figure 12B:
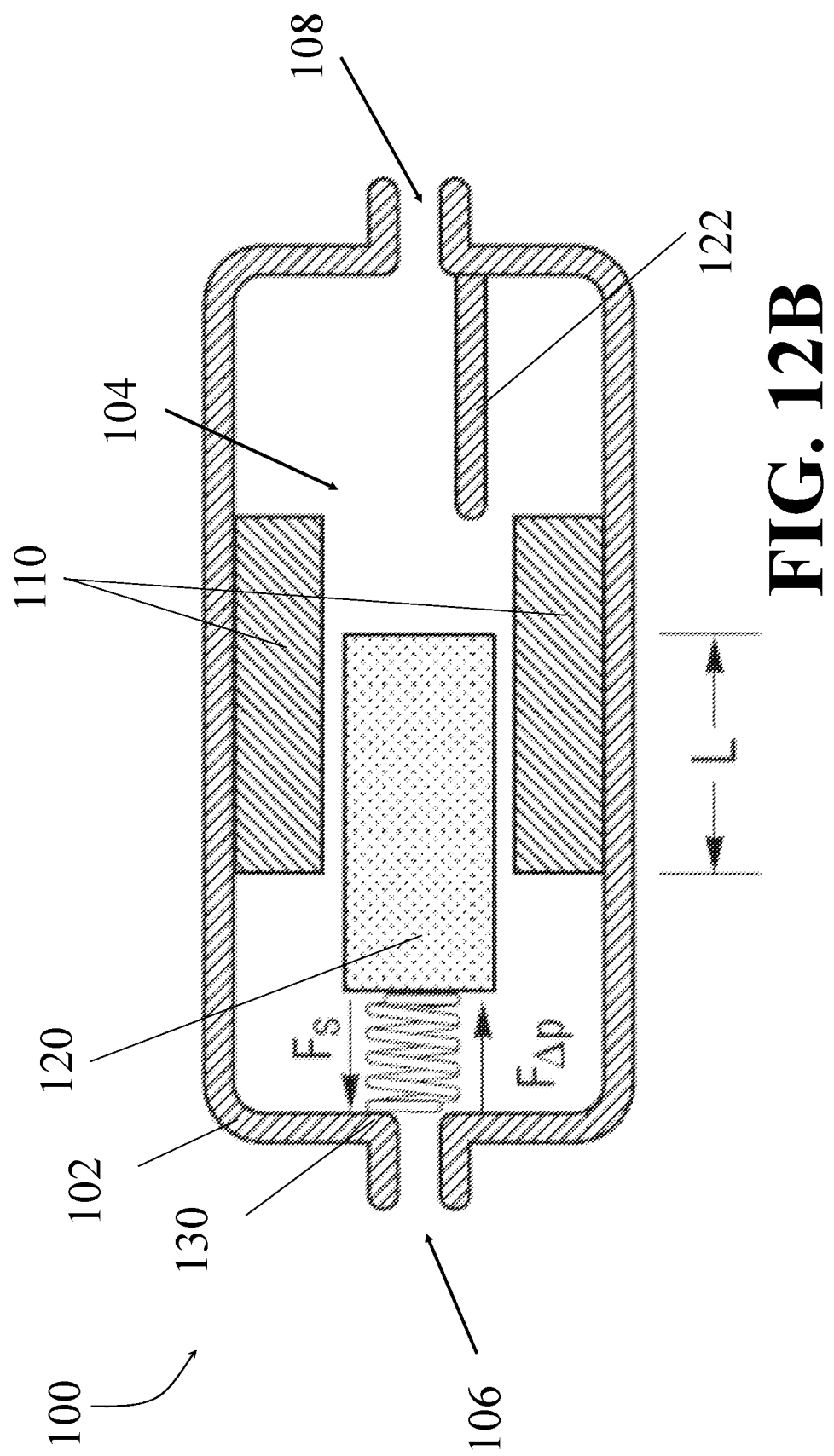

Referring to FIGS. 12A-12B, in some embodiments, the variable flow resistor 100 can include one or more springs or other biasing mechanisms 130 coupled to at least one end of the moveable element 120 and the chamber 102. The biasing mechanisms 130 can be coupled to the moveable element 120 and the chamber 102 using any combination of mechanisms known in the art. The biasing mechanisms 130 can be configured to limit the amount of movement of the moveable element 120 within the chamber 102 as well as the amount of force needed to move the moveable element 120. In some embodiments, a biasing mechanism 130 can mechanically interface with the moveable element 120 within the flow chamber 102 and can be used to exert a force directed proximally along the direction which counterbalances the distally directed force generated by any pressure differential between the input 106 and the output 108. As would be appreciated by one skilled in the art, the biasing mechanism 130 can also be a non-mechanical element such as a compressible gas or fluid. In some embodiments, additional mechanical forces can be applied to the moveable element 120 to further customize the resistance to flow and flow rate through the device VFR 100.

Referring to FIG. 12A, in some embodiments, biasing mechanism 130 can be a compression spring that resides in the chamber 102 and is coupled to at least one end of the moveable element 120. In order for the spring force (Fs) to be directed proximally, if the biasing mechanism 130 is of a compression type, then the biasing mechanism 130 can be located within the distal end of the chamber 102, as depicted in FIG. 12A. More specifically, the biasing mechanism 130 can be located in the flow chamber 102 distal to the moveable element 120 and interface proximally with the distal end of the moveable element 120 and interface distally with the distal wall or other distal structural component of the flow chamber 102. In this configuration, as force/pressure ($F_{\Delta P}$), sufficient to counter the spring force (Fs) of the biasing mechanism 130, is applied to the proximal end of the moveable element 120, the spring 130 will compress (e.g., according to hooks law) to allow the moveable element 120 to move within the chamber 102.

Referring to FIG. 12B, in some embodiments, the biasing mechanism 130 can be an extension type and can be located within the proximal end of the chamber 102. More specifically, the biasing mechanism 130 can be located in the flow chamber 102 proximal to the moveable element 120 and interface proximally with the proximal end of the moveable element 120 and proximally with the proximal wall or other proximal structural component of the flow chamber. In this configuration, as force/pressure ($F_{\Delta P}$), sufficient to counter the spring force (Fs) of the biasing mechanism 130, is applied to the proximal end of the moveable element 120, the spring 130 will expand (e.g., according to hooks law) to allow the moveable element 120 to move within the chamber 102. As would be appreciated by one skilled in the art, the VFR 100 can be modified to use any combination of elastic members, such as springs, can be used. For example, compression, extension, and constant force springs can be used.

The use of the spring force biasing mechanisms 130 depicted in FIGS. 12A and 12B provide a spring force which will act in an opposing direction of the pressure generated by the fluid flow entering the chamber 102 through input 106. Depending on the pressure bring applied to the moveable element 120 and the spring force applied by the biasing mechanism 130, the movement of the moveable element and thus fluid flow through the chamber 102 can be controllable. Therefore, regardless of the positioning of the biasing mechanism 130 within the chamber 102, the properties of the biasing mechanism 130 can determine the range of positions that the moveable element 120 can traverse, and as a result, the maximum and minimum overlaps (Lmin and Lmax). For example, with a compression spring positioned distal to the moveable element 120, the minimum overlap (Lmin) is determined by the neutral length of the spring and the maximum overlap (Lmax) is determined by the length of the spring in its substantially or fully compressed state. In some embodiments, other elements to manage the movement of the moveable element 120 could also be used in combination with the elastic element. For example, as depicted in FIGS. 12A and 12B, the VFR 100 can include a stop 122 located at least one end of the chamber 102. The inclusion of a stop 122 can limit one or both of the Lmin and Lmax regardless of spring force provided by the biasing mechanism 130. The stop 122 can be located on either end of the chamber 102 and is not limited to the distal placement provided in FIGS. 12A and 12B.

Figure 12C:
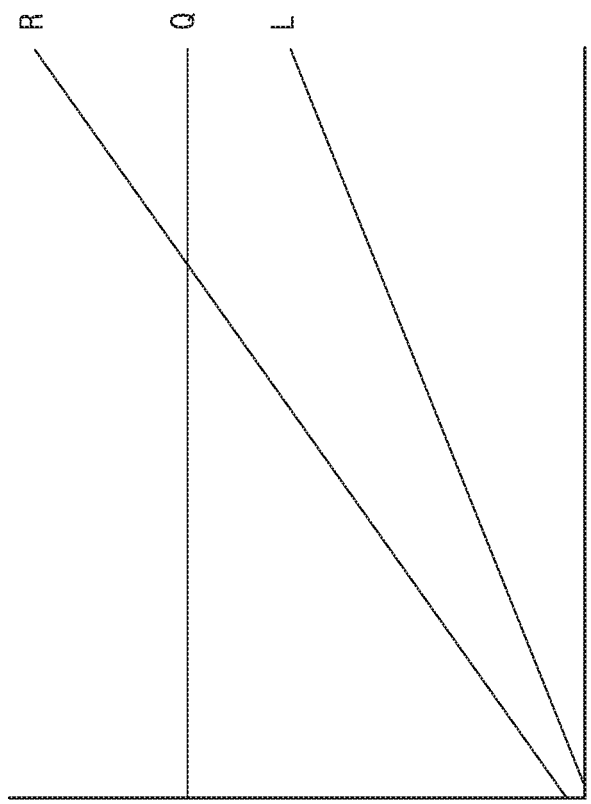
FIG. 12C is an example chart showing effect of the variable flow resistor in FIGS. 12A and 12B, in accordance with some embodiments of the present disclosure.
Figure 12C:
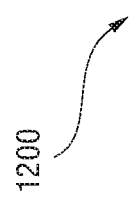

In some embodiments, where the cross-sectional area of the flow channel 104b remains constant and the biasing mechanism 130 is a classic spring that obeys Hooke's Law, the linear relationship between displacement of the biasing mechanism 130 and spring force matches the linear relationship between moveable element 120 position and flow resistance. This relationship results in consistent flow independent of a pressure differential between the input 106 and output 108 of the chamber 102. The pressure differential operating range in some embodiments can be narrower than the geometrically based minimum and maximum overlap and resistances alone. This operating range can be dependent on the linear range of the biasing mechanism 130. Referring to FIG. 12C, a graph 1200 shows the relationship between the length of the overlap (L), the resistance to flow through the channel 104b (R) and the flow rate (Q) out of the channel 104b, when using a biasing mechanism 130. This relationship is in contrast to the relationship depicted in the graph 110 of FIG. 11. In 12C, the biasing mechanism 130 opposes the force on the moveable element 120 due to the pressure. Therefore, as the pressure changes, the force on the moveable element 120 changes and the biasing mechanism 130 changes in unison allowing the overlap to change, and therefore the resistance to flow to change, resulting a constant flow rate.

Figure 12D:
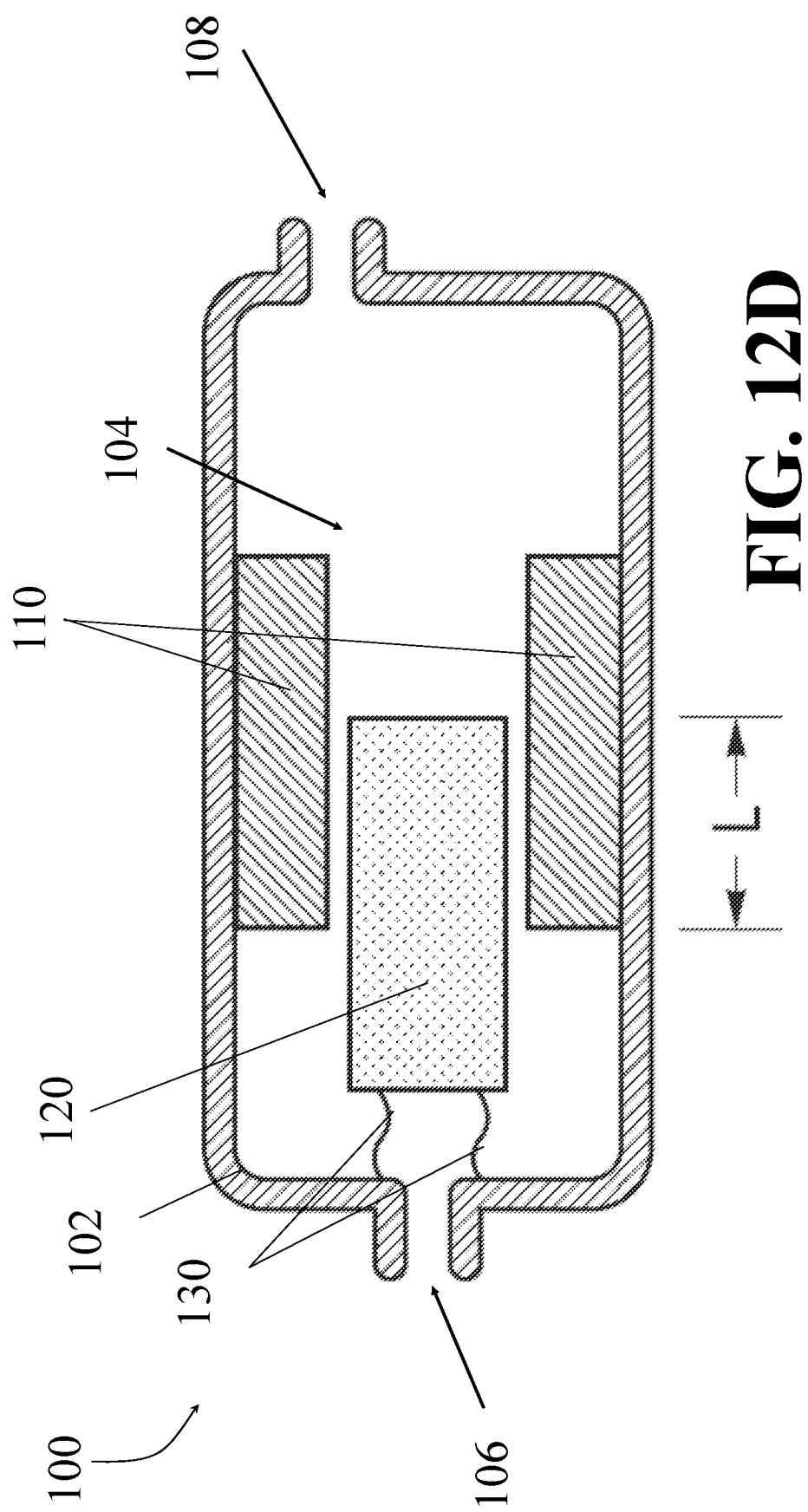
FIGS. 12D and 12E are example cross-sectional side views of a variable flow resistor, in accordance with some embodiments of the present disclosure.

Referring to FIG. 12D, in some embodiments, the biasing mechanism 130 can be an elastomer material that can expand and contract depending on a force being applied to the moveable element 120 coupled thereto. Similar to the spring based biasing mechanisms 130 discussed with respect to FIGS. 12A-12B, the elastomer material can be coupled to the moveable element 120 and the chamber 102 wall using any combination of mechanisms known in the art.

Figure 12E:
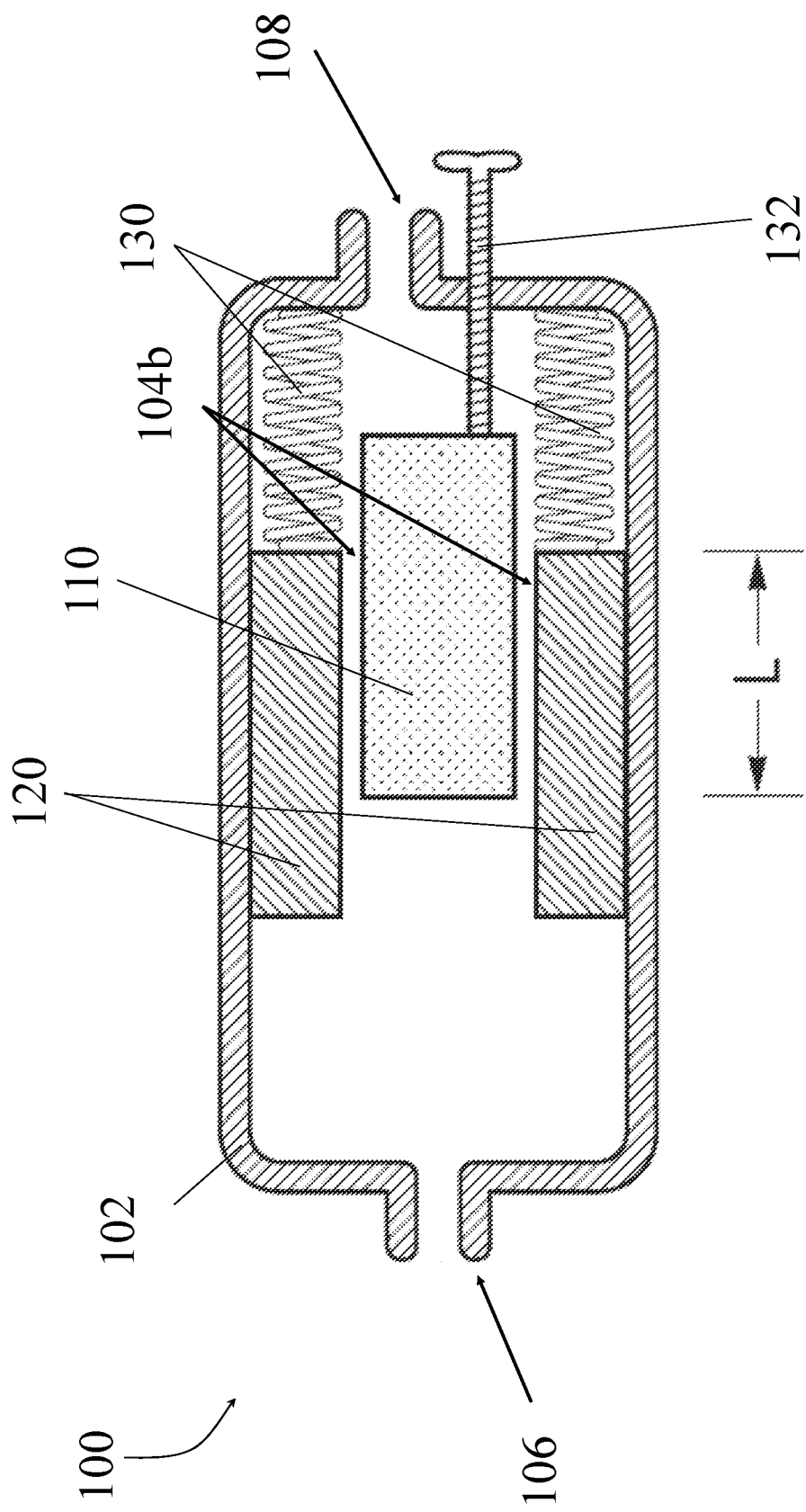

Referring to FIG. 12E, in some embodiments, the moveable element 120 can be positioned on near the walls of the chamber 102 instead of the center of the chamber 102. For example, the moveable element 120 can be located circumferentially substantially adjacent to the walls of the chamber 102. As shown in FIG. 12E, one or more biasing mechanisms 130 can be coupled to the moveable element 120 to adjust the overall flow rate output provided by the VFR 100. In some embodiments, the moveable element 120 can be moveable in a direction in relation to an adjustable restrictor 110, for example using one or more springs (biasing elements 13). For example, as depicted in FIG. 12E, the biasing mechanism 130 can be coupled to a distal end of the moveable element 120 and a proximal side of the distal end of the inner chamber 102. In this arrangement, as force is applied to the moveable element 120, the biasing mechanism 130 will compress and the moveable element 120 can move in a direction.

Continuing with FIG. 12E, in some embodiments, the position of the restrictor 110 can be stationary but adjustable by including an adjustment mechanism(s) 132 coupled thereto. For example, as depicted in FIG. 12E, an adjustable mechanism(s) 132, for example, a screw can be coupled to the distal end of the restrictor 110. As the adjustable mechanism(s) 132 is rotated, the restrictor 110 will move in a particular direction. For example, a clockwise rotation of the adjustable mechanism(s) 132 can move the restrictor 110 in the proximal direction or vice versa. Any combination of rotational and movement can be used. Similarly, any combination of mechanisms can be used to adjust a position of the restrictor 110, for example, a piston, adjustable spring, etc. Although the adjustable mechanism(s) 132 can adjust the position of the restrictor 110, the restrictor 110 can remain stationary, during operation, when the adjustable mechanism(s) 132 is not being rotated. The adjustable mechanism(s) 132 can act to position and keep restrictor 110 stationary while the moveable element 120 moves.

While the spring force provided by a biasing mechanism 130 can influence a flow rate, the flow channel 104b also can be configured to operate in combination with the spring force to provided desired results, for example, maintaining a constant fluid flow. Referring to FIGS. 13A-15E, in some embodiments, the moveable element 120 can be located on the outside and the restrictor 110 can be a stationary plate to be positioned inside the moveable element 120. For example, the moveable element 120 can be a cylindrical piston on a stationary restrictor 110 (e.g., a rail), as depicted in FIGS. 14A and 14B. As discussed herein, the amount of overlap between the moveable element 120 and the restrictor 110 (L) can influence the flow rather through the flow channel 104b situated between the moveable element 120 and the restrictor 110. The moveable element 120 can move along a length the restrictor 110 to affect the flow rate of a fluid through the flow channel 104b.

Figure 13A:
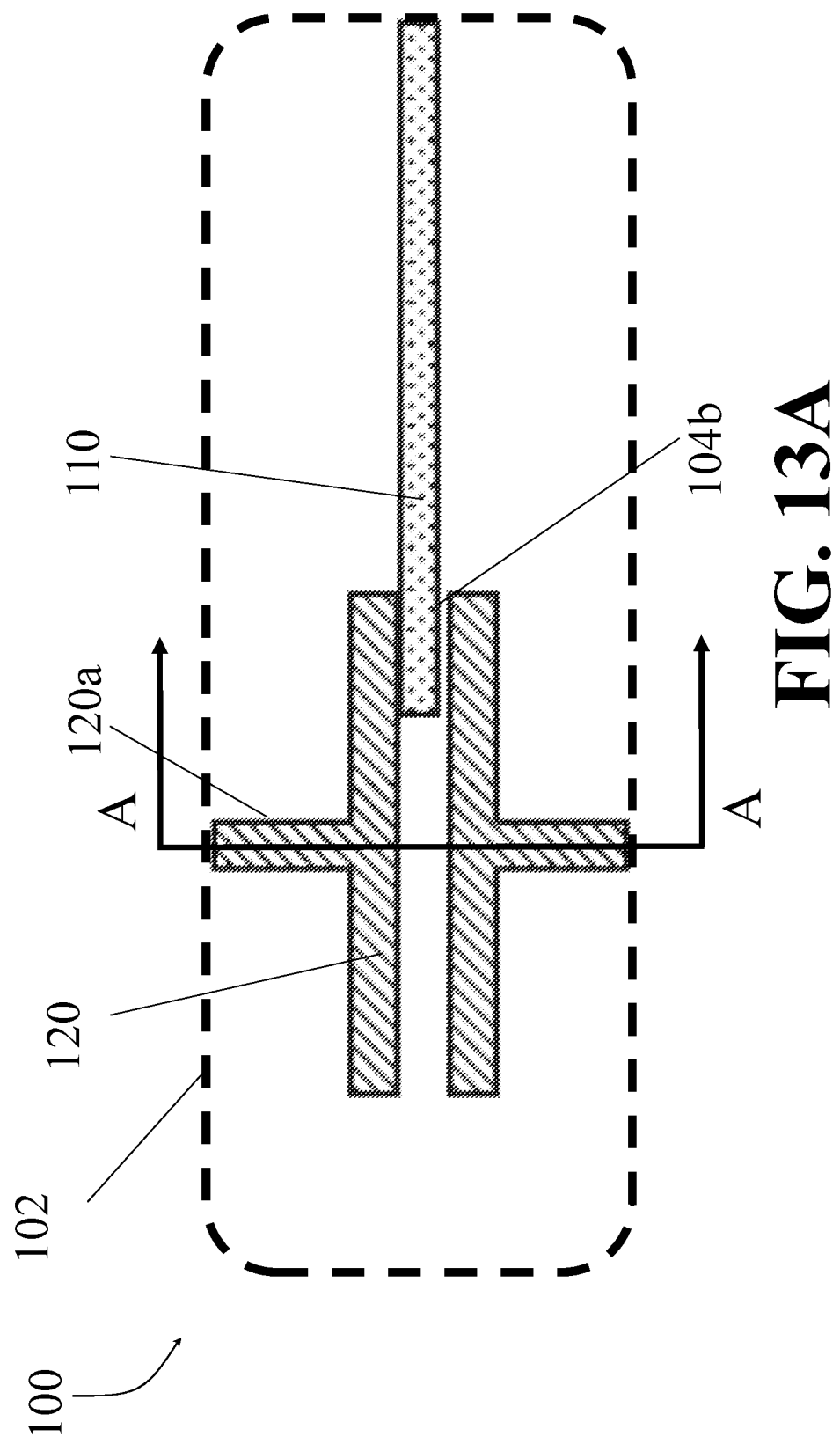
FIG. 13A is example cross-sectional side views of a variable flow resistor, in accordance with some embodiments of the present disclosure.
Figure 14A:
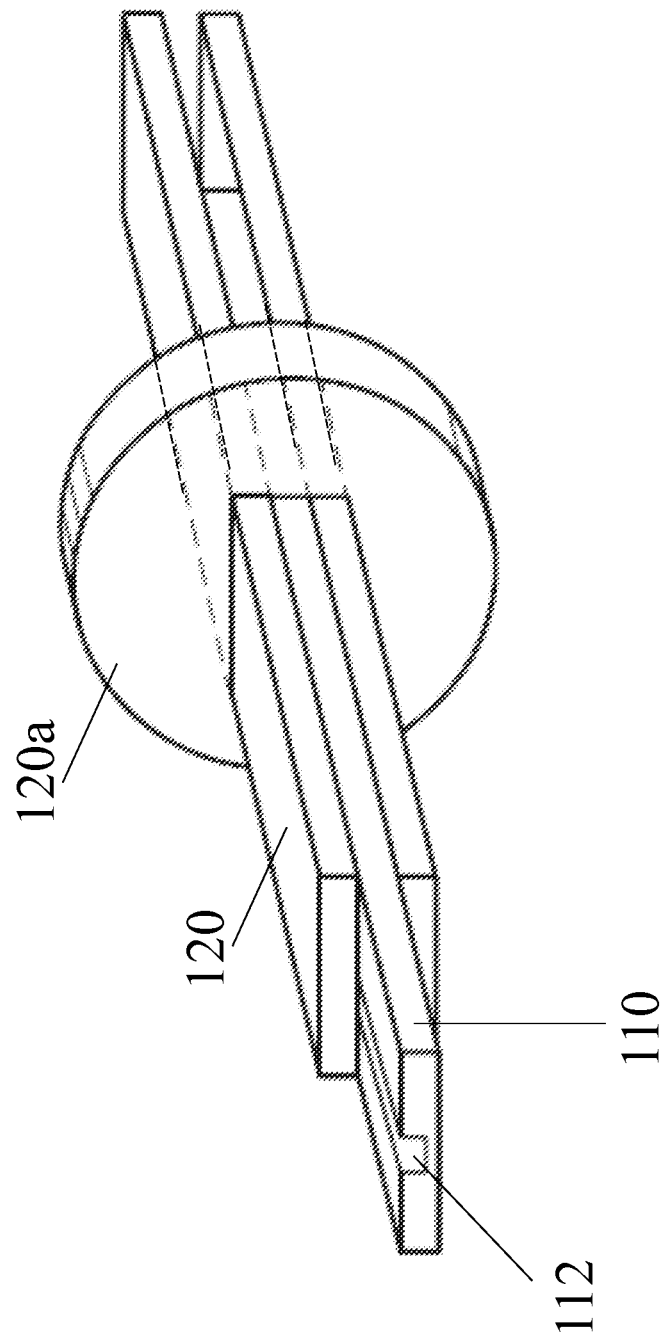
FIGS. 14A and 14B are example orthogonal views of a moveable element positioned around a restrictor for implementation in a variable flow resistor, in accordance with some embodiments of the present disclosure.
Figure 14B:
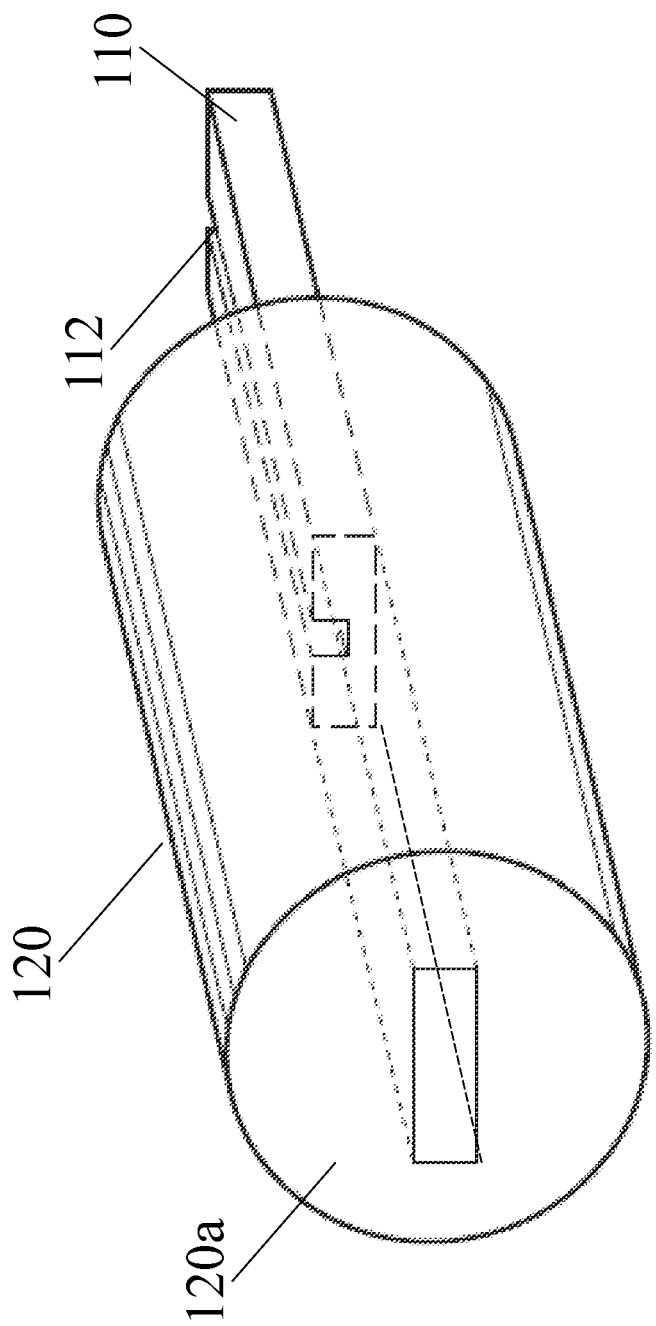

Referring to FIG. 13A, in some embodiments, the moveable element 120 in combination with the restrictor 110 can form a sealed arrangement with the chamber 102 such that fluid can only flow through a flow channel 104b created by the moveable element 120 and the restrictor 110. The moveable element 120 arrangement in FIG. 13A can be combined with any combination of features discussed with respect to FIGS. 1A-12C. For example, positioning of the moveable element 120 along the bugle 110 can be dictated by a combination of a biasing mechanism 130 and one or more stops 122. As discussed herein, the amount of overlap between the moveable element 120 along the bugle 110 will affect the flow rate through the flow channel 104b.

Figure 13D:
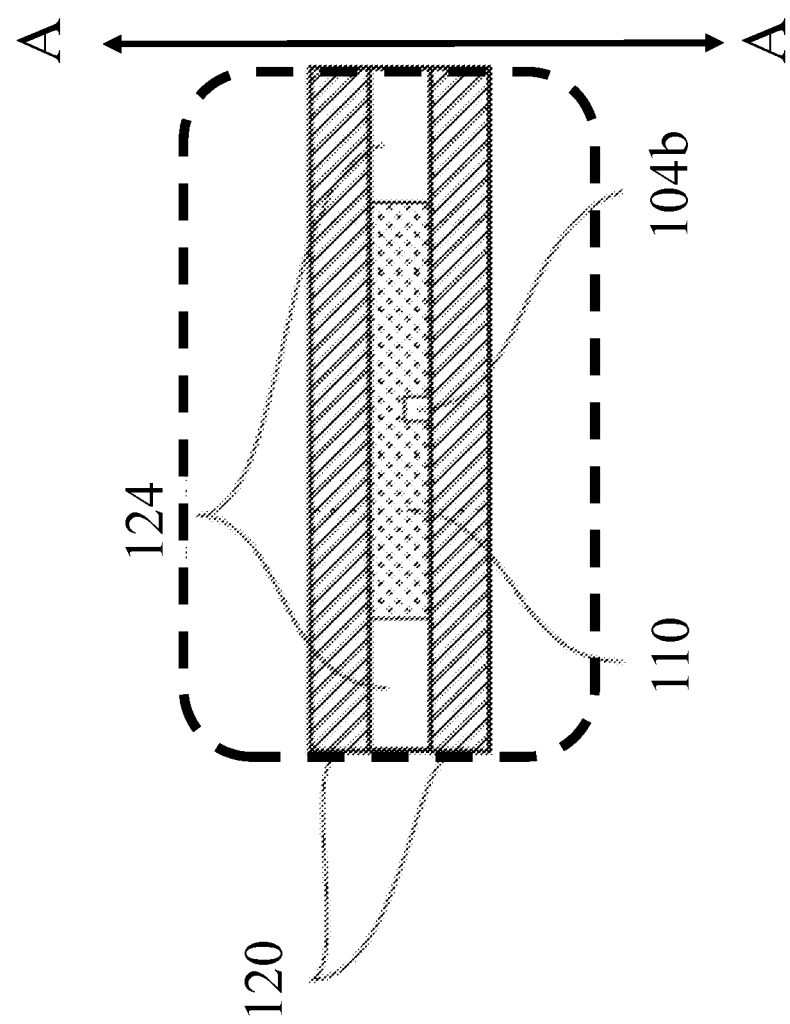

Referring to FIGS. 13B and 13C, a cross-sectional view of a moveable element 120 surrounding the restrictor 110, such as the element 120 in FIG. 13A, is depicted. The moveable element 120 can include a substantially vertical surface 120a that provides a large surface area capable of receiving force from a fluid flow from input 106. In some embodiments, the restrictor 110 has a cutout 112 sized and positioned such that a flow channel 104b is created when the moveable element 120 is positioned around the restrictor 110. As shown in FIGS. 13B and 13D, the restrictor 110 includes a cutout 112 on a bottom portion to establish a flow channel 104b when overlapped by the moveable element 120. The length (L) of overlap of the moveable element 120 over the restrictor 110 will dictate the length of the flow channel 104b and effect the flow rate of fluid through the CAS 104a. Although FIGS. 13B-13D depict a single cutout 112, any number of cutouts can be used without departing from the scope of the present disclosure. Similarly, the cutouts 112 can be provided within any combination of the restrictor 110, the moveable element 120, the chamber 102, etc. to create a flow channel 104b. Similarly, any combination of sizes/scales can be used for the different components. In some embodiments, the restrictor 110 can be sized at a measurable level of millimeters while the cutout 112 therein can be sized at a measurable level of microns. As would be appreciated by one skilled in the art, any sized components can be used for the VFR 100 without departing from the scope of the present disclosure. Referring to FIG. 13D, in some embodiments, the restrictor 110 can be adjacent with one or more seals 124 designed to reduce any friction caused by moveable 120 element traversing over the restrictor 110.

Referring to FIGS. 14A and 14B, orthogonal views of a moveable element 120 positioned around a restrictor 110 is depicted. As shown in FIGS. 14A and 14B, the restrictor 110 includes a cutout 112 on a top portion to establish a flow channel 104b when the restrictor 110 is overlapped by the moveable element 120. In some embodiments, the moveable element 120 can include a substantially vertical surface 120a with horizontal surfaces extending perpendicularly therefrom in a different plane as the top/bottom of the substantially vertical surface 120a, as shown in FIG. 14A. In some embodiments, the moveable element 120 can include a substantially vertical surface 120a with a uniform shape extending from the substantially vertical surface 120a, as shown in FIG. 14B. The size and shape of the moveable element 120, restrictor 110, chamber 102, cutout(s) 112 can all vary based on desired results. Similarly, the materials, textures, weights, etc. of each of the components can vary based on desired results. For example, the moveable element 120 in FIG. 14A may be lighter that the moveable element 120 in FIG. 14B due to its smaller overall mass to provide less resistance to forces applied to the substantially vertical surface 120a. As discussed herein, any combination of shapes can be used for the moveable element 120, bugle 110, cutouts 112, etc. when using this configuration.

Figure 15A:
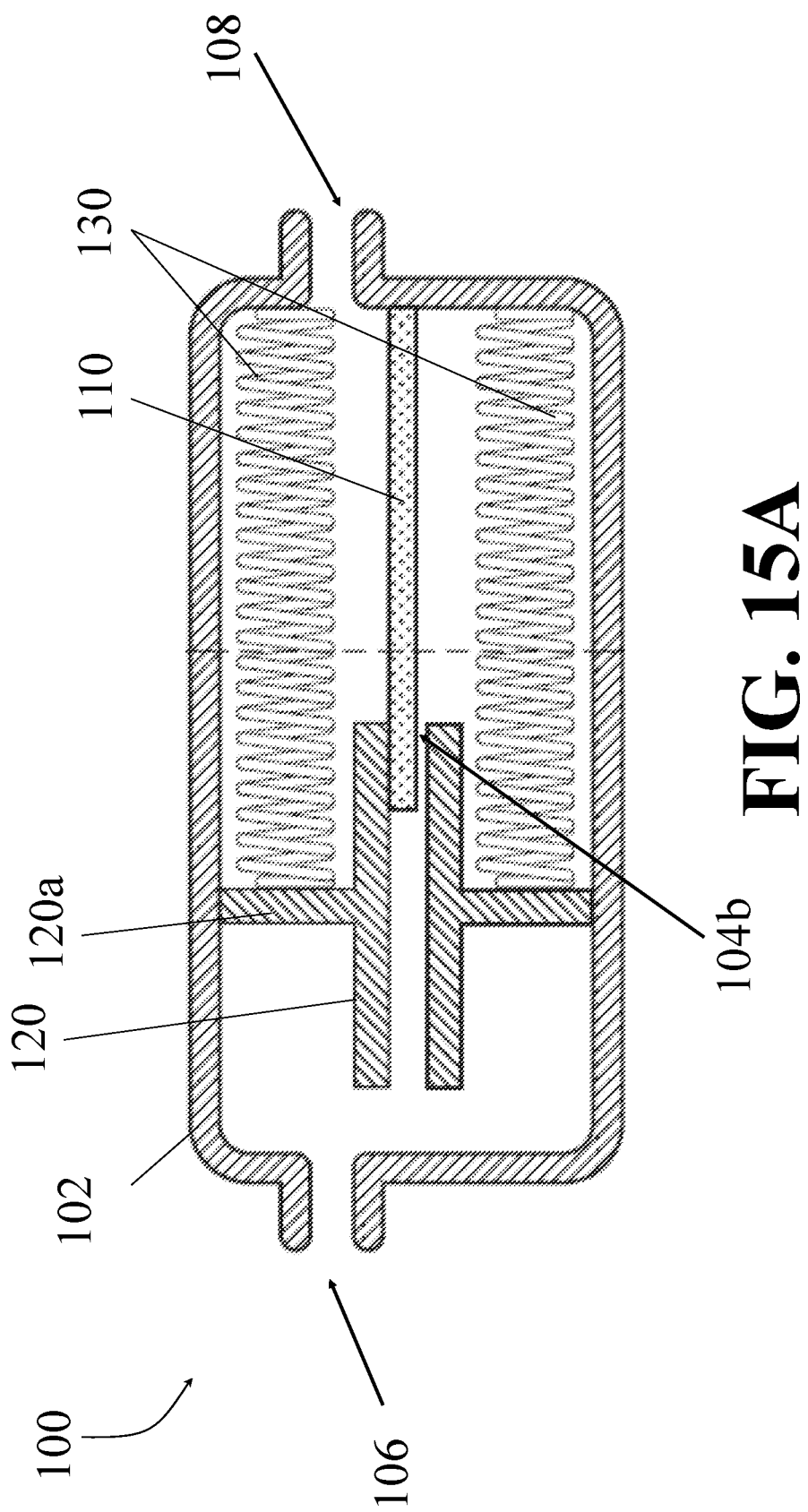
FIGS. 15A, 15B, 15C, 15D, and 15E are example cross-sectional side views of a variable flow resistor, in accordance with some embodiments of the present disclosure.

Referring to FIG. 15A, in some embodiments, the moveable element 120 positioned over a restrictor 110 can be coupled to one or more biasing mechanisms 130. For example, one or more biasing mechanisms 130 can be coupled to the substantially vertical surface 120a of the moveable element 120. The one or more biasing mechanisms 130 can provide spring force in an opposing direction to a force being applied to the substantially vertical surface 120a of the moveable element 120 by a fluid flow from the input 106. As discussed herein, the biasing mechanisms 130 can be coupled to either side of the moveable element 120. In some embodiments, as depicted in FIG. 15A, the substantially vertical surface 120a can extend to the interior of the chamber 102 to form a sealed partition between the input 106 and output 108, such that the flow path of fluid through the VFR 100 is limited to the flow channel 104b created by the overlap of the moveable element 120 and the restrictor 110.

Figure 15B:
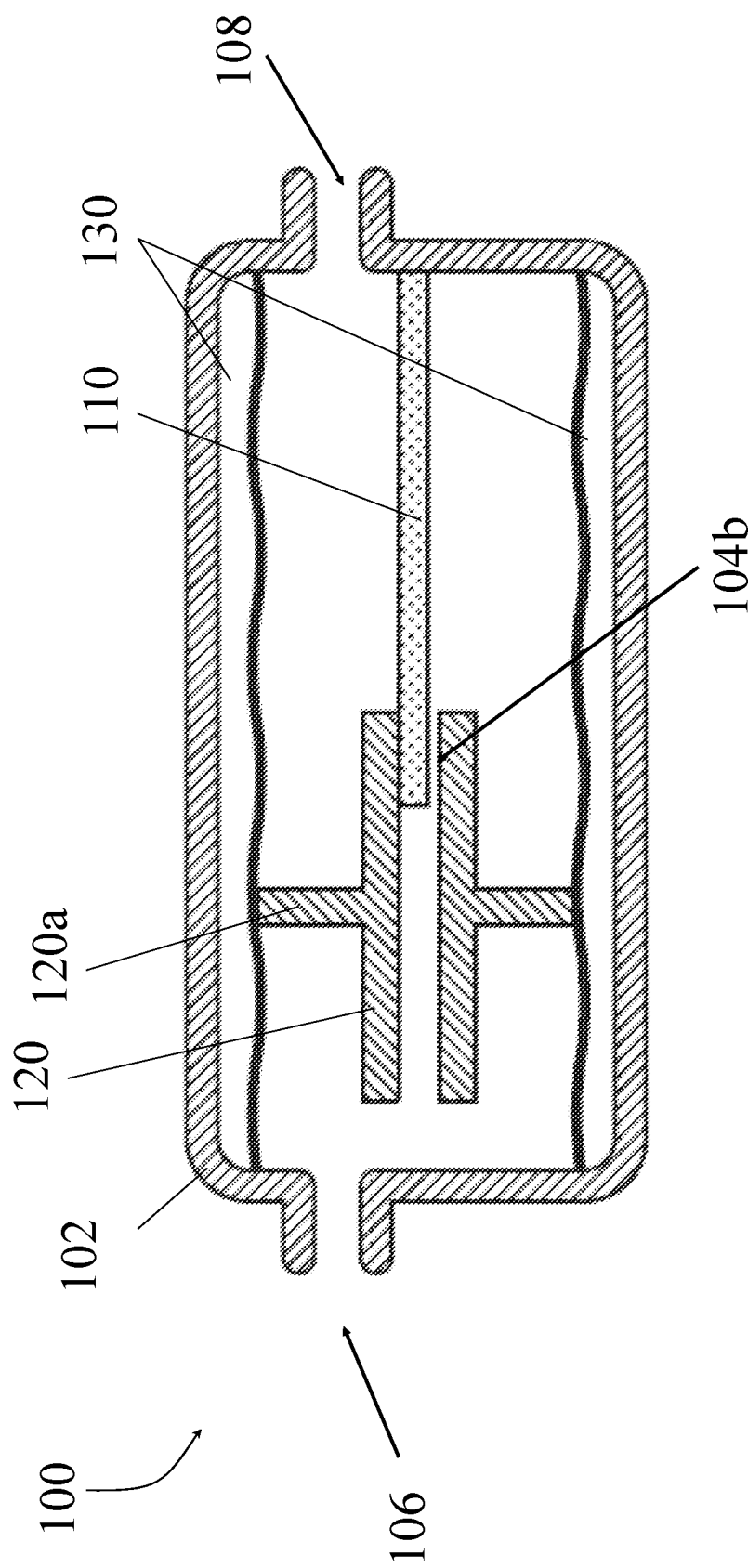
Figure 15C:
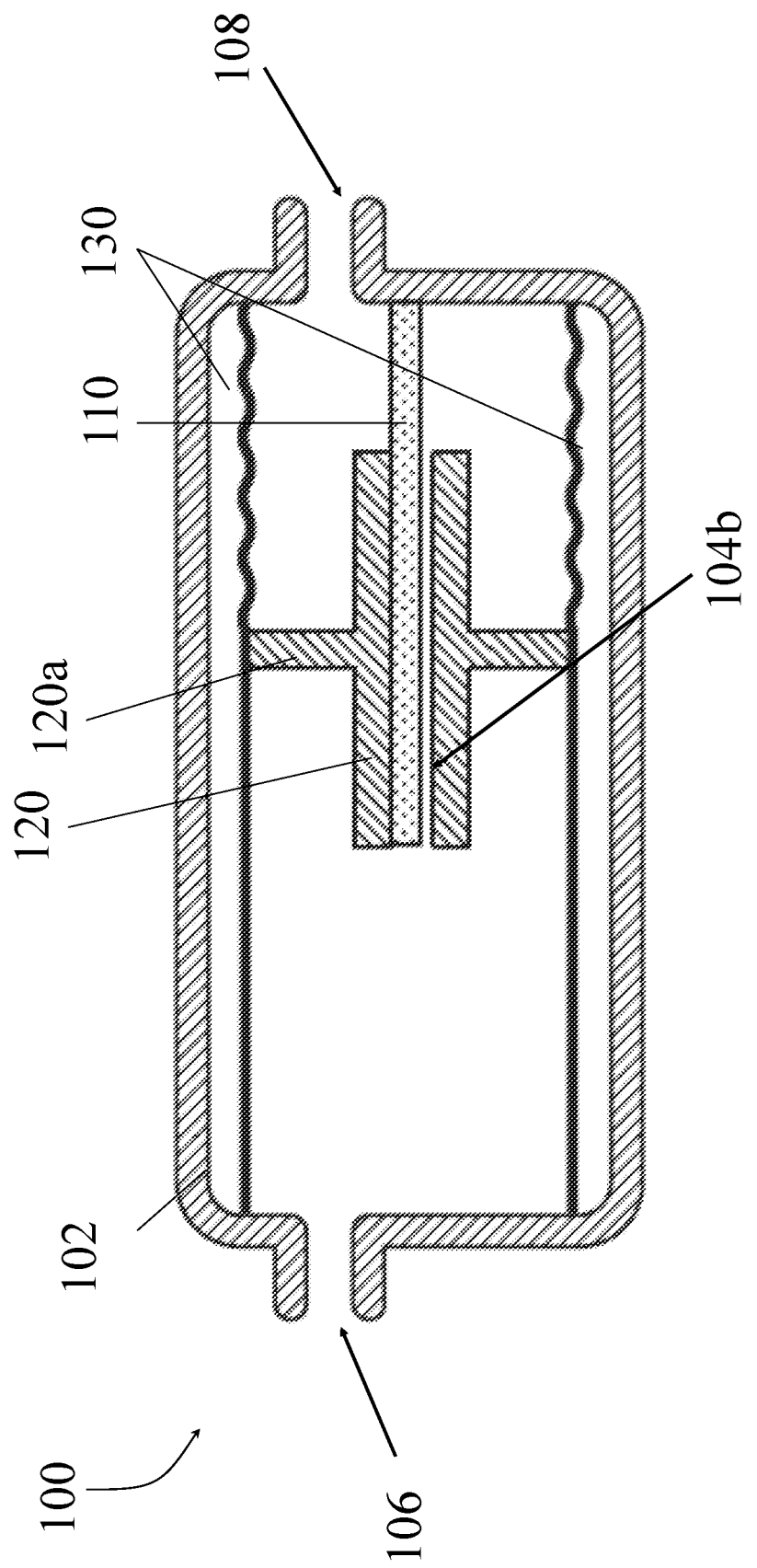

Referring to FIGS. 15B and 15C, in some embodiments, the VFR 100 can include the biasing mechanisms 130 can be an elastomeric liner to create a seal between the moveable element 120 and the interior of the chamber 102. The elastomeric liner can include any combination of materials that have elastic qualities that allow for compression, expansion, and returning to form when in a neutral state. In some embodiments, as depicted in FIGS. 15B and 15C, the elastomeric liner can line the inner circumferential portion of the chamber 102 and couple to the substantially vertical surface 120a of the moveable element 120 to form a sealed partition between the input 106 and output 108. For example, the substantially vertical surface 120a can be bonded to or embedded within the elastomeric liner using any combination of manufacturing methods. The sealed partition created by the elastomeric liner and the moveable element 120 limits the flow path of fluid through the VFR 100 to the flow channel 104b created by the overlap of the moveable element 120 and the restrictor 110. The elastomeric liner can be utilized in combination with or in lieu of an elastic member 130.

Referring to FIG. 15C, as pressure is applied to the substantially vertical surface 120a of the moveable element 120, for example, by the fluid flow entering through input 106, the moveable element 120 can be moved in a direction toward the distal end of the VFR 100. The moveable element 120 will move when the force applied to the substantially vertical surface 120*a* is greater than the resistant force of the elastomeric liner. For example, the force applied to the substantially vertical surface 120*a* must be sufficient to expand the proximal portion of the elastomeric liner and compress the distal portion of the elastomeric liner, as depicted in FIG. 15C.

Figure 15D:
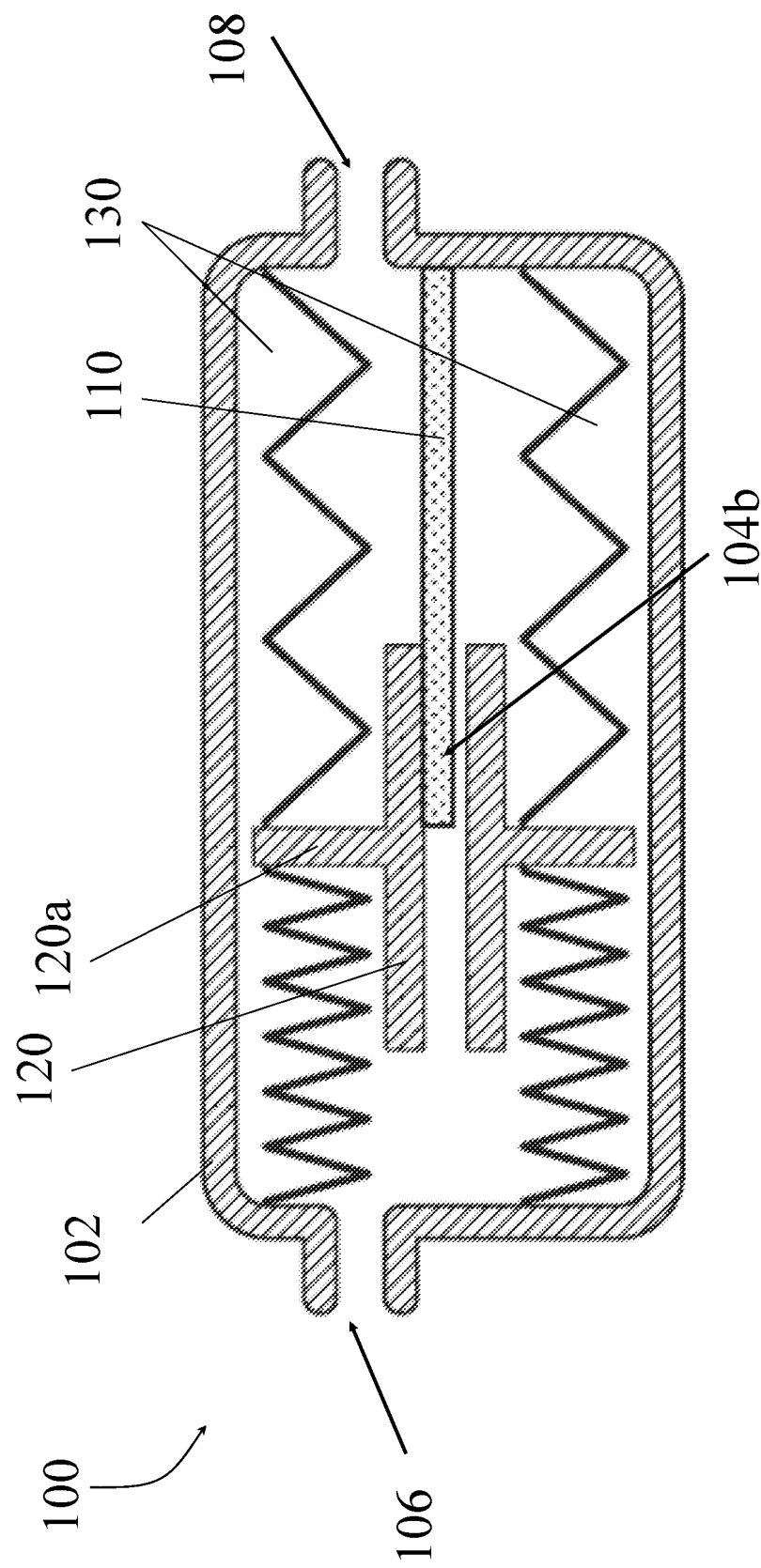
Figure 15E:
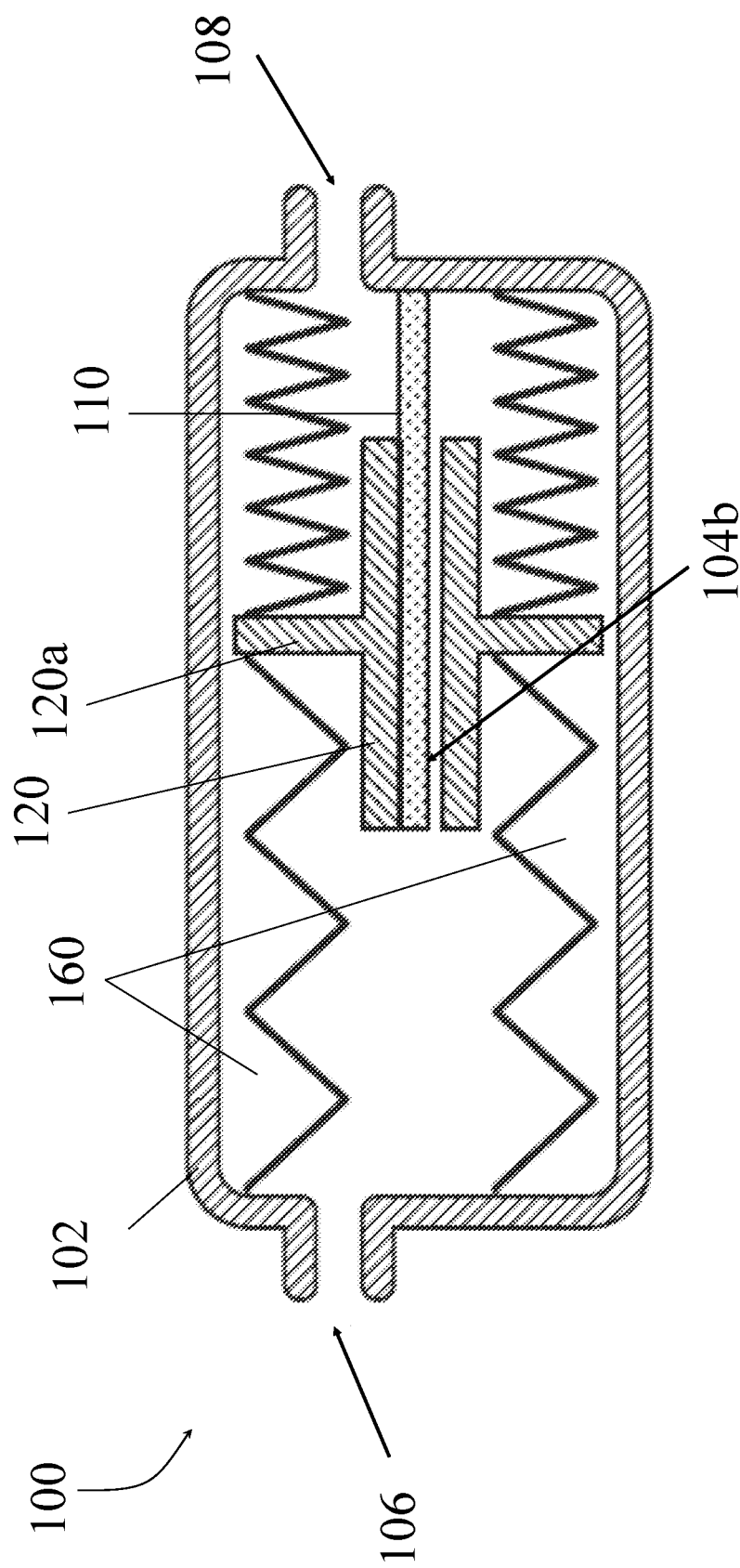

Referring to FIGS. 15D and 15E, in some embodiments, the biasing mechanism 130 can include a compressible accordion tube to create a seal between the moveable element 120 and the inner chamber 102. The accordion tube can include any combination of materials that have qualities that allow for compression, expansion, and returning to form when in a neutral state. The accordion tube should be constructed from a material and/or designed to provide some resistance in an opposing direction as the fluid flow force being applied to the substantially vertical surface 120*a* of the moveable element 120. For example, the accordion tube, for example constructed from an elastomer material, can be designed to provide a spring type force in accordance with Hook's law. In some embodiments, as depicted in FIGS. 15D and 15E, the accordion tube can line the inner circumferential portion of the chamber 102 and couple to the substantially vertical surface 120*a* of the moveable element 120 can extend to the accordion tube to form a sealed partition between the input 106 and output 108. The sealed partition created by the accordion tube and the moveable element 120 limits the flow path of fluid through the VFR 100 to the flow channel 104*b* created by the overlap of the moveable element 120 and the restrictor 110. The accordion tube can be utilized in combination with or in lieu of an elastic member 130.

Referring to FIG. 15E, as pressure, sufficient to counter the opposing force of the accordion tube, is applied to the substantially vertical surface 120*a* of the moveable element 120, for example, by the fluid flow entering through input 106 the moveable element 120 can be moved in a direction toward the distal end of the VFR 100. The moveable element 120 will move when the force applied to the substantially vertical surface 120*a* is greater than the resistant force of the accordion tube. For example, the force applied to the substantially vertical surface 120*a* must be sufficient to expand the proximal portion of the accordion tube and compress the distal portion of the accordion tube, as depicted in FIG. 15E.

Figure 16A:
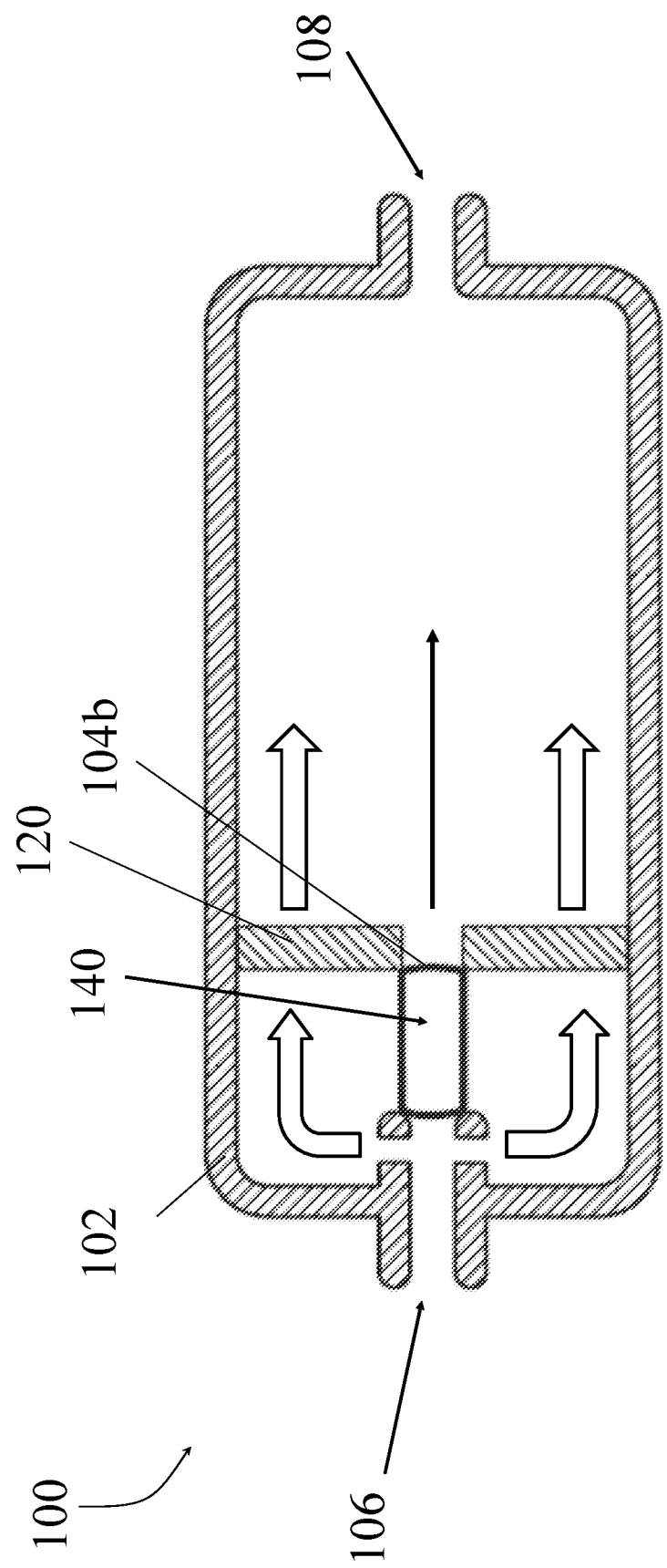
FIGS. 16A, 16B, 16C, and 16D are example cross-sectional side views of a variable flow resistor, in accordance with some embodiments of the present disclosure.
Figure 16B:
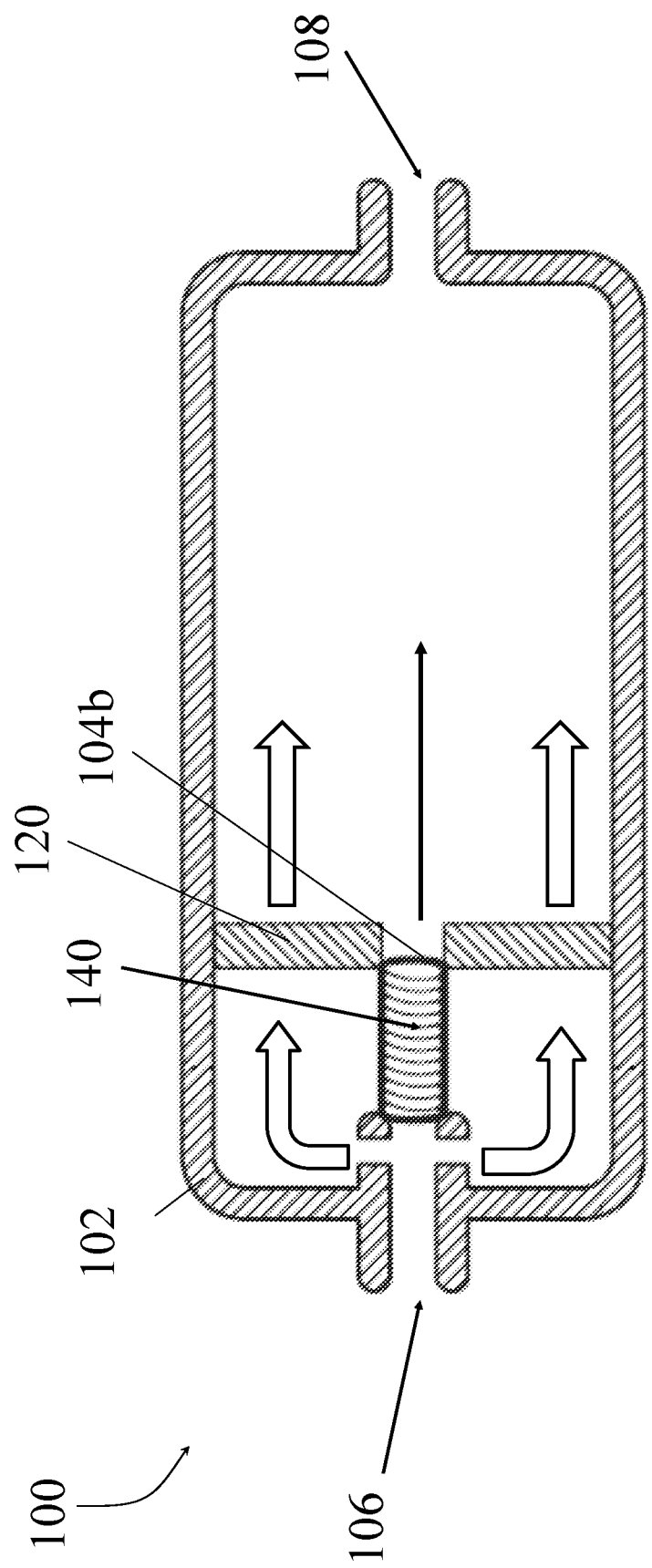

Referring to FIG. 16A, in some embodiments, the VFR 100 can be designed to modify a length of a flow path through a flow channel 104*b* within an elongating element 140 by adjusting a length of a flow channel 104*b* rather than a length of an overlap, as discussed with respect to FIGS. 1A-15E. The elongating element 140 can be coupled to the proximal end of the chamber 102 and a proximal end of a moveable element 120, as depicted in FIG. 16A. The elongating element 140 can be constructed and/or shaped in a manner that allows the elongating element 140 to elongate or stretch as a force is applied to the moveable element 120. For example, fluid entering the input 106 can flow through the flow channel 104*b* of the elongating element 140 and can also flow toward and apply a force to the moveable element 120 (represented by outlined arrows). As the fluid applies force to the moveable element 120, the force, sufficient to counter the opposing force of the elongating element 140, is applied to the substantially vertical surface 120*a* of the moveable element 120 can cause the elongating element 140 to extend to move the moveable element 120 toward the distal end of the chamber 120. In some embodiments, the elongating element 140 can extend without modifying the diameter of the flow channel 104*b* therethrough. As the elongating element 140 is elongated, the length of the flow channel 104*b* will be increased, effecting the flow rate (represented by the solid arrow) through said channel 104*a*. Referring to FIG. 16B, in some embodiments, can include an elongating element 140 with a supporting coil positioned therein (or around the elongating element 140) to prevent the elongating element 140 from collapsing when stretched. Otherwise, the device 100 of FIG. 16B can operate in a similar manner as the device 100 of FIG. 16A.

Figure 16C:
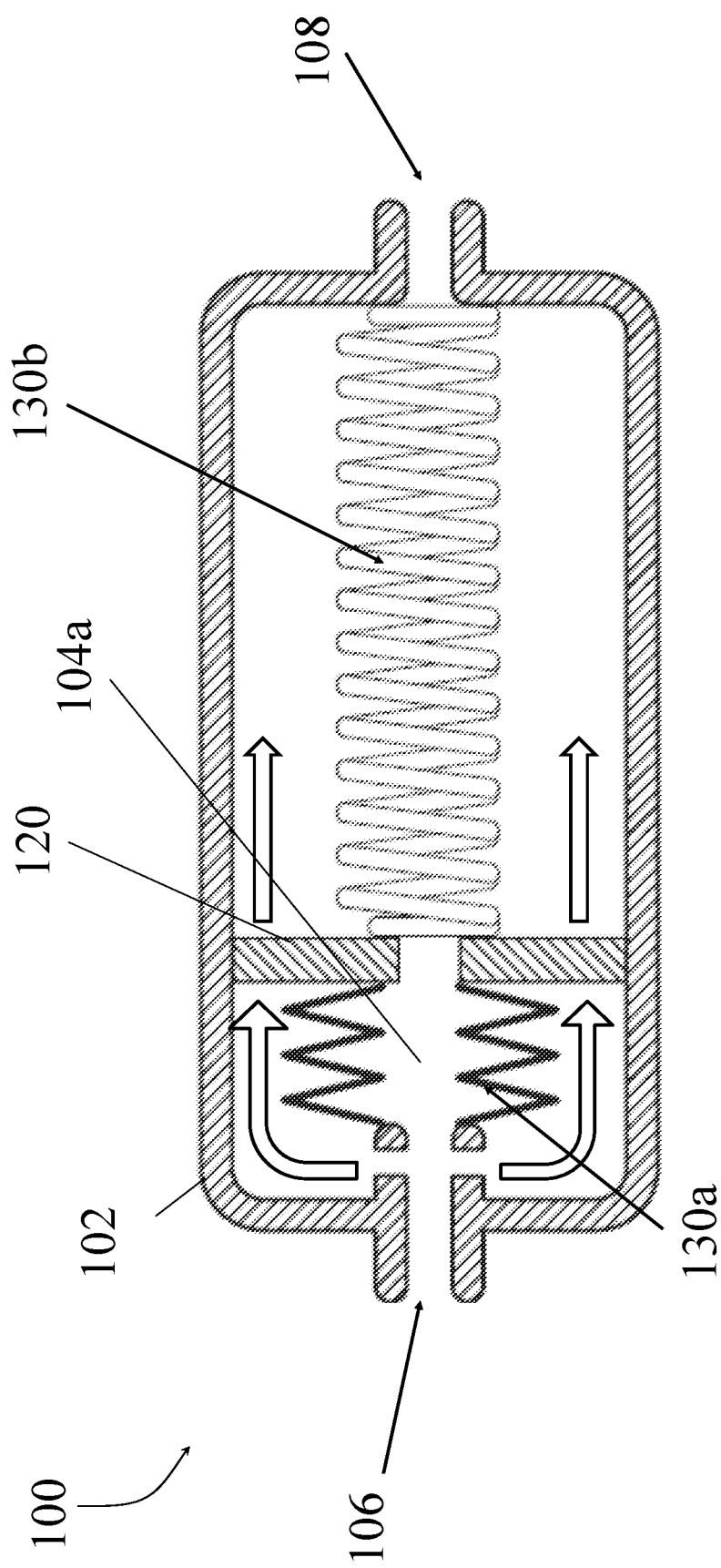

Referring to FIG. 16C, in some embodiments, the VFR 100 can include two or more different types of biasing mechanisms 130*a*, 130*b* with a CSA 104*a* extending therethrough. For example, the VFR 100 can include an accordion tube as a first biasing mechanisms 130*a* coupled to the proximal side of the chamber 102 and a proximal side of a moveable element 120 and a second biasing mechanisms 130*a* coupled to the distal side of the chamber 102 and a distal side of a moveable element 120, as depicted in FIG. 16C. The first biasing mechanisms 130*a* can be constructed and/or shaped in a manner that allows the accordion tube to elongate or stretch as a force is applied to the moveable element 120. For example, fluid entering the input 106 can flow through the CSA 104*a* of the accordion tube and can also flow toward and apply a force to the moveable element 120 (represented by outlined arrows). At the same time, the second biasing mechanism 103*b* (e.g., a spring) can provide a counter force pushing back toward the proximal end of the chamber 102. As the fluid within the chamber 102 applies force to the moveable element 120, the force can cause the moveable element 120 to move toward the distal end of the chamber 120 while elongating the first biasing mechanisms 130*a* and compressing the second biasing mechanisms 130*b*. The force being applied to the moveable element 120 must be sufficient to overcome the opposing forces applied by both the first biasing mechanisms 130*a* and the second biasing mechanisms 130*b*. As the first biasing mechanisms 130*a* is elongated, the length of the flow channel 104*b* will be increased, effecting the flow rate through said channel 104*a*.

Figure 16D:
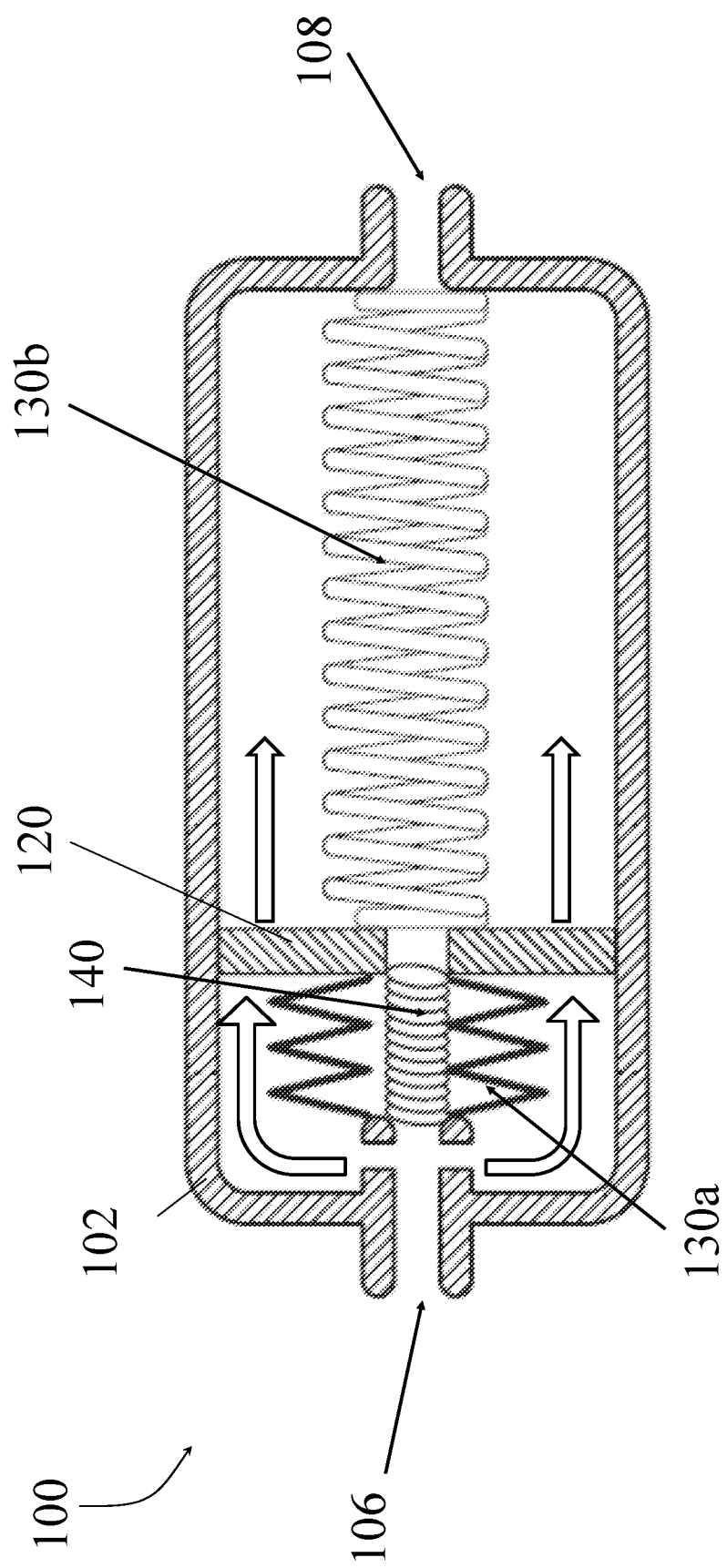

In some embodiments, the VFR 100 can include any combination of biasing mechanisms 130 such as springs, accordion tubes, and expandable flow channels to modify a length of a flow channel 104*b* through the expandable flow channel. Referring to FIG. 16D, an example embodiment of a VFR 100 is depicted with an accordion tube coupled to the proximal sides of the chamber 102 and moveable element 120, an elongating element 140 (also coupled to the proximal sides of the chamber 102 and moveable element 120) positioned within the accordion tube 106, and a spring coupled to the distal sides of the chamber 102 and moveable element 120.

Figure 17:
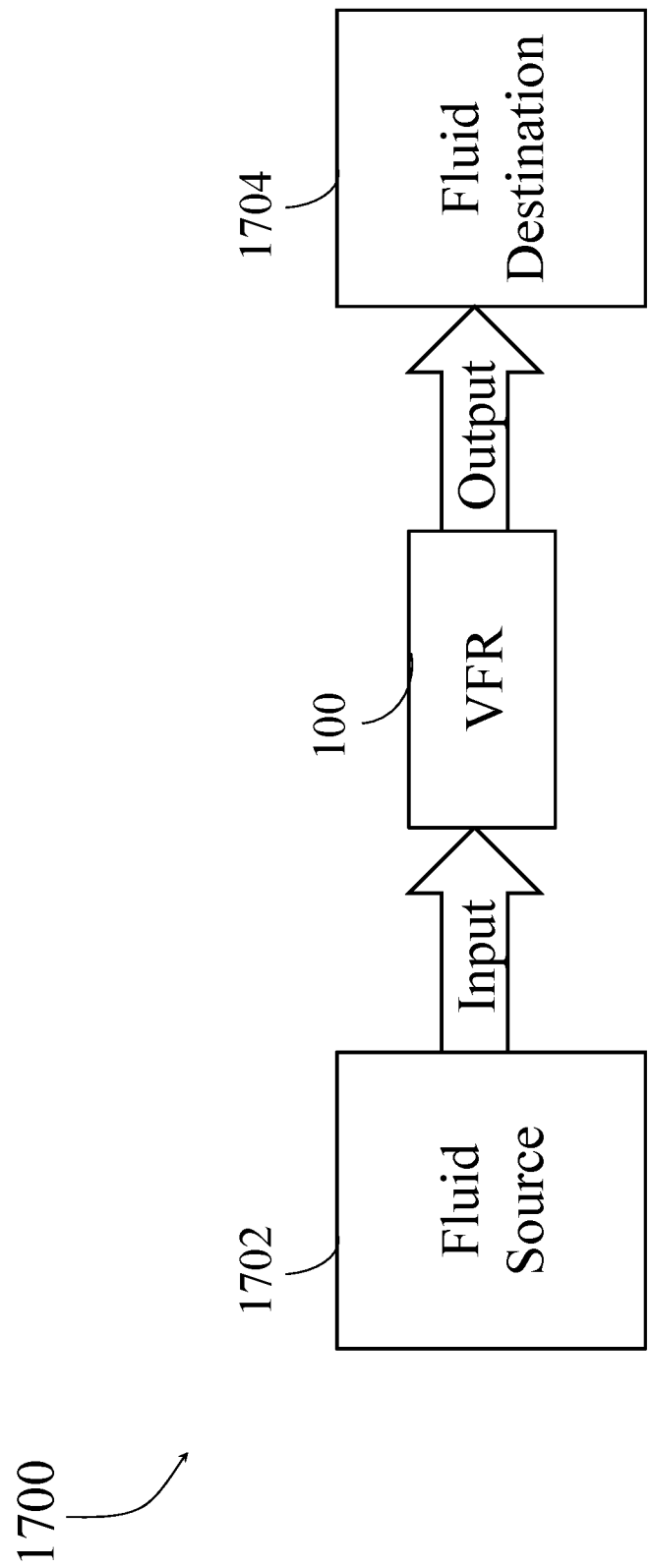
FIG. 17 is an example system implementing a variable flow resistor, in accordance with some embodiments of the present disclosure.

Referring to FIG. 17, in operation, the VFR 100 of the present disclosure can be implemented within a system 1700 for regulating a fluid flow from a fluid source 1702 to a fluid receptacle 1704. For example, the VFR 100 can be interposed between a fluid reservoir providing a flow of fluid at a given inlet pressure (via input 106) and a fluid receptacle being provide the flow of fluid at a given outlet pressure (via output 108). The positioning of the VFR 100 provides a fluid communication with the source 1702 at the input 106 and a fluid communication with the receptacle 1704 at output 108 to create a fluid communication line from the source 1702 to the receptacle 1704 with an output 108 flow to the receptacle 1704 at a desired flow rate regardless of the flow rate/pressure received at the input 106. The fluid flow can be delivered to the input 106 using any combination of delivery mechanisms, for example, pumped, gravity assisted, etc. The VFR 100 can also be integrated with a fluid reservoir and pressure source to form a fluid transfer system (e.g., an infusion device). When placed in between a fluid source 1702 and a fluid receptacle 1704, the passive VFR 100 can automatically adjust its resistance (R) to the pressure difference (ΔP) so that the flow through it is constant ($Q_0$), as represented in graph 1200 in FIG. 12C. In other words, the VFR 100 can be placed in line of a fluid flow to automatically adjust a fluid flow rate to a constant desired value to provide a passive variable resistor, for example, by adjusting the flow rate (Q) by modifying the length (L) of the flow channel 104b. These adjustments can be made using any combination of designs, structures, elements, features, functions, effects, etc. discussed with respect to FIGS. 1A-16D. The variable flow resistor 100 and methods of use can be applied to any combination of applications at any scale and is not intended to be limited to the example uses provided herein.

During operation, the physical characteristics of the VFR 100, allows the resistance to flow of fluid through the flow channel 104 to be directly related to the position of the moveable element 120 in the reduced cross-section area 104a (e.g., created by a restrictor 110), which in turn is determined by the balance of forces acting upon a moveable element 120 (e.g., spring forces). When implementing the VFR 100, when the inlet pressure is greater than the outlet pressure, the pressure difference (ΔP) drives the moveable element 120 in a direction towards the outlet 108. By moving the moveable element 120 toward a distal end of the chamber 102, the flow channel 104b (created by an overlap of the moveable element 120 and a restrictor 110) is lengthened which in turn increases the resistance across it. Similarly, when the input pressure decreases, reduced pressure being applied to the moveable element 120 causes it to move away from the outlet 108 (e.g., by recoil of the biasing mechanism 130). By moving away from the distal end of the chamber 102, the length (L) of the flow channel 104b is reduced, thus decreasing the resistance across it. Thus, at any given pressure difference (ΔP) the resistance (R) provided by the VFR 100 will be adjusted and the rate of fluid flow (Q) through the VFR 100 will remain a constant value (as defined by the characteristics of the VFR 100), assuming the pressure does not exceed a maximum pressure or falls below a minimum pressure (e.g., as reflected in FIG. 9).

Figure 18:
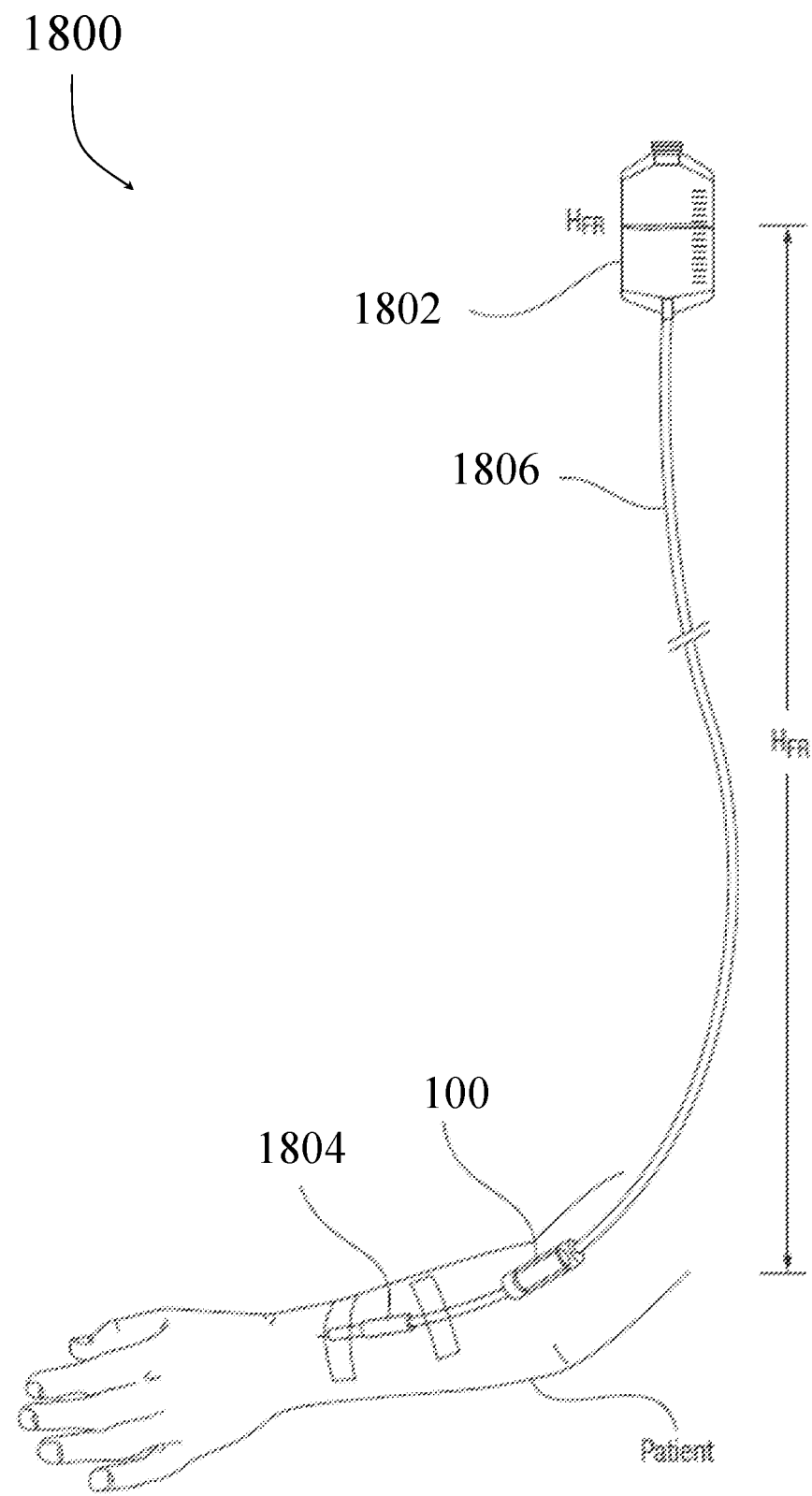
FIG. 18 is an example system implementing a variable flow resistor, in accordance with some embodiments of the present disclosure.
Figure 19:
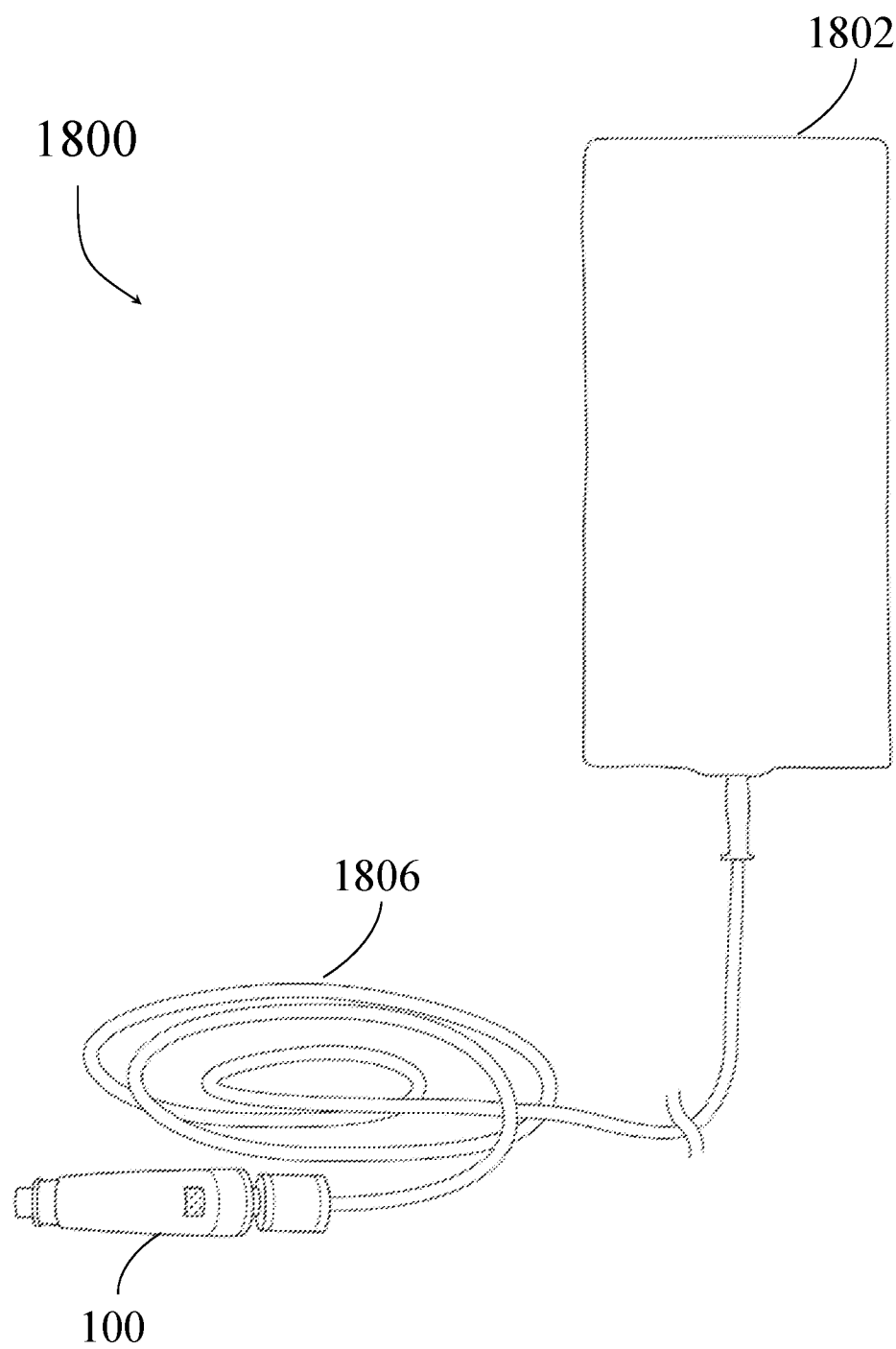
FIG. 19 is an example system implementing a variable flow resistor, in accordance with some embodiments of the present disclosure.

The consistent flow rate provided by the VFR 100 can be useful in a wide range and variety of applications where maintaining consistent flow independent of changes in pressure differential is desirable. For example, such features are particularly desirable in healthcare applications where precise control of the rate of flow of fluids, medications and other substances can have important clinical implications. Referring to FIG. 18, an embodiment of a medical device incorporating such a VFR 100 as a fixed flow rate intravenous infusion system 1800 is depicted. The intravenous infusion system 1800 has a proximal end including a fluid reservoir 1802 positioned above and coupled in fluid communication with a length of tubing 1806 coupled to the input 106 of the VFR 100.

The intravenous infusion system 1800 has a distal end including a catheter 1804 positioned proximate to and coupled in fluid communication with a short length of tubing 1806 coupled to the output 108 of the VFR 100. For example, the distal end of the VFR 100 connects to the catheter 1804, such as a peripheral intravenous catheter, which is positioned within a patient's vein at a particular venous pressure. The VRF 100 within the intravenous infusion system 1800 is designed to regulate the flow rate received from the fluid reservoir 1802 (e.g., created in part by the height $H_{FR}$) to correspond to the particular venous pressure at the catheter 1804.

In this system 1800 provided in FIG. 18, the input pressure of the VFR 100 is determined by the density of the fluid and the height of the column of fluid in the fluid reservoir relative to the position of the VFR (Pi=$H_{FR}$*Rho) where Pi is an input pressure, H is a height of fluid column (e.g., above a flow resistor), and Rho is the density of the fluid. The outlet pressure of the VFR 100 is selected based on the pressure in the patient's vein (Po=Pv). Therefore, the pressure differential is the difference between the input and outlet pressures in a linear function of the height of the fluid reservoir and the patient's venous pressure. ΔP=Pi−Po= ($H_{FR}$*Rho)−Pv. In a typical clinical setup of an IV infusion, the incorporation of the VFR 100 provides a desirable functionality whereby the flow of fluid into the patient (via the catheter 1804) is independent of the height of the fluid reservoir, across a specific operating range (e.g., Lmin–Lmax). Since the specific embodiment of the VFR 100 incorporated in the consistent flow infusion system 1800 has a pressure differential operating range, the maximum and minimum heights of the fluid reservoir are determined by the venous. Although the fluid reservoir height operating range is dependent on the patient's venous pressure, the constancy of the flow rate is not dependent on the patient's venous pressure as long as the fluid reservoir's height remains within its operating range.

In some embodiments, VFR 100 systems can be provided in multiple different fixed flow rates to provide different desired flow rates. A user can then select from the fixed rate VFRs 100 that are appropriate for their application and use that device to regulate a flow at the fixed rate. For example, each VFR 100 can include an identifier (e.g., SKU number, color, flow rate number, etc.) having a discrete flow rate. To enhance usability, the specified flow rates can also be visually differentiated by a printed number, color code or other means. With different devices for different flow rates, an operator can be offered a specified number of options covering fixed flow rate devices spanning a predetermined range of desired flow rates.

In some embodiments, VFR 100 systems can be adjustable. The VFR 100 can be adjustable using any combination of methods, for example, adjusting one or more dimensions of the chamber 102, adjusting a length of a stop 122 (e.g., via a rotational mechanism), adjusting an amount of travel for a moveable element 120 (e.g., via a rotational mechanism), adjusting a size and/or position of a restrictor 110, etc. When the VFR 100 is designed to be adjustable, an appropriate indicator can be provided such that the user can clearly identify a current flow rate being regulated by the VFR 100. For example, a rotational mechanism can have lines/numerals designating different resistance values thereon. An adjustable version would allow the user to select the flow rate that they want by adjusting or rotating a mechanism.

The embodiments of the present disclosure provide a consistent flow gravity-driven infusion, without the need for electronic infusion pumps, that is independent of the height of the IV bag. This means that consistent flow is maintained despite any inadvertent changes in the height of the bag or movement of the patient from a supine position to sitting to ambulating. Since the resistance of the VFR 100 is dependent on the pressure differential and not the input pressure alone, the device maintains consistent flow despite changes in the patient's venous pressure from fluid loss, dehydration, fluid overload, and any patient movement which would affect the vertical position of the catheter. Therefore, the VFR 100 can provide a completely disposable intravenous (IV) infusion set designed to deliver highly-accurate gravity-driven infusions independent of the variables facing existing current gravity based system, (e.g., height of the IV bag, hydration level changes in the patient, etc.). It can maintain a consistent flow by incorporating a passive variable flow-resistor.

Referring to FIGS. 19A, the VFR 100 can be provided separate from or combined with different fluid reservoirs 1802, allowing it to be customizable with the full range of fluid sources, such as IV bags of different sizes and content. In some embodiments, the VFR 100 can be provided as part of a kit to incorporate a variety of other clinically useful features such as stopcock valves, y-connectors, drip chambers, kink resistant tubing 1806, and filters at any position along the length.

In some embodiments, all of the components of the VFR 100 and its related system/kit components can utilize inexpensive, easy-to-manufacture, disposable mechanical parts, adjusts its resistance to flow based on the input pressure. The VFR 100 can also be provided across a range of typically prescribed flow rates for different medications, fluids and other substances. The VFR 100 provides additional safety features, which cannot physically be exceeded despite human error, as well as protection against dangerous air embolism and IV infiltration. For example, the operation of the VFR 100 prevents dangerous air bubbles inadvertently introduced into the system from passing into the patient under clinically relevant conditions. Similarly, flow from the VFR 100 can also stop when meaningful resistance is encountered, which is important in preventing dangerous infiltration of certain medications when an intravenous catheter dislodges from a vein. In some embodiments, the VFR 100 can incorporate a sensor/alarm so that if the tubing 1806 is kinked and the flow stops, an alarm would go off to alert the user. Finally, the VFR 100 can be physically incapable of inadvertently delivering flows higher than its specified rate—a serious medication error associated with electronic infusion pumps. In some embodiments, the VFR 100 can be designed with a code (e.g., QR, SKU, etc.) that the user can scan and allows an administrative system to notify the user about the progress of the fluid transfer (e.g., infusion).

Figure 20A:
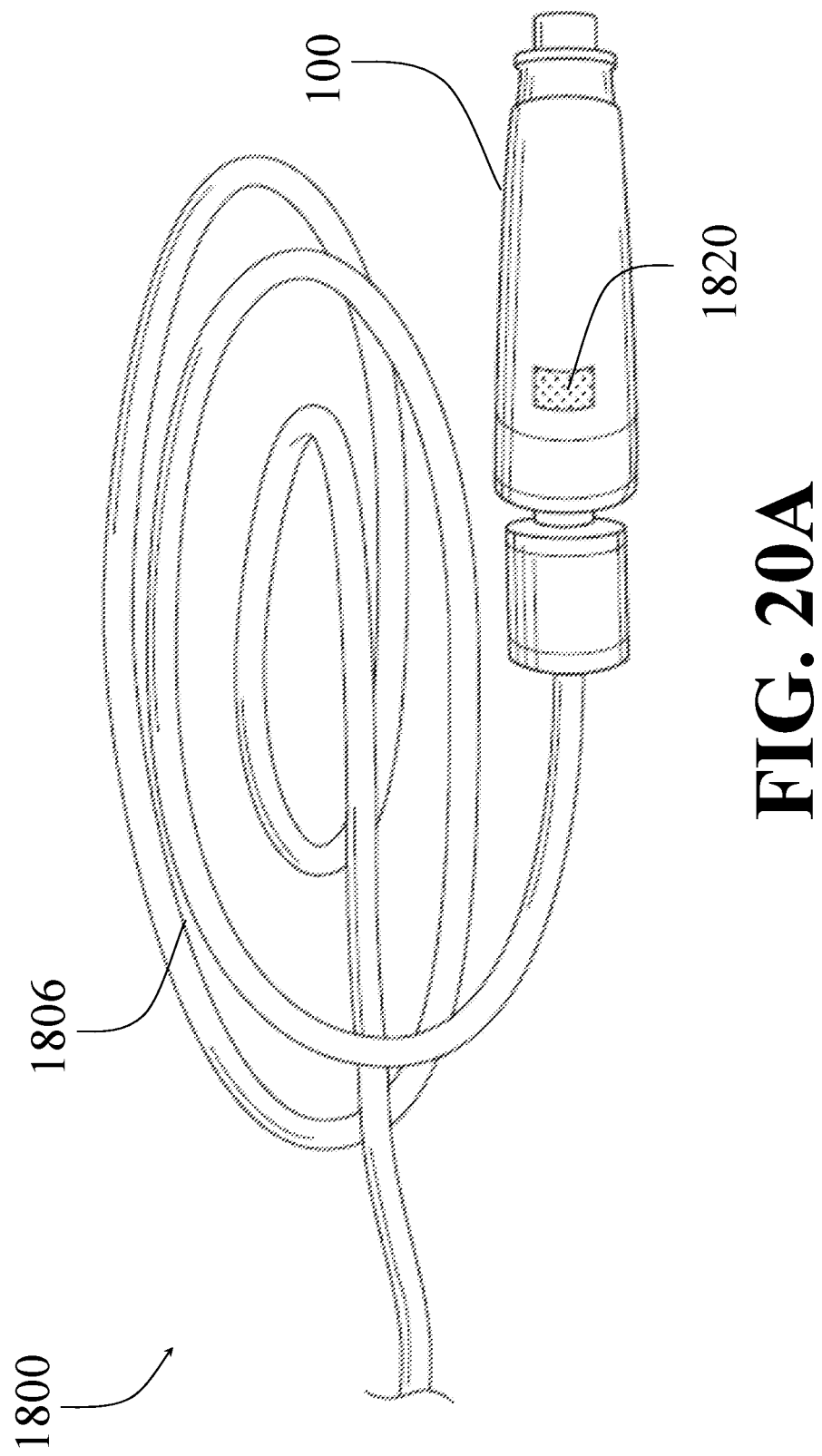
FIGS. 20A and 20B are example illustrative views of a variable flow resistor, in accordance with some embodiments of the present disclosure.
Figure 20B:
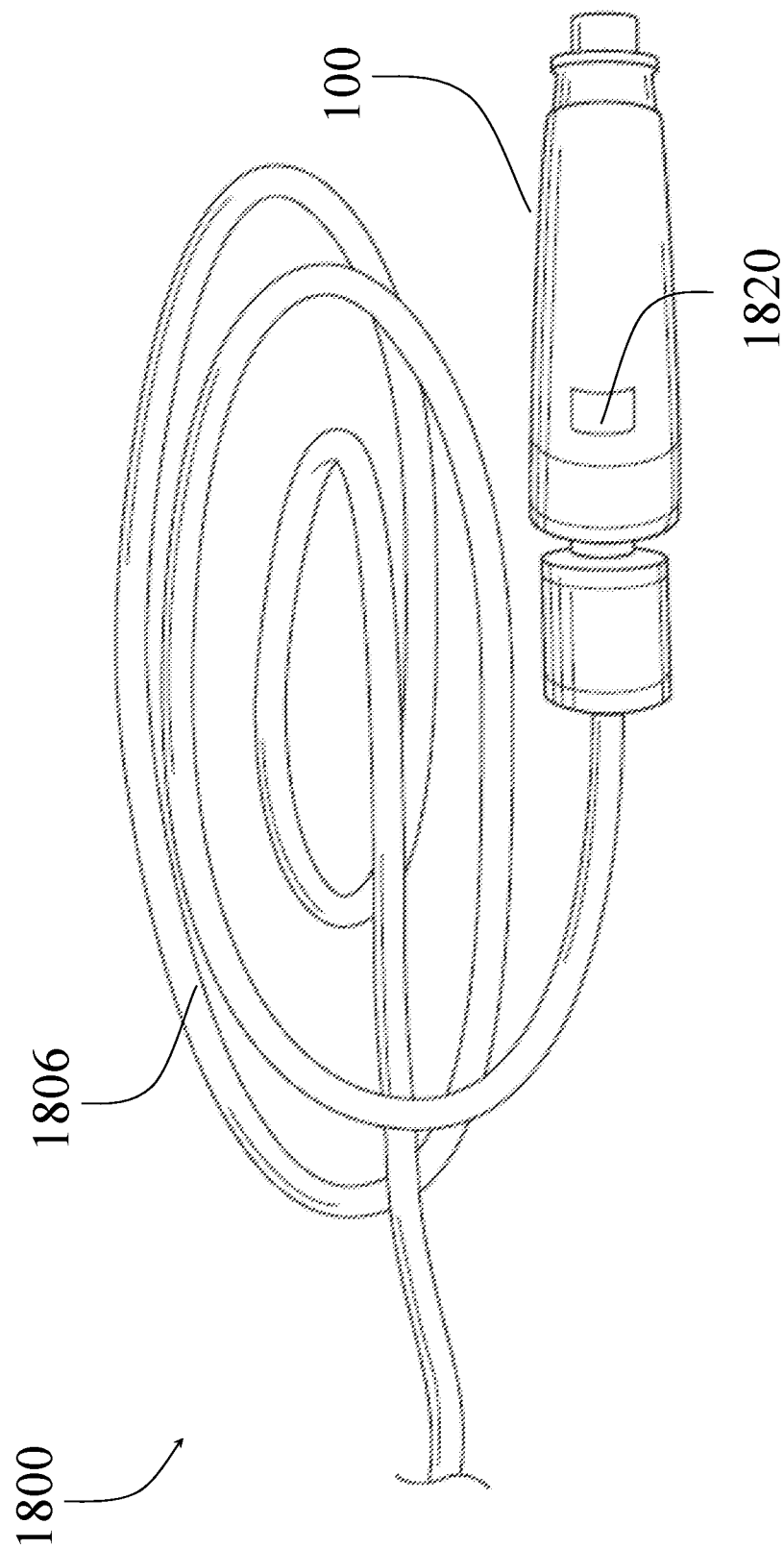

Referring to FIGS. 20A and 20B, in some embodiments, the VFR 100 can include a flow indicator 1820 designating whether there is an active flow through the VFR 100. In some embodiments, the VFR 100 can have a window that exposes a pressure indicator 1820. For example, the moveable element 120 moving in front of the window can indicate a certain amount of resistance being applied by the flow resistor, for example, as shown in FIG. 20A. In other words, the moveable element 120 itself can act as the flow indicator. Similarly, if none of the moveable element 120 is visible, then it may indicate that there is not currently a fluid flow through the VFR 100, for example, as shown in FIG. 20B. In some embodiments, the moveable element 120 can unmask an underlying component to indicate that there is flow. For example, movement of the moveable element 120 can expose an underlying element that is revealed in the flow indicator 1820 window when the moveable element 120 is no longer blocking the underlying flow indicator 1820.

Another useful embodiment of the current invention is implementation with a highly accurate disposable infusion pump (DIP). DIP on their own are inaccurate because the common methods of generating infusion pressures (elastomeric balloons, springs, pressurize gas) all demonstrate declining input pressure through the course of the infusion. A DIP which uses any of these, which combines any of these with a consistent flow variable resistor 100 as discussed herein can directly solve inaccuracy issues by lowering the resistance during the course of the infusion to achieve consistent flow.

EXAMPLES

Testing a VFR 100 of the present disclosure has provided evidence that a consistent flow can be maintained even when the pressure was repeatedly changed during the course of a fluid transfer (e.g., infusion). The most definitive test from a clinical point of view (Figure) was performed in a physiologic bench top model which mimics saline infusions into a vein in a patient's forearm against a typical venous back pressure. Two Identical VFR 100 were each connected to an IV bag containing a specified volume of saline fluid and attached to one of the models. For one infusion (A) the bag was hung at approximately 50 cm (less than 2 feet) above the arm, which would be unusually low in a clinical setting. For the other infusion (B) the bag was hung at approximately 150 cm (5 feet) above the arm, close to the ceiling, which would be unusually high. The two infusions were initiated at the same time. Both sets completed their infusions at the same time indicating identical average flow rates, despite the fact that one infusion (B) was driven by approximately three times the pressure of the other infusion (A).

EXAMPLES

The passive variable flow resistor 100 of the present invention can be used to provide a consistent flow rate output (e.g., at output 108) regardless of the pressure and flow rate received at the input 106 of the VFR 100. For the below calculations, it is assumed that a compression type biasing mechanism 130, for example, a compression spring is used to provide the resistance to the input flow at the moveable element 120. Additionally, calculations for two geometries of the flow channel 104—one approximating a circular tube of cross sectional area a and one as a rectangular tube of width w>height h are provided below.

The resistance to flow through the VFR 100 can be directly related to this length (L), which is determined by the position of the moveable element 120 in the CSA 104a, which in turn is determined by the balance of forces acting upon it (e.g., pressure P from the input flow and counterbalancing force provided by the biasing mechanism 130. Since the inlet pressure can be greater than the outlet pressure, the pressure difference P drives the moveable element 120 towards the outlet 108, lengthening the flow channel 104b and increasing the resistance across it. The recoil of the biasing mechanism $F_s$ drives the moveable element 120 away from the outlet 108, shortening the flow channel 104b and decreasing the resistance across it. Thus, at any given pressure difference P $$F_s = AP$$

Assuming an ideal spring which obeys Hooke's Law, the recoil force of the biasing mechanism 130 is proportional to the compression of the biasing mechanism 130.

$$F_S = k(s_0 - s)$$

$$P = \frac{k(s_0 - s)}{A}$$

Circular Tube

If the flow channel 104 is assumed to be a circular tube with cross sectional area 104a a, the flow Q through the flow channel 104b can be determined by the Hagen-Poiseuille equation $$Q_0 = \frac{P}{R(l)} = \frac{a^2 k (s_0 - s)}{8\pi \mu l A}$$

$$l = \frac{a^2 k (s_0 - s)}{8\pi \mu Q_0 A}$$

The structure of the VFR 100, specifically the geometric relationship and interaction between the biasing mechanism 130 and the moveable element 120 dictate that $$\Delta s = -\Delta l$$

$$s + l = \text{constant}$$

$$\frac{a^2 k}{8\pi \mu Q_0 A} = 1$$

$$s + l = s_0$$

$$l = s_0 - s = \frac{AP}{k}$$

A minimum set of parameters can be specified from which the other parameters can be derived. One such set includes $Q_0$=Target Flow Rate
$P_{max}$, $P_{min}$=Maximum and Minimum Pressure Gradients
A=Piston Channel Area
a=Flow Channel Area
$s_{cmax}$=Maximum spring compression From these, the remaining parameters can be calculated $$k = \frac{8\pi \mu Q_0 A}{a^2}$$

$$l_{max} = \frac{AP_{max}}{k}$$

$$l_{min} = \frac{AP_{min}}{k}$$

$$s_0 = \frac{l_{max}}{s_{cmax}}$$

Rectangular Tube

The laminar flow properties of a fluid with density ρ through a rectangular tube of width w>height h can be estimated as follows $$D_h = \text{Hydraulic Diameter} = \frac{2hw}{h+w}$$

$$\eta = \text{kinematic viscosity} = \frac{\mu}{\rho}$$

$$\text{Re} = \text{Reynolds Number} = \frac{Q_0 D_h}{\eta a}$$

As long as the Reynolds number is low, flow is laminar and the hydraulic resistance and flow can be estimated as $$R_h = \text{Hydraulic Resistance} = \frac{12 \mu l}{w h^3 \left(1 - 0.63 \frac{h}{w}\right)}$$

$$Q_0 = \frac{P}{R_h(l)} = \frac{k w h^3 \left(1 - 0.63 \frac{h}{w}\right)(s_0 - s)}{12 \mu l A}$$

$$l = \frac{k w h^3 \left(1 - 0.63 \frac{h}{w}\right)(s_0 - s)}{12 \mu Q_0 A}$$

As with the circular tube, $$\Delta s = -\Delta l$$

$$s + l = \text{constant}$$

$$\frac{k w h^3 \left(1 - 0.63 \frac{h}{w}\right)}{12 \mu Q_0 A} = 1$$

$$s + l = s_0$$

$$l = s_0 - s = \frac{AP}{k}$$

Again, a minimum set of parameters can be specified from which the other parameters can be derived. One such set includes $Q_0$=Target Flow Rate
$P_{max}$, $P_{min}$=Maximum and Minimum Pressure Gradients
A=Piston Channel Area
w=Flow Channel Width
h=Flow Channel height
$s_{cmax}$=Maximum spring compression From these, the remaining parameters can be calculated $$k = \frac{12 \mu Q_0 A}{w h^3 \left(1 - 0.63 \frac{h}{w}\right)}$$

$$l_{max} = \frac{AP_{max}}{k}$$

$$l_{min} = \frac{AP_{min}}{k}$$

$$s_0 = \frac{l_{max}}{s_{cmax}}$$

These calculations effectively show, that by including the biasing element 130 (e.g., a spring), it linearizes the relationship between the pressure and the resistance to flow.

As utilized herein, the terms "comprises" and "comprising" are intended to be construed as being inclusive, not exclusive. As utilized herein, the terms "example", "example", and "illustrative", are intended to mean "serving as an example, instance, or illustration" and should not be construed as indicating, or not indicating, a preferred or advantageous configuration relative to other configurations. As utilized herein, the terms "about", "generally", and "approximately" are intended to cover variations that may existing in the upper and lower limits of the ranges of subjective or objective values, such as variations in properties, parameters, sizes, and dimensions. In one non-limiting example, the terms "about", "generally", and "approximately" mean at, or plus 10 percent or less, or minus 10 percent or less. In one non-limiting example, the terms "about", "generally", and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present disclosure will be apparent to those skilled in the art in view of the foregoing description. Accordingly, this description is to be construed as illustrative only and is for the purpose of teaching those skilled in the art the best mode for carrying out the present disclosure. Details of the structure may vary substantially without departing from the spirit of the present disclosure, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present disclosure be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A variable flow resistor device, the device comprising:
   a flow chamber having an input at a proximal end of the flow chamber, the input configured to expose the flow chamber to an input pressure of a fluid flow from a fluid source, an output at a distal end of the flow chamber, the output configured to expose the flow chamber to an outlet pressure, the outlet pressure comprising a back pressure acting on the output, a sidewall, a flow chamber length between the input and the output, and a symmetrical interior shape, the flow chamber configured to define a cavity between the input and the output, the cavity accessible by and in fluid communication with the input and the output, the cavity defined by the symmetrical interior shape and the sidewall of the flow chamber;
   a restrictor disposed entirely within the flow chamber, the restrictor having a restrictor length shorter than the flow chamber length and a constant cross-section along the entire restrictor length, the restrictor configured to define a reduced cross-sectional area within the flow chamber over the length of the restrictor between the cavity and the output;
   a moveable element having a cross-sectional area less than the reduced cross-sectional area, the moveable element configured to traverse a range of positions within the flow chamber in the presence of the input pressure and the outlet pressure acting on the moveable element, the range of positions including an overlap position at least partially within the reduced cross-sectional area, in the overlap position the moveable element configured to provide a flow channel between the restrictor and the moveable element, in the presence of a differential between the input pressure and the outlet pressure within a pressure differential operating range the flow channel configured to provide a substantially consistent output flow rate; and
   a biasing mechanism within the flow chamber mechanically interfaced with the moveable element, the biasing mechanism configured to restrain the moveable element and allow the moveable element to traverse within the range of positions in the presence of a sufficient pressure differential.

2. The device of claim 1, wherein the restrictor includes a structure extending from the sidewall of the chamber.

3. The device of claim 1, wherein a minimum length and a maximum length of the flow channel is defined by a minimum overlap and a maximum overlap between the moveable element and the restrictor.

4. The device of claim 3, wherein the chamber includes one or more stops to establish at least one of the minimum overlap or maximum overlap between the moveable element and the restrictor.

5. The device of claim 1, wherein the moveable element is a piston.

6. The device of claim 1, wherein the biasing mechanism is coupled to at least one end of the moveable element and at least one end of the chamber.

7. The device of claim 6, wherein the biasing mechanism includes at least one of a spring, an elastomer liner, an accordion, an elongating element, or a combination thereof.

8. The device of claim 1, wherein the moveable element traversing within the reduced cross-sectional area modifies a length of the flow channel as an amount of overlap between the moveable element and the reduced cross-sectional area changes in response to the differential changing within the pressure differential operating range to provide the substantially consistent output flow rate.

9. A system for implementing a controlled flow rate, the system comprising:
   a fluid source;
   a variable flow resistor device being in fluid communication with the fluid source, and includes:
      a flow chamber having an input at a proximal end of the flow chamber, the input configured to expose the flow chamber to an input pressure of a fluid flow from the fluid source and having an output at a distal end of the flow chamber, the output configured to expose the flow chamber to an outlet pressure, the outlet pressure comprising a back pressure acting on the output, a sidewall, a flow chamber length between the input and the output, and a symmetrical interior shape, the flow chamber configured to define a cavity between the input and the output, the cavity accessible by and in fluid communication with the input and the output, the cavity defined by the symmetrical interior shape and the sidewall of the flow chamber;
      a restrictor disposed entirely within the flow chamber, the restrictor having a restrictor length shorter than the flow chamber length and a constant cross-section along the entire restrictor length, the restrictor configured to define a reduced cross-sectional area within the flow chamber over the length of the restrictor between the cavity and the output; and a moveable element having a cross-sectional area less than the reduced cross-sectional area, the moveable element configured to traverse a range of positions within the flow chamber in the presence of the input pressure and the outlet pressure acting on the moveable element, the range of positions including an overlap position at least partially within the reduced cross-sectional area, in the overlap position the moveable element configured to provide a flow channel between the restrictor and the moveable element, in the presence of a differential between the input pressure and the outlet pressure within a pressure differential operating range the flow channel configured to provide a substantially consistent output flow rate; and a biasing mechanism within the flow chamber mechanically interfaced with the moveable element, the biasing mechanism configured to restrain the moveable element and allow the moveable element to traverse within the range of positions in the presence of a sufficient pressure differential; and a pathway to direct fluid from the fluid source through the flow chamber and to a point of delivery.

10. The system of claim 9, wherein the variable flow resistor device automatically adjusts its resistance (R) to an input pressure difference ($\Delta P$) from the fluid source so that a flow through the output of the variable flow resistor device is constant ($Q_0$).

11. The system of claim 9, wherein the biasing mechanism is coupled to at least one end of the moveable element and at least one end of the chamber, wherein the biasing mechanism includes at least one of a spring, an elastomer liner, an accordion, an elongating element, or a combination thereof.

12. A method for delivering a constant fluid flow, the method comprising:

providing variable flow resistor having:

a flow chamber having an input exposed at a proximal end of the flow chamber, the input configured to expose the flow chamber to an input pressure of a fluid flow from a fluid source, an output at a distal end of the flow chamber, the output configured to expose the flow chamber to an outlet pressure, the outlet pressure comprising a back pressure acting on the output, a sidewall, a flow chamber length between the input and the output, and a symmetrical interior shape, the flow chamber configured to define a cavity between the input and the output, the cavity accessible by and in fluid communication with the input and the output, the cavity defined by the symmetrical interior shape and the sidewall of the flow chamber;

a restrictor disposed entirely within the flow chamber, the restrictor having a restrictor length shorter than the flow chamber length and a constant cross-section along the entire restrictor length, the restrictor configured to define a reduced cross-sectional area within the flow chamber over the length of the restrictor between the cavity and the output; and a moveable element having a cross-sectional area less than the reduced cross-sectional area, the moveable element configured to traverse a range of positions within the flow chamber in the presence of the input pressure and the outlet pressure acting on the moveable element, the range of positions including an overlap position at least partially within the reduced cross-sectional area, in the overlap position the moveable element configured to provide a flow channel between the restrictor and the moveable element, in the presence of a differential between the input pressure and the outlet pressure within a pressure differential operating range the flow channel configured to provide a substantially consistent output flow rate; and a biasing mechanism within the flow chamber mechanically interfaced with the moveable element, the biasing mechanism configured to restrain the moveable element and allow the moveable element to traverse within the range of positions in the presence of a sufficient pressure differential;

coupling the variable flow resistor to the fluid source via the input of the flow chamber; and allowing the variable flow resistor to control the fluid flow within the flow chamber to deliver fluid from the fluid source to a point of delivery at a consistent fluid flow rate.

13. The method of claim 12, wherein the variable flow resistor modifies a variable inlet pressure to the consistent fluid flow rate.

14. A variable flow resistor device, the device comprising:

a fluid chamber having an input exposed to a first pressure from a fluid source and an output exposed to a second pressure from a point of delivery, the second pressure being a back pressure acting on the output;

a restrictor positioned entirely within the chamber between the input and the output, the restrictor having a constant cross section along its entire length and defining a reduced cross-sectional area; and a moveable element, in the presence of the first pressure and the second pressure acting on the moveable element, is configured to bias along the restrictor to define a fluid flow channel between an interior surface of the restrictor and the moveable element, the fluid flow channel configured to provide a substantially consistent output flow rate in the presence of a differential between the first pressure and the second pressure.

* * * * *